US012788517B2

(12) United States Patent
Chassot et al.

(10) Patent No.: US 12,788,517 B2
(45) Date of Patent: Nov. 10, 2026

(54) SURGICAL ROBOT SYSTEMS COMPRISING ROBOTIC TELEMANIPULATORS AND INTEGRATED LAPAROSCOPY

(71) Applicant: Distalmotion SA, Epalinges (CH)

(72) Inventors: Julien Chassot, Lechelles (CH); Michael Friedrich, Bern (CH)

(73) Assignee: Distalmotion SA, Epalinges (CH)

( * ) Notice: Subject to any disclaimer, the term of this patent is extended or adjusted under 35 U.S.C. 154(b) by 13 days.

(21) Appl. No.: 19/169,908

(22) Filed: Apr. 3, 2025

(65) Prior Publication Data

US 2025/0325337 A1 Oct. 23, 2025

Related U.S. Application Data

(63) Continuation of application No. 18/744,297, filed on Jun. 14, 2024, now Pat. No. 12,290,328, which is a (Continued)

(51) Int. Cl.
*A61B 34/37* (2016.01)
*A61B 18/14* (2006.01)

(Continued)

(52) U.S. Cl.
CPC .......... *A61B 34/37* (2016.02); *A61B 18/1442* (2013.01); *A61B 34/20* (2016.02);

(Continued)

(58) Field of Classification Search
CPC ..... A61B 34/37; A61B 18/1442; A61B 34/20; A61B 34/25; A61B 34/74; A61B 34/77;

(Continued)

(56) References Cited

U.S. PATENT DOCUMENTS 2,764,301 A 9/1956 Goertz et al.
2,771,199 A 11/1956 Jelatis (Continued)

FOREIGN PATENT DOCUMENTS

CA 2681965 A1 * 3/2003 ............ A61B 34/37
CN 101027010 A 8/2007

(Continued)

OTHER PUBLICATIONS

US 9,232,978 B2, 01/2016, Shellenberger (withdrawn)

(Continued)

*Primary Examiner* — Ashley L Fishback

(57) ABSTRACT

Surgical robot systems for remote manipulation having robotic telemanipulators are provided. The surgical robot systems are well adapted for use by the surgeon, seamlessly integrateable into the operation room, allow for a surgeon to work between the robot and the patient throughout a surgery in a sterile manner, are relatively low cost, and/or permit integrated laparoscopy. The system preferably includes a master console having a plurality of master links interconnected by a plurality of master joints, and a handle coupled to the master console for operating the telemanipulator. The system further includes a slave console operatively coupled to the master console and having a plurality of slave links interconnected by a plurality of slave joints that move responsive to movement at the master console to permit an end-effector to perform surgery.

20 Claims, 59 Drawing Sheets

Related U.S. Application Data continuation of application No. 18/057,467, filed on Nov. 21, 2022, now Pat. No. 12,161,438, which is a continuation of application No. 16/505,585, filed on Jul. 8, 2019, now Pat. No. 11,510,745, which is a continuation of application No. 16/269,383, filed on Feb. 6, 2019, now Pat. No. 10,413,374.

(60) Provisional application No. 62/788,781, filed on Jan. 5, 2019, provisional application No. 62/627,554, filed on Feb. 7, 2018.

(51) Int. Cl.

| | |
|---|---|
| ***A61B 34/00*** | (2016.01) |
| ***A61B 34/20*** | (2016.01) |
| ***A61B 34/30*** | (2016.01) |
| ***B25J 9/16*** | (2006.01) |
| *A61B 17/00* | (2006.01) |
| *A61B 90/98* | (2016.01) |
| *G16H 40/63* | (2018.01) |

(52) U.S. Cl.
CPC .............. *A61B 34/25* (2016.02); *A61B 34/74* (2016.02); *A61B 34/77* (2016.02); *B25J 9/1682* (2013.01); *A61B 2017/0046* (2013.01); *A61B 2034/302* (2016.02); *A61B 2034/305* (2016.02); *A61B 90/98* (2016.02); *G16H 40/63* (2018.01)

(58) Field of Classification Search
CPC ......... A61B 2034/302; A61B 2034/305; B25J 9/1682
See application file for complete search history.

(56) References Cited

U.S. PATENT DOCUMENTS 2,774,488 A 12/1956 Goertz et al.
2,846,084 A 8/1958 Goertz et al.
3,065,863 A 11/1962 Saunders, Jr.
3,095,096 A 6/1963 Chesley
3,212,651 A 10/1965 Specht et al.
3,261,480 A 7/1966 Haaker et al.
3,280,991 A 10/1966 Melton et al.
3,297,172 A 1/1967 Haaker et al.
3,391,801 A 7/1968 Haaker
3,425,569 A 2/1969 Haaker
3,683,747 A 8/1972 Pettit
4,221,516 A 9/1980 Haaker et al.
4,522,196 A 6/1985 Cunningham et al.
4,756,655 A 7/1988 Jameson
5,147,357 A 9/1992 Rose et al.
5,176,352 A 1/1993 Braun
5,184,601 A 2/1993 Putman
5,207,114 A 5/1993 Salisbury, Jr. et al.
5,209,747 A 5/1993 Knoepfler
5,279,309 A 1/1994 Taylor et al.
5,304,203 A 4/1994 El-Mallawany et al.
5,308,358 A 5/1994 Bond et al.
5,330,502 A 7/1994 Hassler et al.
5,368,606 A 11/1994 Marlow et al.
5,382,885 A 1/1995 Salcudean et al.
5,383,888 A 1/1995 Zvenyatsky et al.
5,484,435 A 1/1996 Fleenor et al.
5,591,119 A 1/1997 Adair
5,599,151 A 2/1997 Daum et al.
5,603,723 A 2/1997 Aranyi et al.
5,631,973 A 5/1997 Green
5,649,955 A 7/1997 Hashimoto et al.
5,649,956 A 7/1997 Jensen et al.
5,657,429 A 8/1997 Wang et al.
5,710,870 A 1/1998 Ohm et al.
5,716,352 A 2/1998 Viola et al.
5,735,874 A 4/1998 Measamer et al.
5,745,387 A 4/1998 Corby, Jr. et al.
5,779,727 A 7/1998 Orejola
5,784,542 A 7/1998 Ohm et al.
5,792,045 A 8/1998 Adair
5,797,900 A 8/1998 Madhani et al.
5,810,716 A 9/1998 Mukherjee et al.
5,810,805 A 9/1998 Sutcu et al.
5,828,813 A 10/1998 Ohm
5,876,325 A 3/1999 Mizuno et al.
5,908,436 A 6/1999 Cuschieri et al.
5,931,832 A 8/1999 Jensen
5,951,587 A 9/1999 Qureshi et al.
5,976,122 A 11/1999 Madhani et al.
6,026,701 A 2/2000 Reboulet
6,063,095 A 5/2000 Wang et al.
6,120,433 A 9/2000 Mizuno et al.
6,132,368 A 10/2000 Cooper
6,197,017 B1 3/2001 Brock et al.
6,206,903 B1 3/2001 Ramans
6,233,504 B1 5/2001 Das et al.
6,281,651 B1 8/2001 Haanpaa et al.
6,312,435 B1 11/2001 Wallace et al.
6,331,181 B1 12/2001 Tierney et al.
6,358,249 B1 3/2002 Chen et al.
6,361,534 B1 3/2002 Chen et al.
6,364,879 B1 4/2002 Chen et al.
6,371,952 B1 4/2002 Madhani et al.
6,375,610 B2 4/2002 Verschuur
6,394,998 B1 5/2002 Wallace et al.
6,435,794 B1 8/2002 Springer
6,436,107 B1 8/2002 Wang et al.
6,459,926 B1 10/2002 Nowlin et al.
6,491,701 B2 12/2002 Tierney et al.
6,554,844 B2 4/2003 Lee et al.
6,587,750 B2 7/2003 Gerbi et al.
6,594,552 B1 7/2003 Nowlin et al.
6,671,581 B2 12/2003 Niemeyer et al.
6,699,177 B1 3/2004 Wang et al.
6,723,106 B1 4/2004 Charles et al.
6,786,896 B1 9/2004 Madhani et al.
6,788,999 B2 9/2004 Green
6,799,065 B1 9/2004 Niemeyer
6,840,938 B1 1/2005 Morley et al.
6,850,817 B1 2/2005 Green
6,852,107 B2 2/2005 Wang et al.
6,879,880 B2 4/2005 Nowlin et al.
6,902,560 B1 6/2005 Morley et al.
6,913,613 B2 7/2005 Schwarz et al.
6,951,535 B2 10/2005 Ghodoussi et al.
6,991,627 B2 1/2006 Madhani et al.
6,994,708 B2 2/2006 Manzo
7,025,064 B2 4/2006 Wang et al.
7,048,745 B2 5/2006 Tierney et al.
7,083,571 B2 8/2006 Wang et al.
7,090,637 B2 8/2006 Danitz et al.
7,101,363 B2 9/2006 Nishizawa et al.
7,122,032 B2 10/2006 Shinmura et al.
7,204,836 B2 4/2007 Wagner et al.
7,232,440 B2 6/2007 Dumbauld et al.
7,241,289 B2 7/2007 Braun
7,306,597 B2 12/2007 Manzo
7,316,681 B2 1/2008 Madhani et al.
7,331,967 B2 2/2008 Lee et al.
7,338,513 B2 3/2008 Lee et al.
7,364,582 B2 4/2008 Lee
7,373,219 B2 5/2008 Nowlin et al.
7,379,790 B2 5/2008 Toth et al.
7,398,707 B2 7/2008 Morley et al.
7,481,824 B2 1/2009 Boudreaux et al.
7,549,998 B2 6/2009 Braun
7,594,912 B2 9/2009 Cooper et al.
7,608,039 B1 10/2009 Todd
7,615,002 B2 11/2009 Rothweiler et al.
7,615,067 B2 11/2009 Lee et al.
7,674,255 B2 3/2010 Braun
7,699,855 B2 4/2010 Anderson et al.
7,744,608 B2 6/2010 Lee et al.
7,756,036 B2 7/2010 Druke et al.

(56) References Cited

U.S. PATENT DOCUMENTS

| | | | |
|---|---|---|---|
| 7,819,894 | B2 | 10/2010 | Mitsuishi et al. |
| 7,824,401 | B2 | 11/2010 | Manzo et al. |
| 7,828,798 | B2 | 11/2010 | Buysse et al. |
| 7,833,156 | B2 | 11/2010 | Williams et al. |
| 7,865,266 | B2 | 1/2011 | Moll et al. |
| 7,890,211 | B2 | 2/2011 | Green |
| 7,914,521 | B2 | 3/2011 | Wang et al. |
| 7,976,458 | B2 | 7/2011 | Stefanchik et al. |
| 8,004,229 | B2 | 8/2011 | Nowlin et al. |
| 8,048,084 | B2 | 11/2011 | Schneid |
| 8,100,133 | B2 | 1/2012 | Mintz et al. |
| 8,105,320 | B2 | 1/2012 | Manzo |
| 8,114,017 | B2 | 2/2012 | Bacher |
| 8,137,263 | B2 | 3/2012 | Marescaux et al. |
| 8,142,447 | B2 | 3/2012 | Cooper et al. |
| 8,224,485 | B2 | 7/2012 | Unsworth |
| 8,246,617 | B2 | 8/2012 | Welt et al. |
| 8,267,958 | B2 | 9/2012 | Braun |
| 8,287,469 | B2 | 10/2012 | Stefanchik et al. |
| 8,292,889 | B2 | 10/2012 | Cunningham et al. |
| 8,306,656 | B1 | 11/2012 | Schaible et al. |
| 8,308,738 | B2 | 11/2012 | Nobis et al. |
| 8,332,072 | B1 | 12/2012 | Schaible et al. |
| 8,336,751 | B2 | 12/2012 | Scirica |
| 8,347,754 | B1 | 1/2013 | Veltri et al. |
| 8,353,898 | B2 | 1/2013 | Lutze et al. |
| 8,357,161 | B2 | 1/2013 | Mueller |
| 8,382,742 | B2 | 2/2013 | Hermann et al. |
| 8,388,516 | B2 | 3/2013 | Sholev |
| 8,403,832 | B2 | 3/2013 | Cunningham et al. |
| 8,414,475 | B2 | 4/2013 | Sholev |
| 8,418,904 | B2 | 4/2013 | Wenchell et al. |
| 8,419,717 | B2 | 4/2013 | Diolaiti et al. |
| 8,423,186 | B2 | 4/2013 | Itkowitz et al. |
| 8,433,389 | B2 | 4/2013 | Geiger et al. |
| 8,435,171 | B2 | 5/2013 | Sholev |
| 8,496,152 | B2 | 7/2013 | Viola |
| 8,518,024 | B2 | 8/2013 | Williams et al. |
| 8,523,900 | B2 | 9/2013 | Jinno et al. |
| 8,527,094 | B2 | 9/2013 | Kumar et al. |
| 8,540,748 | B2 | 9/2013 | Murphy et al. |
| 8,562,592 | B2 | 10/2013 | Conlon et al. |
| 8,568,444 | B2 | 10/2013 | Cunningham |
| 8,579,176 | B2 | 11/2013 | Smith et al. |
| 8,591,397 | B2 | 11/2013 | Berkelman et al. |
| 8,597,280 | B2 | 12/2013 | Cooper et al. |
| 8,602,287 | B2 | 12/2013 | Yates et al. |
| 8,603,077 | B2 | 12/2013 | Cooper et al. |
| 8,616,431 | B2 | 12/2013 | Timm et al. |
| 8,617,203 | B2 | 12/2013 | Stefanchik et al. |
| 8,644,988 | B2 | 2/2014 | Prisco et al. |
| 8,663,270 | B2 | 3/2014 | Donnigan et al. |
| 8,668,689 | B2 | 3/2014 | Dumbauld et al. |
| 8,668,702 | B2 | 3/2014 | Awtar et al. |
| 8,690,755 | B2 | 4/2014 | Sholev |
| 8,696,666 | B2 | 4/2014 | Sanai et al. |
| 8,709,000 | B2 | 4/2014 | Madhani et al. |
| 8,761,930 | B2 | 6/2014 | Nixon |
| 8,768,509 | B2 | 7/2014 | Unsworth |
| 8,792,688 | B2 | 7/2014 | Unsworth |
| 8,801,752 | B2 | 8/2014 | Fortier et al. |
| 8,816,628 | B2 | 8/2014 | Nowlin et al. |
| 8,818,560 | B2 | 8/2014 | Kishi |
| 8,821,480 | B2 | 9/2014 | Burbank |
| 8,827,135 | B2 | 9/2014 | Amid et al. |
| 8,828,046 | B2 | 9/2014 | Stefanchik et al. |
| 8,845,517 | B2 | 9/2014 | Russo |
| 8,845,622 | B2 | 9/2014 | Paik et al. |
| 8,862,268 | B2 | 10/2014 | Robinson et al. |
| 8,870,049 | B2 | 10/2014 | Amid et al. |
| 8,870,867 | B2 | 10/2014 | Walberg et al. |
| 8,887,979 | B2 | 11/2014 | Mastri et al. |
| 8,894,674 | B2 | 11/2014 | Balanev et al. |
| 8,919,348 | B2 | 12/2014 | Williams et al. |
| 8,930,027 | B2 | 1/2015 | Schaible et al. |
| 8,945,098 | B2 | 2/2015 | Seibold et al. |
| 8,961,499 | B2 | 2/2015 | Paik et al. |
| 8,961,514 | B2 | 2/2015 | Garrison |
| 8,968,187 | B2 | 3/2015 | Kleyman et al. |
| 8,989,844 | B2 | 3/2015 | Cinquin et al. |
| 8,992,564 | B2 | 3/2015 | Jaspers |
| 9,023,015 | B2 | 5/2015 | Penna |
| 9,033,998 | B1 | 5/2015 | Schaible et al. |
| 9,044,238 | B2 | 6/2015 | Orszulak |
| 9,084,606 | B2 | 7/2015 | Greep |
| 9,113,860 | B2 | 8/2015 | Viola et al. |
| 9,113,861 | B2 | 8/2015 | Martin et al. |
| 9,149,339 | B2 | 10/2015 | Unsworth |
| 9,204,939 | B2 | 12/2015 | Frimer et al. |
| 9,216,013 | B2 | 12/2015 | Scirica et al. |
| 9,295,379 | B2 | 3/2016 | Sholev |
| 9,307,894 | B2 | 4/2016 | Von Grünberg et al. |
| 9,333,040 | B2 | 5/2016 | Shellenberger et al. |
| 9,345,545 | B2 | 5/2016 | Shellenberger et al. |
| 9,360,934 | B2 | 6/2016 | Ruiz Morales et al. |
| 9,421,003 | B2 | 8/2016 | Williams et al. |
| 9,474,580 | B2 | 10/2016 | Hannaford et al. |
| 9,480,531 | B2 | 11/2016 | Von Grünberg |
| 9,492,240 | B2 | 11/2016 | Itkowitz et al. |
| 9,504,456 | B2 | 11/2016 | Frimer et al. |
| 9,504,527 | B2 | 11/2016 | Smaby et al. |
| 9,554,794 | B2 | 1/2017 | Baber et al. |
| 9,603,672 | B2 | 3/2017 | Shellenberger et al. |
| 9,669,542 | B2 | 6/2017 | Karguth et al. |
| 9,696,700 | B2 | 7/2017 | Beira et al. |
| 9,757,204 | B2 | 9/2017 | Frimer et al. |
| 9,757,206 | B2 | 9/2017 | Frimer et al. |
| 9,763,741 | B2 | 9/2017 | Alvarez et al. |
| 9,782,230 | B2 | 10/2017 | Smaby et al. |
| 9,795,282 | B2 | 10/2017 | Sholev et al. |
| 9,795,454 | B2 | 10/2017 | Seeber et al. |
| 9,825,455 | B2 | 11/2017 | Sandhu et al. |
| 9,872,737 | B2 | 1/2018 | Nixon |
| 9,877,794 | B2 | 1/2018 | Csiky |
| D816,243 | S | 4/2018 | Barber |
| 9,937,013 | B2 | 4/2018 | Frimer et al. |
| 9,943,372 | B2 | 4/2018 | Sholev et al. |
| 10,028,792 | B2 | 7/2018 | Frimer et al. |
| 10,039,609 | B2 | 8/2018 | Frimer et al. |
| 10,039,820 | B2 | 8/2018 | Coller et al. |
| 10,052,157 | B2 | 8/2018 | Frimer et al. |
| 10,064,691 | B2 | 9/2018 | Frimer et al. |
| 10,071,488 | B2 | 9/2018 | Robinson et al. |
| 10,092,164 | B2 | 10/2018 | Sholev et al. |
| 10,092,359 | B2 | 10/2018 | Beira et al. |
| 10,092,365 | B2 | 10/2018 | Seeber |
| 10,123,844 | B2 | 11/2018 | Nowlin et al. |
| 10,136,956 | B2 | 11/2018 | Seeber |
| 10,188,471 | B2 | 1/2019 | Brisson |
| 10,201,392 | B2 | 2/2019 | Frimer et al. |
| 10,265,129 | B2 | 4/2019 | Beira |
| 10,325,072 | B2 | 6/2019 | Beira et al. |
| 10,357,320 | B2 | 7/2019 | Beira |
| 10,357,324 | B2 | 7/2019 | Flatt et al. |
| 10,363,055 | B2 | 7/2019 | Beira et al. |
| 10,413,374 | B2 | 9/2019 | Chassot et al. |
| 10,510,447 | B2 | 12/2019 | Beira et al. |
| 10,548,680 | B2 | 2/2020 | Beira |
| 10,568,709 | B2 | 2/2020 | Beira |
| 10,603,123 | B2 | 3/2020 | Vakharia et al. |
| 10,646,291 | B2 | 5/2020 | Turner |
| 10,646,294 | B2 | 5/2020 | Beira |
| 10,786,272 | B2 | 9/2020 | Beira |
| 10,792,113 | B2 | 10/2020 | Cuthbertson et al. |
| 10,864,049 | B2 | 12/2020 | Beira |
| 10,864,052 | B2 | 12/2020 | Beira |
| 11,039,820 | B2 | 6/2021 | Beira |
| 11,058,503 | B2 | 7/2021 | Chassot et al. |
| 11,076,922 | B2 | 8/2021 | Beira et al. |
| 11,154,373 | B2 | 10/2021 | Abbott et al. |
| 11,173,003 | B2 | 11/2021 | Cassell et al. |
| 11,200,980 | B2 | 12/2021 | Beira et al. |
| 11,207,143 | B2 | 12/2021 | Abbott et al. |
| 11,234,782 | B2 | 2/2022 | Devengenzo et al. |

(56) References Cited

U.S. PATENT DOCUMENTS

| | | | |
|---|---|---|---|
| 11,278,364 | B2 | 3/2022 | Cooper et al. |
| 11,291,442 | B2 | 4/2022 | Wixey et al. |
| 11,324,619 | B1 | 5/2022 | Yacoby et al. |
| 11,337,716 | B2 | 5/2022 | Beira |
| 11,389,259 | B2 | 7/2022 | Dachs, II |
| 11,399,886 | B2 | 8/2022 | Kerver et al. |
| 11,432,893 | B2 | 9/2022 | Itkowitz et al. |
| 11,478,315 | B2 | 10/2022 | Beira |
| 11,490,977 | B2 | 11/2022 | Schena et al. |
| 11,490,978 | B2 | 11/2022 | Klein et al. |
| 11,510,745 | B2 | 11/2022 | Chassot et al. |
| 11,547,506 | B2 | 1/2023 | Devengenzo et al. |
| 11,564,760 | B2 | 1/2023 | Steger et al. |
| 11,571,195 | B2 | 2/2023 | Beira |
| 11,607,281 | B2 | 3/2023 | Turner |
| 11,627,948 | B2 | 4/2023 | Brisson et al. |
| 11,633,246 | B2 | 4/2023 | Cavalier et al. |
| 11,633,249 | B2 | 4/2023 | Smaby et al. |
| 11,648,076 | B2 | 5/2023 | Bailey |
| 11,659,978 | B2 | 5/2023 | Larkin et al. |
| 11,660,154 | B2 | 5/2023 | Miller et al. |
| 11,672,621 | B2 | 6/2023 | Hulford et al. |
| 11,766,303 | B2 | 9/2023 | Devengenzo et al. |
| 11,793,585 | B2 | 10/2023 | Cassell et al. |
| 11,806,016 | B2 | 11/2023 | Ragosta et al. |
| 11,826,017 | B2 | 11/2023 | Diolaiti et al. |
| 11,859,967 | B2 | 1/2024 | Diolaiti |
| 11,911,069 | B2 | 2/2024 | Lambrecht et al. |
| 11,934,594 | B2 | 3/2024 | Diolaiti et al. |
| 11,960,665 | B2 | 4/2024 | Bailey et al. |
| 11,969,889 | B2 | 4/2024 | Cooper et al. |
| 11,974,826 | B2 | 5/2024 | Steger et al. |
| 11,974,827 | B2 | 5/2024 | Gomez et al. |
| 12,016,646 | B2 | 6/2024 | Itkowitz et al. |
| 12,089,809 | B2 | 9/2024 | Larkin et al. |
| 12,161,438 | B2 | 12/2024 | Chassot et al. |
| 12,290,328 | B2 | 5/2025 | Chassot et al. |
| 12,329,481 | B2 | 6/2025 | Beira |
| 2001/0013764 | A1 | 8/2001 | Blumenkranz et al. |
| 2001/0031983 | A1 | 10/2001 | Brock et al. |
| 2002/0040217 | A1 | 4/2002 | Jinno |
| 2002/0049367 | A1 | 4/2002 | Irion et al. |
| 2002/0058929 | A1 | 5/2002 | Green |
| 2002/0072736 | A1 | 6/2002 | Tierney et al. |
| 2002/0082612 | A1 | 6/2002 | Moll et al. |
| 2003/0013949 | A1 | 1/2003 | Moll et al. |
| 2003/0060927 | A1 | 3/2003 | Gerbi et al. |
| 2003/0155747 | A1 | 8/2003 | Bridges |
| 2003/0208186 | A1 | 11/2003 | Moreyra |
| 2003/0216715 | A1 | 11/2003 | Moll et al. |
| 2004/0049205 | A1 | 3/2004 | Lee et al. |
| 2004/0116906 | A1 | 6/2004 | Lipow |
| 2004/0236316 | A1 | 11/2004 | Danitz et al. |
| 2004/0253079 | A1 | 12/2004 | Sanchez |
| 2005/0096502 | A1 | 5/2005 | Khalili |
| 2005/0204851 | A1 | 9/2005 | Morley et al. |
| 2005/0240078 | A1 | 10/2005 | Kwon et al. |
| 2006/0043698 | A1 | 3/2006 | Bridges |
| 2006/0079884 | A1 | 4/2006 | Manzo et al. |
| 2006/0178559 | A1 | 8/2006 | Kumar et al. |
| 2006/0183975 | A1 | 8/2006 | Saadat et al. |
| 2006/0219065 | A1 | 10/2006 | Jinno et al. |
| 2006/0235436 | A1 | 10/2006 | Anderson et al. |
| 2006/0253109 | A1 | 11/2006 | Chu |
| 2007/0088340 | A1 | 4/2007 | Brock et al. |
| 2007/0137371 | A1 | 6/2007 | Devengenzo et al. |
| 2007/0142969 | A1 | 6/2007 | Devengenzo et al. |
| 2007/0156123 | A1 | 7/2007 | Moll et al. |
| 2007/0208375 | A1 | 9/2007 | Nishizawa et al. |
| 2007/0299387 | A1 | 12/2007 | Williams et al. |
| 2008/0035857 | A1 | 2/2008 | Struye et al. |
| 2008/0039255 | A1 | 2/2008 | Jinno et al. |
| 2008/0046122 | A1 | 2/2008 | Manzo et al. |
| 2008/0058776 | A1 | 3/2008 | Jo et al. |
| 2008/0071208 | A1 | 3/2008 | Voegele et al. |
| 2008/0103492 | A1 | 5/2008 | Morley et al. |
| 2008/0177285 | A1 | 7/2008 | Brock et al. |
| 2008/0243106 | A1 | 10/2008 | Coe et al. |
| 2008/0287926 | A1 | 11/2008 | Abou El Kheir |
| 2008/0314181 | A1 | 12/2008 | Schena |
| 2009/0030449 | A1 | 1/2009 | Kawai et al. |
| 2009/0036902 | A1 | 2/2009 | DiMaio et al. |
| 2009/0088775 | A1 | 4/2009 | Swarup et al. |
| 2009/0192522 | A1 | 7/2009 | Blumenkranz |
| 2009/0198253 | A1 | 8/2009 | Omori |
| 2009/0216248 | A1 | 8/2009 | Uenohara et al. |
| 2009/0216249 | A1 | 8/2009 | Jinno et al. |
| 2009/0247821 | A1 | 10/2009 | Rogers |
| 2009/0248039 | A1 | 10/2009 | Cooper et al. |
| 2009/0275994 | A1 | 11/2009 | Phan et al. |
| 2009/0299141 | A1 | 12/2009 | Downey et al. |
| 2009/0326552 | A1 | 12/2009 | Diolaiti |
| 2010/0004508 | A1 | 1/2010 | Naito et al. |
| 2010/0011900 | A1 | 1/2010 | Burbank |
| 2010/0023025 | A1 | 1/2010 | Zeiner et al. |
| 2010/0082041 | A1 | 4/2010 | Prisco |
| 2010/0094130 | A1 | 4/2010 | Ninomiya et al. |
| 2010/0121347 | A1 | 5/2010 | Jaspers |
| 2010/0160929 | A1 | 6/2010 | Rogers et al. |
| 2010/0160940 | A1 | 6/2010 | Lutze et al. |
| 2010/0170519 | A1 | 7/2010 | Romo et al. |
| 2010/0225209 | A1 | 9/2010 | Goldberg et al. |
| 2010/0234857 | A1 | 9/2010 | Itkowitz et al. |
| 2010/0262162 | A1 | 10/2010 | Omori |
| 2010/0286712 | A1 | 11/2010 | Won et al. |
| 2010/0305595 | A1 | 12/2010 | Hermann |
| 2010/0318099 | A1 | 12/2010 | Itkowitz et al. |
| 2010/0318101 | A1 | 12/2010 | Choi |
| 2010/0324551 | A1 | 12/2010 | Gerhardt |
| 2010/0331859 | A1 | 12/2010 | Omori |
| 2011/0082462 | A1 | 4/2011 | Suarez et al. |
| 2011/0087236 | A1 | 4/2011 | Stokes et al. |
| 2011/0087238 | A1 | 4/2011 | Wang et al. |
| 2011/0152881 | A1 | 6/2011 | Conner et al. |
| 2011/0213346 | A1 | 9/2011 | Morley et al. |
| 2011/0230867 | A1 | 9/2011 | Hirschfeld et al. |
| 2011/0275901 | A1 | 11/2011 | Shelton, IV |
| 2011/0276084 | A1 | 11/2011 | Shelton, IV |
| 2011/0282491 | A1 | 11/2011 | Prisco et al. |
| 2011/0290854 | A1 | 12/2011 | Timm et al. |
| 2011/0301419 | A1 | 12/2011 | Craft et al. |
| 2012/0010628 | A1 | 1/2012 | Cooper et al. |
| 2012/0027762 | A1 | 2/2012 | Schofield |
| 2012/0031114 | A1 | 2/2012 | Mueller et al. |
| 2012/0049623 | A1 | 3/2012 | Nakayama |
| 2012/0080040 | A1 | 4/2012 | Skora et al. |
| 2012/0095298 | A1 | 4/2012 | Stefanchik et al. |
| 2012/0116163 | A1 | 5/2012 | Lutze et al. |
| 2012/0132018 | A1 | 5/2012 | Tang et al. |
| 2012/0143173 | A1 | 6/2012 | Steege et al. |
| 2012/0158014 | A1 | 6/2012 | Stefanchik et al. |
| 2012/0191245 | A1 | 7/2012 | Fudaba et al. |
| 2012/0209292 | A1 | 8/2012 | Devengenzo et al. |
| 2012/0232339 | A1 | 9/2012 | Csiky |
| 2012/0253326 | A1 | 10/2012 | Kleyman |
| 2012/0277762 | A1 | 11/2012 | Lathrop et al. |
| 2012/0283745 | A1 | 11/2012 | Goldberg et al. |
| 2012/0289973 | A1 | 11/2012 | Prisco et al. |
| 2012/0289974 | A1 | 11/2012 | Rogers et al. |
| 2012/0296341 | A1 | 11/2012 | Seibold et al. |
| 2013/0123805 | A1 | 5/2013 | Park et al. |
| 2013/0144274 | A1 | 6/2013 | Stefanchik et al. |
| 2013/0172713 | A1 | 7/2013 | Kirschenman |
| 2013/0172906 | A1 | 7/2013 | Olson et al. |
| 2013/0245643 | A1 | 9/2013 | Woodard, Jr. et al. |
| 2013/0245647 | A1 | 9/2013 | Martin et al. |
| 2013/0282027 | A1 | 10/2013 | Woodard, Jr. et al. |
| 2013/0303408 | A1 | 11/2013 | Indermuhle |
| 2013/0304070 | A1 | 11/2013 | Nelson et al. |
| 2013/0304083 | A1 | 11/2013 | Kaercher et al. |
| 2013/0304084 | A1 | 11/2013 | Beira et al. |
| 2014/0005681 | A1 | 1/2014 | Gee et al. |
| 2014/0018447 | A1 | 1/2014 | McGovern et al. |
| 2014/0018780 | A1 | 1/2014 | Hirscheld |

(56) References Cited

U.S. PATENT DOCUMENTS

| | | | |
|---|---|---|---|
| 2014/0018960 A1 | 1/2014 | Itkowitz |
| 2014/0039527 A1 | 2/2014 | Avelar et al. |
| 2014/0052152 A1 | 2/2014 | Au et al. |
| 2014/0076088 A1 | 3/2014 | Berkelman et al. |
| 2014/0114481 A1 | 4/2014 | Ogawa et al. |
| 2014/0135794 A1 | 5/2014 | Cau |
| 2014/0142595 A1 | 5/2014 | Awtar et al. |
| 2014/0166023 A1 | 6/2014 | Kishi |
| 2014/0180308 A1 | 6/2014 | Von Grünberg |
| 2014/0188091 A1 | 7/2014 | Vidal et al. |
| 2014/0188159 A1 | 7/2014 | Steege |
| 2014/0195010 A1 | 7/2014 | Beira et al. |
| 2014/0200561 A1 | 7/2014 | Ingmanson et al. |
| 2014/0207150 A1 | 7/2014 | Rosa et al. |
| 2014/0229007 A1 | 8/2014 | Kishi |
| 2014/0230595 A1 | 8/2014 | Butt et al. |
| 2014/0249546 A1 | 9/2014 | Shvartsberg et al. |
| 2014/0263541 A1 | 9/2014 | Leimbach et al. |
| 2014/0263553 A1 | 9/2014 | Leimbach et al. |
| 2014/0276950 A1 | 9/2014 | Smaby et al. |
| 2014/0276951 A1 | 9/2014 | Hourtash et al. |
| 2014/0276956 A1 | 9/2014 | Crainich et al. |
| 2014/0277017 A1 | 9/2014 | Leimbach et al. |
| 2014/0277203 A1 | 9/2014 | Atoulikian et al. |
| 2014/0340796 A1 | 11/2014 | Sandhu et al. |
| 2014/0350570 A1 | 11/2014 | Lee |
| 2015/0057499 A1 | 2/2015 | Erden et al. |
| 2015/0057702 A1 | 2/2015 | Edmondson et al. |
| 2015/0060517 A1 | 3/2015 | Williams |
| 2015/0066018 A1 | 3/2015 | Doll et al. |
| 2015/0105821 A1 | 4/2015 | Ward et al. |
| 2015/0113933 A1 | 4/2015 | Markt |
| 2015/0142018 A1 | 5/2015 | Sniffin et al. |
| 2015/0150575 A1 | 6/2015 | Hartoumbekis et al. |
| 2015/0173840 A1 | 6/2015 | Lohmeier |
| 2015/0230869 A1 | 8/2015 | Shim et al. |
| 2015/0250547 A1 | 9/2015 | Fukushima et al. |
| 2015/0265355 A1 | 9/2015 | Prestel et al. |
| 2016/0022365 A1 | 1/2016 | Jensen et al. |
| 2016/0051274 A1 | 2/2016 | Howell et al. |
| 2016/0151115 A1 | 6/2016 | Karguth et al. |
| 2016/0220314 A1 | 8/2016 | Huelman et al. |
| 2016/0270867 A1 | 9/2016 | Scholan |
| 2016/0302876 A1 | 10/2016 | Teichtmann |
| 2016/0303743 A1 | 10/2016 | Rockrohr |
| 2016/0346053 A1 | 12/2016 | Beira |
| 2016/0374766 A1 | 12/2016 | Schuh |
| 2017/0007335 A1 | 1/2017 | Popovic et al. |
| 2017/0020615 A1 | 1/2017 | Koenig et al. |
| 2017/0065364 A1 | 3/2017 | Schuh et al. |
| 2017/0086932 A1 | 3/2017 | Auld et al. |
| 2017/0189130 A1 | 7/2017 | Weir |
| 2017/0215976 A1 | 8/2017 | Nowlin et al. |
| 2017/0245954 A1 | 8/2017 | Beira |
| 2017/0252096 A1 | 9/2017 | Felder et al. |
| 2017/0265951 A1 | 9/2017 | Grover et al. |
| 2017/0273749 A1 | 9/2017 | Grover et al. |
| 2017/0308667 A1 | 10/2017 | Beira et al. |
| 2017/0360522 A1 | 12/2017 | Beira |
| 2017/0367778 A1 | 12/2017 | Beira |
| 2018/0000472 A1 | 1/2018 | Beira |
| 2018/0000544 A1 | 1/2018 | Beira |
| 2018/0000550 A1 | 1/2018 | Beira |
| 2018/0008358 A1 | 1/2018 | Kostrzewski et al. |
| 2018/0028269 A1 | 2/2018 | Morel et al. |
| 2018/0055583 A1 | 3/2018 | Schuh et al. |
| 2018/0078439 A1 | 3/2018 | Cagle et al. |
| 2018/0110576 A1 | 4/2018 | Kopp |
| 2018/0125519 A1 | 5/2018 | Beira et al. |
| 2018/0125592 A1 | 5/2018 | Beira |
| 2018/0168760 A1 | 6/2018 | Koch, Jr. et al. |
| 2018/0214223 A1 | 8/2018 | Turner |
| 2018/0242991 A1 | 8/2018 | Beira |
| 2018/0296286 A1 | 10/2018 | Peine et al. |
| 2018/0353251 A1 | 12/2018 | Cuthbertson et al. |
| 2018/0353252 A1 | 12/2018 | Chassot et al. |
| 2018/0360548 A1 | 12/2018 | Marshall et al. |
| 2019/0029770 A1 | 1/2019 | Bailey |
| 2019/0133698 A1 | 5/2019 | Beira et al. |
| 2019/0239968 A1 | 8/2019 | Beira |
| 2019/0314096 A1 | 10/2019 | Diolaiti et al. |
| 2019/0328473 A1 | 10/2019 | Chassot et al. |
| 2019/0380795 A1 | 12/2019 | Tsao et al. |
| 2020/0105412 A1 | 4/2020 | Beira et al. |
| 2020/0246085 A1 | 8/2020 | Noonan et al. |
| 2020/0268464 A1 | 8/2020 | Beira |
| 2020/0315721 A1 | 10/2020 | Rabindran et al. |
| 2021/0106348 A1 | 4/2021 | Beira |
| 2021/0330407 A1 | 10/2021 | Chassot et al. |
| 2021/0330408 A1 | 10/2021 | Chassot et al. |
| 2021/0369360 A1 | 12/2021 | Beira et al. |
| 2022/0280179 A1 | 9/2022 | Beira |
| 2023/0054176 A1 | 2/2023 | Beira |
| 2023/0082915 A1 | 3/2023 | Chassot et al. |
| 2023/0125213 A1 | 4/2023 | Chassot et al. |
| 2024/0000525 A1 | 1/2024 | Cassell et al. |
| 2024/0115334 A1 | 4/2024 | Beira |
| 2024/0335246 A1 | 10/2024 | Chassot et al. |

FOREIGN PATENT DOCUMENTS

| | | | |
|---|---|---|---|
| CN | 101584594 | A | 11/2009 |
| CN | 101637402 | A | 2/2010 |
| CN | 101732093 | A | 6/2010 |
| CN | 103717355 | A | 4/2014 |
| CN | 107666878 | A | 2/2018 |
| DE | 4303311 | A1 | 8/1994 |
| DE | 19652792 | C2 | 5/1999 |
| DE | 10314827 | B3 | 4/2004 |
| DE | 10314828 | B3 | 7/2004 |
| DE | 102012222755 | A1 | 6/2014 |
| DE | 102014205036 | A1 | 9/2015 |
| DE | 102014205159 | A1 | 9/2015 |
| EP | 0085609 | B1 | 7/1987 |
| EP | 0595291 | A1 | 5/1994 |
| EP | 0621009 | A1 | 10/1994 |
| EP | 0677275 | A2 | 10/1995 |
| EP | 0776739 | A2 | 6/1997 |
| EP | 1254642 | A1 | 11/2002 |
| EP | 1279371 | B1 | 12/2004 |
| EP | 1886630 | A2 | 2/2008 |
| EP | 1889579 | A2 | 2/2008 |
| EP | 1889583 | A1 | 2/2008 |
| EP | 2058090 | A2 | 5/2009 |
| EP | 1977677 | B1 | 8/2009 |
| EP | 2095778 | A1 | 9/2009 |
| EP | 1889583 | B1 | 4/2011 |
| EP | 2377477 | B1 | 5/2012 |
| EP | 2473119 | A2 | 7/2012 |
| EP | 2305144 | B1 | 10/2012 |
| EP | 2044893 | B1 | 7/2013 |
| EP | 2653110 | A1 | 10/2013 |
| EP | 2679192 | A2 | 1/2014 |
| EP | 2736680 | A2 | 6/2014 |
| EP | 2777561 | A1 | 9/2014 |
| EP | 2783643 | A1 | 10/2014 |
| EP | 2837340 | A1 | 2/2015 |
| EP | 2837354 | A1 | 2/2015 |
| EP | 2554131 | B1 | 8/2015 |
| EP | 2777561 | B1 | 10/2015 |
| EP | 2979657 | A1 | 2/2016 |
| EP | 2837340 | B1 | 10/2016 |
| EP | 3111879 | A1 | 1/2017 |
| EP | 2783643 | B1 | 1/2019 |
| GB | 834244 | A | 5/1960 |
| GB | 969899 | A | 9/1964 |
| JP | H06122299 | A | 5/1994 |
| JP | 2001504395 | A | 4/2001 |
| JP | 2004041580 | A | 2/2004 |
| JP | 2007061946 | A | 3/2007 |
| JP | 2007290096 | A | 11/2007 |
| JP | 2008104620 | A | 5/2008 |
| JP | 2009018027 | A | 1/2009 |
| JP | 2011194163 | A | 10/2011 |

(56) References Cited

FOREIGN PATENT DOCUMENTS

| | | | | |
|---|---|---|---|---|
| JP | 2013035117 | A | 2/2013 | |
| JP | 2015024036 | A | 2/2015 | |
| JP | 2015128681 | A | 7/2015 | |
| JP | 2015150425 | A | 8/2015 | |
| JP | 2015526115 | A | 9/2015 | |
| JP | 2016519585 | A | 7/2016 | |
| KR | 20110032444 | A | 3/2011 | |
| KR | 20130031403 | A | 3/2013 | |
| KR | 101645969 | B1 | 8/2016 | |
| SU | 722754 | A1 | 3/1980 | |
| WO | WO-8200611 | A1 | 3/1982 | |
| WO | WO-9639944 | A1 | 12/1996 | |
| WO | WO-9743942 | A1 | 11/1997 | |
| WO | WO-9825666 | A1 | 6/1998 | |
| WO | WO-0134017 | A2 | 5/2001 | |
| WO | WO-0197717 | A1 | 12/2001 | |
| WO | WO-03067341 | A2 | 8/2003 | |
| WO | WO-03086219 | A2 | 10/2003 | |
| WO | WO-2004052171 | A2 | 6/2004 | |
| WO | WO-2005009482 | A2 | 2/2005 | |
| WO | WO-2005046500 | A1 | 5/2005 | |
| WO | WO-2006086663 | A2 | 8/2006 | |
| WO | WO-2007133065 | A1 | 11/2007 | |
| WO | WO-2007146987 | A2 | 12/2007 | |
| WO | WO-2008070556 | A1 | 6/2008 | |
| WO | WO-2008130235 | A2 | 10/2008 | |
| WO | WO-2009091497 | A2 | 7/2009 | |
| WO | WO-2009095893 | A2 | 8/2009 | |
| WO | WO-2009145572 | A2 | 12/2009 | |
| WO | WO-2009157719 | A2 | 12/2009 | |
| WO | WO-2010019001 | A2 | 2/2010 | |
| WO | WO-2010030114 | A2 | 3/2010 | |
| WO | WO-2010050771 | A2 | 5/2010 | |
| WO | WO-2010083480 | A2 | 7/2010 | |
| WO | WO-2010096580 | A1 | 8/2010 | |
| WO | WO-2010130817 | A1 | 11/2010 | |
| WO | WO-2011025818 | A1 | 3/2011 | |
| WO | WO-2011027183 | A2 | 3/2011 | |
| WO | WO-2011123669 | A1 | 10/2011 | |
| WO | WO-2012020386 | A1 | 2/2012 | |
| WO | WO-2012049623 | A1 | 4/2012 | |
| WO | WO-2013007784 | A1 | 1/2013 | |
| WO | WO-2013014621 | A2 | 1/2013 | |
| WO | WO-2013018897 | A1 * | 2/2013 | ............ A61B 17/29 |
| WO | WO-2013018934 | A1 | 2/2013 | |
| WO | WO-2014012780 | A1 | 1/2014 | |
| WO | WO-2014018447 | A1 | 1/2014 | |
| WO | WO-2014067804 | A1 | 5/2014 | |
| WO | WO-2014094716 | A1 | 6/2014 | |
| WO | WO-2014094717 | A1 | 6/2014 | |
| WO | WO-2014094718 | A1 | 6/2014 | |
| WO | WO-2014094719 | A1 | 6/2014 | |
| WO | WO-2014114551 | A1 | 7/2014 | |
| WO | WO-2014139023 | A1 | 9/2014 | |
| WO | WO-2014145148 | A2 | 9/2014 | |
| WO | WO-2014156221 | A1 | 10/2014 | |
| WO | WO-2014166573 | A1 | 10/2014 | |
| WO | WO-2014201010 | A1 | 12/2014 | |
| WO | WO-2014201538 | A1 | 12/2014 | |
| WO | WO-2015081946 | A1 | 6/2015 | |
| WO | WO-2015081947 | A1 | 6/2015 | |
| WO | WO-2015088647 | A1 | 6/2015 | |
| WO | WO-2015088655 | A1 | 6/2015 | |
| WO | WO-2015111475 | A1 | 7/2015 | |
| WO | WO-2015113933 | A1 | 8/2015 | |
| WO | WO-2015129383 | A1 | 9/2015 | |
| WO | WO-2015139674 | A1 | 9/2015 | |
| WO | WO-2015175200 | A1 | 11/2015 | |
| WO | WO-2016030767 | A1 | 3/2016 | |
| WO | WO-2016083189 | A1 | 6/2016 | |
| WO | WO-2016097861 | A1 | 6/2016 | |
| WO | WO-2016097864 | A2 | 6/2016 | |
| WO | WO-2016097868 | A1 | 6/2016 | |
| WO | WO-2016097871 | A1 | 6/2016 | |
| WO | WO-2016097873 | A2 | 6/2016 | |
| WO | WO-2016154173 | A1 | 9/2016 | |
| WO | WO-2016162751 | A1 | 10/2016 | |
| WO | WO-2016162752 | A1 | 10/2016 | |
| WO | WO-2016183054 | A1 | 11/2016 | |
| WO | WO-2016189284 | A1 | 12/2016 | |
| WO | WO-2016209891 | A1 | 12/2016 | |
| WO | WO-2017015599 | A1 | 1/2017 | |
| WO | WO-2017037532 | A1 | 3/2017 | |
| WO | WO-2017064301 | A1 | 4/2017 | |
| WO | WO-2017064303 | A1 | 4/2017 | |
| WO | WO-2017064305 | A1 | 4/2017 | |
| WO | WO-2017064306 | A1 | 4/2017 | |
| WO | WO-2017134077 | A1 | 8/2017 | |
| WO | WO-2017220978 | A1 | 12/2017 | |
| WO | WO-2018142112 | A1 | 8/2018 | |
| WO | WO-2018162921 | A1 | 9/2018 | |
| WO | WO-2018207136 | A1 | 11/2018 | |
| WO | WO-2019099346 | A2 | 5/2019 | |
| WO | WO-2019155383 | A1 | 8/2019 | |
| WO | WO-2020131304 | A1 | 6/2020 | |
| WO | WO-2020141487 | A2 | 7/2020 | |
| WO | WO-2020263870 | A1 | 12/2020 | |
| WO | WO-2023073565 | A1 | 5/2023 | |

OTHER PUBLICATIONS

Abbott, et al., Design of an Endoluminal Notes Robotic System, IEEE/RSJ International Conference on Intelligent Robots and Systems, 2007, San Diego, CA (pp. 410-416).

Aesculap Surgical Technologies, Aesculap.RTM. Caiman™, Advanced Bipolar Seal and Cut Technology Brochure, 6 pages (retrieved Aug. 31, 2015).

Arata, et al., Development of a dexterous minimally-invasive surgical system with augmented force feedback capability, IEEE/RSJ International Conference on Intelligent Robots and Systems, 2005 (pp. 3207-3212).

Cavusoglu, et al., Laparoscopic Telesurgical Workstation, IEEE Transactions on Robotics and Automation, (15)4:728-739 (1999).

Charles, et al., Dexterity-enhanced Telerobotic Microsurgery, 8th International Conference Advanced Robotics, pp. 5-10 (1997).

Communication Relating to the Results of the Partial International Search dated May 28, 2019 in Int'I PCT Patent Appl. Serial No. PCT/IB2019/050961, 13 pages.

Dachs, et al., Novel Surgical Robot Design: Minimizing the Operating Envelope With in the Sterile Field, 28th International Conference, IEEE Engineering in Medicine Biology Society, 2006, New York (pp. 1505-1508).

Dario, et al., "Novel Mechatronic Tool for Computer-Assisted Arthroscopy," IEEE Transactions on Information Technology in Biomedicine, 4(1):15-29 (Mar. 2000).

Extended European Search Report dated Mar. 18, 2020 in EP Patent Appl. Serial No. 19213231.4, 7 pages.

Focacci, et al., Lightweight Hand-held Robot for Laparoscopic Surgery, IEEE International Conference on Robotics & Automation, Rome, Italy, pp. 599-604 (2007).

Guthart, et al., The Intuitive™. Telesurgery System: Overview and Application, IEEE International Conference on Robotics & Automation, San Francisco, CA, 2000 (pp. 618-621).

Ikuta, et al., Development of Remote Microsurgery Robot and New Surgical Procedure for Deep and Narrow Space, IEEE International Conference on Robotics & Automation, Taipei, Taiwan, 2003 (pp. 1103-1108).

Ikuta, et al., Hyper Redundant Miniature Manipulator 'Hyper Finger' for Remote Minimally Invasive Surgery in Deep Area, IEEE International Conference on Robotics & Automation, Taipei, Taiwan, 2003 (pp. 1098-1102).

International Search Report & Written Opinion dated Feb. 2, 2017 in Int'l PCT Patent Appl. Serial No. PCT/IB2016/001286, 10 pages.

International Search Report & Written Opinion dated Feb. 17, 2016 in Int'l PCT Patent Appl. Serial No. PCT/IB2015/002095, 9 pages.

International Search Report & Written Opinion dated May 23, 2016 in Int'l PCT Patent Appl Serial No. PCT/IB2015/002524, 8 pages.

International Search Report & Written Opinion dated Jul. 7, 2020 in Int'l. PCT Patent Appl. Serial No. PCTIB2020050039, 20 pages.

(56) References Cited

OTHER PUBLICATIONS

International Search Report & Written Opinion dated Jul. 10, 2018 in Int'l PCT Patent Appl. Serial No. PCT/IB2018/053272, 11 pages.
International Search Report & Written Opinion dated Jul. 23, 2019 in Int'l PCT Patent Appl. No. PCT/IB2019/050961, 17 pages.
International Search Report & Written Opinion dated Jan. 18, 2013 in Int'l PCT Patent Appl Serial No. PCT/IB2012/053786, 24 pages.
International Search Report & Written Opinion dated Mar. 23, 2012 in Int'l PCT Patent Appl Serial No. PCT/IB2011/054476, 10 pages.
International Search Report & Written Opinion dated Mar. 30, 2015 in Int'l PCT Patent Appl Serial No. PCT/EP2015/051473, 9 pages.
International Search Report & Written Opinion dated Apr. 26, 2016 in Int'l PCT Patent Appl Serial No. PCT/IB2015/002512, 12 pages.
International Search Report & Written Opinion dated May 24, 2016 in Int'I PCT Patent Appl Serial No. PCT/IB2015/002487, 10 pages.
International Search Report & Written Opinion dated Jun. 10, 2016 in Int'l PCT Patent Appl Serial No. PCT/IB2015/002533, 11 pages.
International Search Report & Written Opinion dated Jun. 13, 2016 in Int'l PCT Patent Appl Serial No. PCT/IB2015/002493, 10 pages.
International Search Report & Written Opinion dated Aug. 25, 2016 in Int'l PCT Patent Appl Serial No. PCT/IB2016/000542, 8 pages.
International Search Report & Written Opinion dated Sep. 2, 2016 in Int'l PCT Patent Appl Serial No. PCT/IB2016/000543, 12 pages.
Ishii, et al., Development of a New Bending Mechanism and Its Application to Robotic Forceps Manipulator, IEEE International Conference on Robotics & Automation, Rome, Italy, 2007 (pp. 238-243).
Kobayashi, et al., Small Occupancy Robotic Mechanisms for Endoscopic Surgery, International Conference on Medical Image Computing and Computer assisted Interventions, 2002, (pp. 75-82).
Lang, et al., Intra-operative robotics: NeuroArm., Acta Neurochir Suppl, 109:231-236 (2011).
Mayer, et al., The Endo[PA]R System for Minimally Invasive Robotic Surgery, IEEE/RSJ International Conference on Intelligent Robots and Systems, Sendai, Japan, 2004 (pp. 3637-3642).
Mitsuishi, et al., Development of a Remote Minimally Invasive Surgical System with Operational Environment Transmission Capability, IEEE International Conference on Robotics & Automation, Taipei, Taiwan, 2003, (pp. 2663-2670).
Mitsuishi, et al., Master-Slave Robotic Platform and its Feasibility Study for Micro-Neurosurgery, Int. J. Med. Robot., 9(2):180-9 (2013).
Morita, et al., Microsurgical Robotic System for the Deep Surgical Field: development of a Prototype and Feasibility Studies in Animal and Cadaveric Models, J. Neurosurg., 103(2):320-7 (2005).
Nakamura, et al., Multi-DOF Forceps Manipulator System for Laparoscopic Surgery-Mechanism miniaturized & Evaluation of New Interface, 4th International Conference on Medical Image Computing and Computer Assisted Interventions (MICCAI2001), 2001 (pp. 606-613).
Non-Final Office Action for U.S. Appl. No. 18/057,467 dated Mar. 20, 2024, 7 pages.
Notice of Allowance for U.S. Appl. No. 18/057,467 mailed Aug. 8, 2024, 7 pages.
Notice of Allowance for U.S. Appl. No. 18/744,297 mailed Jan. 3, 2025, 8 pages.
Notice of Allowance for U.S. Appl. No. 18/744,297 mailed Sep. 11, 2024, 8 pages.
Peirs, et al., "Design of an Advanced Tool Guiding System for Robotic Surgery," IEEE International Conference on Robotics & Automation, Taipei, Taiwan, 2003, (pp. 2651-2656).
Salle, et al., Optimal Design of High Dexterity Modular MIS Instrument for Coronary Artery Bypass Grafting, IEEE International Conference on Robotics & Automation, New Orleans, LA, 2004, (pp. 1276-1281).
Seibold, et al., Prototype of Instrument for Minimally Invasive Surgery with 6-Axis Force Sensing Capability, IEEE International Conference on Robotics & Automation, Barcelona, Spain, 2005, (pp. 496-501).
Simaan, et al., Dexterous System for Laryngeal Surgery: Multi-Backbone Bending Snake-like Slaves for Teleoperated Dexterous Surgical Tool Manipulation, IEEE International Conference on Robotics & Automation, New Orleans, LA, 2004 (pp. 351-357).
Stryker™, Endoscopy, Take a Look Around, Ideal Eyes.TM. FFD122 HD, Articulating Laparoscope Brochure, 2 pages (2009).
Swiss Search Report dated Jun. 4, 2012 in Swiss Patent Application No. CH 00702/12, 2 pages.
Tavakoli, et al., Force Reflective Master-Slave System for Minimally Invasive Surgery, IEEE/RSJ International Conference on Intelligent Robots and Systems, Las Vegas, NV, 2003, (pp. 3077-3082).
Taylor, et al., Steady-Hand Robotic System for Microsurgical Augmentation, The International Journal of Robotics Research, 18(12):1201-1210 (1999).
www.cttc.co/technologies/maestro-non-robotic-dexterous-laproscopic-instrum-ent-writsproviding-seven-degrees, Maestro: Non-Robotic Dexterous Laproscopic Instrument With a Wrist Providing Seven Degrees of Freedom, accessed Nov. 12, 2015, 4 pages.
Yamashita, et al., Development of Endoscopic Forceps Manipulator Using Multi-Slider Linkage Mechanisms, The 1st Asian Symposium on Computer Aided Surgery-Robotic and Image-Guided Surgery, Ibaraki, Japan, 4 pages (2005).
Zeus, Robotic Surgical System, available at http://allaboutroboticsurgery.com/zeusrobot.html. (2017) 4 pages.

* cited by examiner

SURGICAL ROBOT SYSTEMS COMPRISING ROBOTIC TELEMANIPULATORS AND INTEGRATED LAPAROSCOPY

CROSS-REFERENCE TO RELATED APPLICATIONS

This application is a continuation of U.S. patent application Ser. No. 18/744,297, filed Jun. 14, 2024, now U.S. Pat. No. 12,290,328, which is a continuation of U.S. patent application Ser. No. 18/057,467, filed Nov. 21, 2022, now U.S. Pat. No. 12,161,438, which is a continuation of U.S. patent application Ser. No. 16/505,585, filed Jul. 8, 2019, now U.S. Pat. No. 11,510,745, which is a continuation of U.S. patent application Ser. No. 16/269,383, filed Feb. 6, 2019, now U.S. Pat. No. 10,413,374, which claims the benefit of priority of U.S. Provisional Patent Application No. 62/788,781, filed Jan. 5, 2019, and U.S. Provisional Patent Application No. 62/627,554, filed Feb. 7, 2018, the entire contents of each of which are incorporated herein by reference.

FIELD OF USE

This application generally relates to remotely actuated surgical robot systems having robotic telemanipulators.

BACKGROUND

Numerous environments and applications call for remote actuation with teleoperated surgical devices. These applications include the ability to perform fine manipulation, to manipulate in confined spaces, manipulate in dangerous or contaminated environments, in clean-room or sterile environments and in surgical environments, whether open field or minimally invasive. While these applications vary, along with parameters such as precise tolerances and the level of skill of the end user, each demands many of the same features from a teleoperated system, such as the ability to carry out dexterous manipulation with high precision.

Surgical applications are discussed in the following disclosure in more detail as exemplary of applications for a teleoperated device system where known devices exist but significant shortcomings are evident in previously-known systems and methods.

Open surgery is still the preferred method for many surgical procedures. It has been used by the medical community for many decades and typically required making long incisions in the abdomen or other area of the body, through which traditional surgical tools are inserted. Due to such incisions, this extremely invasive approach results in substantial blood loss during surgery and, typically, long and painful recuperation periods in a hospital setting.

Laparoscopy, a minimally invasive technique, was developed to overcome some of the disadvantages of open surgery. Instead of large through-wall incisions, several small openings are made in the patient through which long and thin surgical instruments and endoscopic cameras are inserted. The minimally invasive nature of laparoscopic procedures reduces blood loss and pain and shortens hospital stays. When performed by experienced surgeons, a laparoscopic technique can attain clinical outcomes similar to open surgery. However, despite the above-mentioned advantages, laparoscopy requires a high degree of skill to successfully manipulate the rigid and long instrumentation used in such procedures. Typically, the entry incision acts as a point of rotation, decreasing the freedom for positioning and orientating the instruments inside the patient. The movements of the surgeon's hand about this incision point are inverted and scaled-up relative to the instrument tip ("fulcrum effect"), which reduces dexterity and sensitivity and magnifies any tremors of the surgeon's hands. In addition, the long and straight instruments force the surgeon to work in an uncomfortable posture for hands, arms and body, which can be tremendously tiring during a prolonged procedure. Therefore, due to these drawbacks of laparoscopic instrumentation, minimally invasive techniques are mainly limited to use in simple surgeries, while only a small minority of surgeons is able to use such instrumentation and methods in complex procedures.

To overcome the foregoing limitations of previously-known systems, surgical robotic systems were developed to provide an easier-to-use approach to complex minimally invasive surgeries. By means of a computerized robotic interface, those systems enable the performance of remote laparoscopy where the surgeon sits at a console manipulating two master manipulators to perform the operation through several small incisions. Like laparoscopy, the robotic approach is also minimally invasive, providing the above-mentioned advantages over open surgery with respect to reduced pain, blood loss, and recuperation time. In addition, it also offers better ergonomy for the surgeon compared to open and laparoscopic techniques, improved dexterity, precision, and tremor suppression, and the removal of the fulcrum effect. Although being technically easier, robotic surgery still involves several drawbacks. One major disadvantage of previously-known robotic surgical systems relates to the extremely high complexity of such systems, which contain four to five robotic arms to replace the hands of both the surgeon and the assistant, integrated endoscopic imaging systems, as well as the ability to perform remote surgery, leading to huge capital costs for acquisition and maintenance, and limiting the affordably for the majority of surgical departments worldwide. Another drawback of these systems is the bulkiness of previously-known surgical robots, which compete for precious space within the operating room environment and significantly increasing preparation time. Access to the patient thus may be impaired, which raises safety concerns.

For example, the da Vinci® surgical systems (available by Intuitive Surgical, Inc., Sunnyvale, California, USA) is a robotic surgical system for allowing performance of remote laparoscopy by a surgeon. However, the da Vinci® surgical systems are very complex robotic systems, with each system costing around $2,000,000 per robot, $150,000 per year for servicing, and $2,000 per surgery for surgical instruments. The da Vinci® surgical system also requires a lot of space in the operating room, making it hard to move around to a desired location within the operating room, and difficult to switch between forward and reverse surgical workspaces (also known as multi-quadrant surgery).

Moreover, as the surgeon's operating console is typically positioned away from the surgical site, the surgeon and the operating console are not in the sterile zone of the operating room. If the surgeon's operating console is not sterile, the surgeon is not permitted to attend to the patient if necessary without undergoing additional sterilization procedures. During certain surgical operations, a surgeon may need to intervene at a moment's notice, and current bulky robotic systems may prevent the surgeon from quickly accessing the surgical site on the patient in a timely, life-saving manner.

WO97/43942 to Madhani, WO98/25666 to Cooper, and U.S. Patent Application Publication No. 2010/0011900 to Burbank each discloses a robotic teleoperated surgical instrument designed to replicate a surgeon's hand movements inside the patient's body. By means of a computerized, robotic interface, the instrument enables the performance of remote laparoscopy, in which the surgeon, seated at a console and manipulating two joysticks, performs the operation through several small incisions. Those systems do not have autonomy or artificial intelligence, being essentially a sophisticated tool that is fully controlled by the surgeon. The control commands are transmitted between the robotic master and robotic slave by a complex computer-controlled mechatronic system, which is extremely costly to produce and maintain and requires considerable training for the hospital staff.

WO2013/014621 to Beira, the entire contents of which are incorporated herein by reference, describes a mechanical teleoperated device for remote manipulation which comprises master-slave configuration including a slave unit driven by a kinematically equivalent master unit, such that each part of the slave unit mimics the movement of a corresponding part of the master unit. A typical master-slave telemanipulator provides movement in seven degrees-of-freedom. Specifically, these degrees of freedom include three translational macro movements, e.g., inward/outward, upward/downward, and left/right degrees-of-freedoms, and four micro movements including one rotational degree-of-freedom, e.g., pronosupination, two articulation degrees-of-freedom, e.g., yaw and pitch, and one actuation degree-of-freedom, e.g., open/close. Although the mechanical transmission system described in that publication is well adapted to the device, the low-friction routing of the cables from handles through the entire kinematic chain to the instruments is costly, complex, bulky, and requires precise calibration and careful handling and maintenance.

In addition, previously-known purely mechanical solutions do not offer wrist alignment, low device complexity, low mass and inertia, high surgical volume, and good haptic feedback. For example, with a purely mechanical teleoperated device, in order to perform a pure pronosupination/roll movement of the instrument, the surgeon typically has to perform a combined pronosupination/roll movement of his hand/forearm as well as a translational movement on a curved path with his wrist. Such movements are complex to execute properly, and if not done properly, the end-effector pitches and yaws creating undesired parasitic movements.

Further, the routing of the articulation and actuation degrees-of-freedom cables through mechanical telemanipulators may limit the dexterity of the angular range of the various joints of the telemanipulator link-and-joint structure. This in turn limits the available surgical volume of the instruments accessible within the patient. During rapid movements of the mechanical telemanipulators, inertia of the telemanipulators also may be disturbing and result in over-shoot of the target and fatigue of the surgeon's hand. Part of this mass can be attributed to parts and components required to route the actuation and articulation degrees-of-freedom.

Accordingly, it would be desirable to provide remotely actuated surgical robot systems having robotic telemanipulators that are well adapted for use by the surgeon, seamlessly integrated into the operation room, allow for a surgeon to work between the robot and the patient in a sterile manner, are relatively low cost, and/or permit integrated laparoscopy.

It would further be desirable to provide a remotely actuated surgical robot having mechanical and/or electromechanical telemanipulators.

SUMMARY

The present invention overcomes the drawbacks of previously-known systems by providing remotely actuated surgical robot systems having robotic telemanipulators that are preferably well adapted for use by the surgeon, seamlessly integrateable into the operation room, allow for a surgeon to work between the robot and the patient throughout a surgery in a sterile manner, are relatively low cost, and/or permit integrated laparoscopy.

The surgical robot system for remote manipulation includes a master console having a plurality of master links, and a handle coupled to the master console such that movement applied at the handle moves at least one of the plurality of master links. The master console may be designed to remain sterile during the surgery. In accordance with one aspect, the handle may be removeably coupled to the master console such that the handle is sterile during the surgery and sterilizable while removed for additional surgeries. For example, the handle may be removeably coupled to the master console via, e.g., a clip attachment or a screw attachment. The removable handle may be purely mechanical without electronics such as circuits, sensors, or electrically coupled buttons to facilitate sterilization between surgeries while the handle is removed from the master console. In this manner, the master console may be sterile (e.g., covered with a sterile drape except at the handles) during the surgery while permitting the surgeon to have the tactile feedback available from direct contact with the robot's handles.

The surgical robot system further includes a slave console having a plurality of slave links. In accordance with one aspect, the distal end of the slave console may be rotatable about an alpha-axis of an angulation slave link of the plurality slave links such that the distal end of the slave console is positionable in a manner to permit a user to move from the master console to manually perform a laparoscopic procedure on a patient undergoing the surgery.

In addition, the system includes an end-effector coupled to the slave console, wherein the end-effector moves responsive to movement applied at the handle and responsive to movement at the slave console to perform the surgery. For example, the slave console may include a plurality of actuators, e.g., motors, operatively coupled to the end-effector that, when activated responsive to actuation at the handle, apply translational macro-movements to the plurality of slave links during a macro-synchronization state, but not in an unsynchronized macro state, and apply micro-movements to the end-effector during a micro-synchronization state, but not in an unsynchronized micro state. Moreover, the surgical robot system may include an instrument having a proximal end and a distal end, the proximal end having an instrument hub designed to be coupled to the distal end of the slave console, and the distal end having the end-effector.

The handle may include a retractable piston that moves responsive to actuation of the handle. Thus, at least one sensor of the master console is designed to sense movement of the retractable piston to cause the plurality of actuators to make corresponding micro-movements at the end-effector. In accordance with one aspect of the present invention, the slave console does not respond to movement at the master console unless the at least one sensor senses at least a predetermined amount of the retractable piston. Further, at least one sensor coupled to the handle may be designed to sense an actuation pattern of the handle that transitions the robot from an unsynchronized micro state to the micro-synchronized state. For example, in the unsynchronized micro state, movement at the handle sensed by the plurality of sensors does not a cause corresponding micro-movement by the end-effector until the robot is transitioned to the micro-synchronized state because the at least one sensor senses the actuation pattern of the handle.

The master console may include a mechanical constraint designed to constrain movement of at least one master link of the plurality of master links, and may further include a clutch that when actuated prevents translational macro-movement of the plurality of master links. The surgical robot system further may include a display coupled to the master console that permits a user to visualize the end-effector during operation of the telemanipulator. Additionally, the system may include a removable incision pointer that permits alignment of the distal end of the slave console with a trocar positioned within a patient undergoing the surgery.

Moreover, the base of the slave console may be coupled to a proximal slave link of the plurality of slave links via a proximal slave joint of a plurality of slave joints such that the plurality of slave links and joints are moveable about the proximal slave joint to position the distal end of the slave console at a desired horizontal location prior to performing the surgery while the base of the slave console remains stationary. In addition, the base of the slave console may include an adjustable vertical column coupled to the proximal slave link of the plurality of slave links. The adjustable vertical column may adjust a height of the plurality of slave links and joints to position the distal end of the slave console at a desired vertical location prior to operation of the telemanipulator.

In accordance with one aspect of the present application, slave links and joints of the pluralities of slave links and joints distal to a beta joint of the plurality of slave joints are designed to move relative to the beta joint to flip the distal end of the slave console between a forward surgical workspace and a reverse surgical workspace while slave links of the plurality of slave links proximal to the beta joint, and a base of the slave console, remain stationary.

The surgical robot system also may include a controller operatively coupled to the plurality of actuators such that the plurality of actuators apply movement to the plurality of slave links of the slave console responsive to instructions executed by the controller. For example, the controller may execute instructions to cause the plurality of actuators to move the plurality of slave links of the slave console to a home configuration where, in the home configuration, the plurality of slave links are retracted such that the end-effector is positionable within a trocar inserted in a patient undergoing the surgery. In addition, the controller may execute instructions to cause the plurality of actuators to move an angulation slave link of the plurality slave links to an angle such that the angulation slave link and the slave links of the slave console proximal to the angulation slave link remain stationary during operation of the telemanipulator. Accordingly, at the angle of the angulation slave link, the distal end of the slave console permits the end-effector to perform the surgery in a semi-spherical surgical workspace tilted at an angle essentially parallel to the angle of the angulation slave link.

In accordance with another aspect of the present invention, the master console has a master controller and the slave console has a slave controller, such that the master controller may execute instructions based on movement sensed at the handle and transmit signals to the slave controller based on the movement. Accordingly, the slave controller may receive the signals and execute instructions to move at least one of the plurality of slave links or the end-effector, or both, based on the signals transmitted from the master controller. For example, the slave console may include a right slave telemanipulator, a right slave controller, a left slave telemanipulator, and a left slave controller, and the master console may include a right master telemanipulator, a left master telemanipulator, and master controller, such that, in a forward surgical workspace configuration, the master controller communicates with the right slave controller to cause the right slave telemanipulator to move responsive to movement at the right master telemanipulator and the master controller communicates with the left slave controller to cause the left slave telemanipulator to move responsive to movement at the left master telemanipulator. Additionally, in accordance with some embodiments, in a reverse surgical workspace configuration, the master controller communicates with the left slave controller to cause the left slave telemanipulator to move responsive to movement at the right master telemanipulator and the master controller communicates with the right slave controller to cause the right slave telemanipulator to move responsive to movement at the left master telemanipulator.

Accordingly, a distal end of the right slave telemanipulator may be rotatable about the alpha-axis of a right angulation slave link of the plurality of right slave links, and a distal end of the left slave telemanipulator may be rotatable about the alpha-axis of a left angulation slave link of the plurality of left slave links such that the distal ends of the right and left slave telemanipulators are positionable in a manner to permit a user to move from the master console to manually perform a laparoscopic procedure on a patient undergoing the surgery. In addition, the right handle may be removeably coupled to the right master telemanipulator and the left handle may be removeably coupled to the left master telemanipulator.

DETAILED DESCRIPTION

A remotely actuated surgical robot system having robotic telemanipulators and integrated laparoscopy, which may be used in minimally invasive surgical procedures or in other applications, constructed in accordance with the principles of the present invention, is described herein. The surgical robot system provides the value of robotics for long and difficult surgical tasks such as suturing and dissection, and permits a user, e.g., a surgeon, to efficiently switch to integrated laparoscopy for short and specialized surgical tasks such as vessel sealing and stapling. The fully articulated instruments simplify complex surgical tasks, and replication of hand movements increase precision. The user may be seated or standing in a relaxed ergonomic working position to improve surgeon focus and performance.

Figure 1:
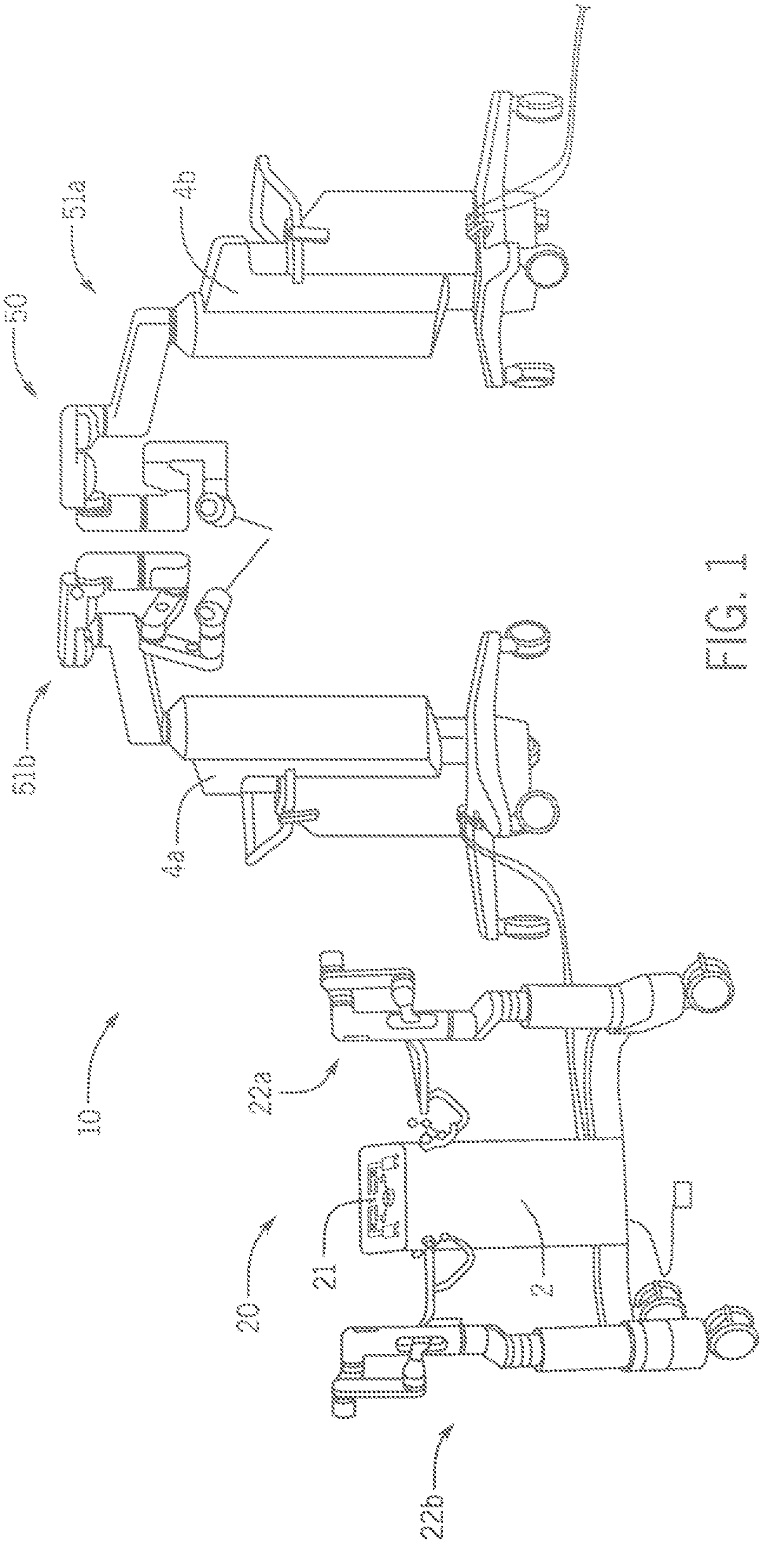
FIG. 1 shows an exemplary remotely actuated surgical robot system having robotic telemanipulators constructed in accordance with the principles of the present invention.

Referring to FIG. 1, exemplary remotely actuated surgical robot system 10 having robotic telemanipulators is described. Surgical robot system 10 includes master console 20 electrically and operatively coupled to slave console 50 via, e.g., electrical cables. As described in further detail below, surgical robot system 10 includes a macro-synchronization state where a plurality of actuators, e.g., preferably motors, coupled to slave console 50 applies translational macro-movements to an end-effector of slave console 50 responsive to movement applied at master console 20 via a processor-driven control system, and a micro-synchronization state where a plurality of actuators, e.g., preferably motors, coupled to slave console 50 applies micro-movements to an end-effector of slave console 50 responsive to movement applied at a handle of master console 20 via the processor-driven control system.

The control system may include master controller 2 operatively coupled to right master telemanipulator 22*a* and left master telemanipulator 22*b* of master console 20, and slave controllers 4*a* and 4*b* operatively coupled to right slave telemanipulator 51*a* and left slave telemanipulator 51*b* of slave console 50, respectively. For example, master controller 2 may include non-transitory computer readable media, e.g., memory, having instructions stored thereon that, when executed by one or more processors of master controller 2, allow operation of master console 20. Similarly, slave controllers 4*a* and 4*b* may each include non-transitory computer readable media, e.g., memory, having instructions stored thereon that, when executed by one or more processors of respective slave controllers 4*a*, 4*b*, allow operation of slave console 50. Master controller 2 is operatively coupled to slave controller 4*a* and slave controller 4*b* via communication links such as cables (as illustrated) or via wireless communication components.

Master controller 2 may be operatively coupled to one or more sensors of master console 20, and slave controllers 4*a*, 4*b* may be operatively coupled to one or more actuators of slave console 50 such that master controller 2 may receive signals indicative of movement applied at master console 20 by the one or more sensors of master console 20, and execute instructions stored thereon to perform coordinate transforms necessary to activate the one or more actuators of slave console 50, send the processed signals to respective slave controllers 4*a*, 4*b* that execute instructions stored thereon to move slave console 50 in a manner corresponding to movement of master console 20 based on the processed signals. For example, the one or more actuators may include one or more motors. Alternatively, master controller 2 may receive the signals from the one or more sensors of master console 20, process the signals, and transmit the processed signals to respective slave controllers 4*a*, 4*b* which execute instructions stored thereon to perform the coordinate transforms based on the processed signals, and execute instructions to activate the one or more actuators of slave console 50 to move slave console 50 in a manner corresponding to movement of master console 20 based on the transformed, processed signals. Preferably, the slave links and joints of slave console 50 move in a manner such that the end-effector/instrument tip replicates the movement applied at the handle of master console 20, without deviating, during operation of surgical robot system 10, from a remote center-of-motion, as described in further detail below. Thus, translation degrees-of-freedom, e.g., left/right, upward/downward, inward/outward, the articulation degrees-of-freedom, e.g., pitch and yaw, the actuation degrees-of-freedom, e.g., open/close, and the rotation degree-of-freedom, e.g., pronosupination, are electromechanically replicated via sensors, actuators, and a control system as described in further detail below.

Master console 20 may be positioned within the operating room where a user, e.g., surgeon, may be situated, and in close proximity to slave console 50 where a patient undergoing surgery may be situated, e.g., the sterile zone, so that the user may move quickly between master console 20 and slave console 50 to manually perform laparoscopy during the surgery if necessary. Accordingly, slave console 50 is designed to efficiently retract to a configuration to permit the surgeon to access the surgical site on the patient as described in further detail below. Master console 20 may be covered with a sterile drape, and may include removable handles that may be removed and sterilizable between surgeries such that the handles are sterile during the surgery and there are no physical barriers between the handles and the surgeon's hands, thereby improving control and performance by the surgeon. The removable handle may be purely mechanical without electronics such as circuits, sensors, or electrically coupled buttons so that the removable handle is easily sterilizable between surgeries. In this manner, the master console may be sterile during the surgery while permitting the surgeon to have the tactile feedback available from direct contact with the robot's handles.

As illustrated in FIG. 1, master console 20 includes right master telemanipulator 22*a* and left master telemanipulator 22*b*. Right master telemanipulator 22*a* and left master telemanipulator 22*b* may be positioned on a single master console such that right master telemanipulator 22*a* may be manipulated by the surgeon's right hand and left master telemanipulator 22*b* may be manipulated by the surgeon's left hand when the surgeon is situated at master console 20. Accordingly, master console 20 may include wheels for mobility within the operating room, and wheel locks that may be actuated to lock the telemanipulators in position, e.g., during storage or during use by the surgeon during the surgery. In addition, right master telemanipulator 22*a* and left master telemanipulator 22*b* may be operated simultaneously and independently from the other, e.g., by the surgeon's right and left hands. Preferably, surgical robot system 10 is optimized for use in surgical procedures.

As further illustrated in FIG. 1, slave console 50 includes right slave telemanipulator 51*a* operatively coupled to right master telemanipulator 22*a*, and left slave telemanipulator 51*b* operatively coupled to left master telemanipulator 22*b*. Right and left slave telemanipulators 51*a* and 51*b* may be positioned on separate consoles such that right slave telemanipulator 51*a* may be positioned on the right side of the patient undergoing surgery and left slave telemanipulator may be positioned on the left side of the patient. Accordingly, right and left slave telemanipulators 51*a* and 51*b* each may include wheels for mobility within the operating room, and floor locks that may be actuated to lock the telemanipulators in position, e.g., during storage or adjacent the patient during the surgery. In addition, right and left slave telemanipulators 51*a* and 51*b* each may include a pull bar for pushing and pulling the telemanipulators within the operating room.

Moreover, a camera system may be used with surgical robot system 10. For example, a camera e.g., an endoscope, that is manipulated by the assistant situated at slave console 50 may be operated and/or held in position at slave console 50. Accordingly, the camera system may include display 21 mounted on master console 20 in a position that is easily observable by the surgeon during a surgical procedure. Display 21 may display status information on the surgical robot system 10, and/or display the surgical site captured by the endoscopic camera to surgeon in real-time.

Figure 2A:
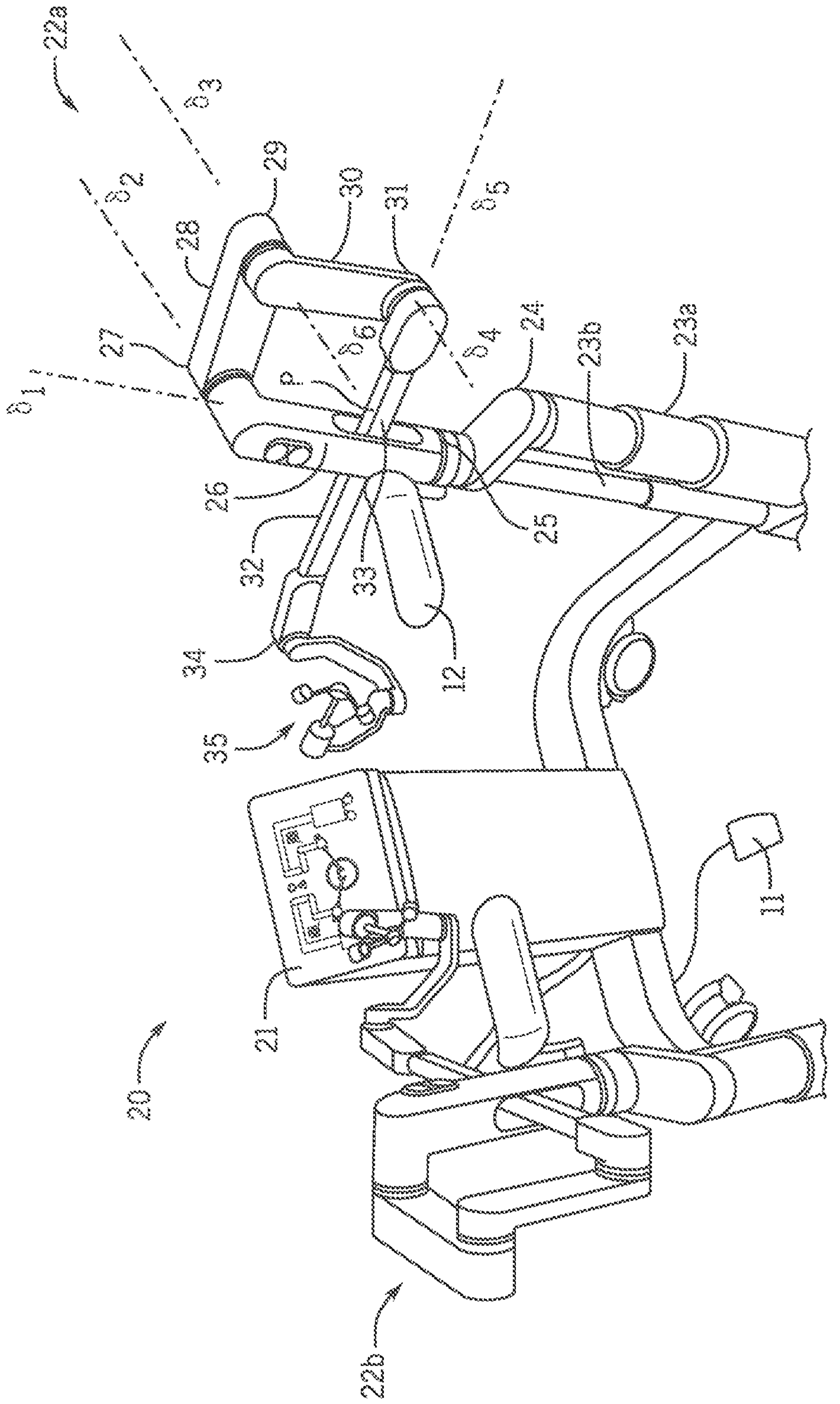
FIG. 2A shows an exemplary master console constructed in accordance with the principles of the present invention.

Referring now to FIG. 2A, exemplary master console 20 is described. As described above, master console 20 includes right master telemanipulator 22*a* and left master telemanipulator 22*b*. As left master telemanipulator 22*b* may be a structurally mirrored version of right master telemanipulator 22*a* as illustrated, the description below of right master telemanipulator 22*a* applies also to left master telemanipulator 22*b*.

Master telemanipulator 22*a* includes a plurality of master links, e.g., first master link 26, second master link 28, third master link 30, and fourth master link, e.g., guided master link 32, interconnected by a plurality of master joints, e.g., first master joint 25, second master joint 27, third master joint 29, fourth master joint 31, and fifth master joint 34. As shown in FIG. 1, handle portion 35 is connected to master telemanipulator 22*a* via joint 34, and includes a plurality of handles links interconnected by a plurality of handle joints for operating master telemanipulator 22*a*. In addition, master telemanipulator 22*a* includes a base portion having telescoping bases 23*a* and 23*b*, and base cap 24 fixed atop telescoping bases 23*a* and 23*b*. Link 26 is rotatably coupled to base cap 24 via joint 25. Thus, link 26, and accordingly all the master joints and links distal to link 26, may rotate relative to base cap 24 about axis $\delta_1$ at joint 25. As shown in FIG. 1, link 28, and accordingly all the master joints and links distal to link 28, may rotate relative to link 26 about axis $\delta_2$ at joint 27, link 30, and accordingly all the master joints and links distal to link 30, may rotate relative to link 28 about axis $\delta_3$ at joint 29, and guide master link 32, and accordingly all the master joints and links distal to guided master link 32, may rotate relative to link 30 about axis $\delta_4$ at joint 31.

Master console 20 includes a plurality of sensors positioned within master telemanipulator 22*a* such that any movement applied to any master links and joints may be sensed and transmitted to the control system, which will then execute instructions to cause one or more actuators coupled to slave console 50 to replicate the movement on corresponding slave link and joints of slave telemanipulator 51*a*, as described in further detail below with reference to FIG. 12.

Still referring to FIG. 2A, master telemanipulator 22*a* includes mechanical constraint 33, which includes an opening within link 26 sized and shaped to permit guided master link 32 to be positioned therethrough, thereby constraining movements of master telemanipulator 22*a* about a pivot point at master telemanipulator 22*a*. For example, mechanical constraint 33 ensures that, when master telemanipulator 22*a* is actuated, guided master link 32 translates along longitudinal axis $\delta_5$. In addition, mechanical constraint 33 enables guided master link 32 to rotate about axes $\delta_1$ and $\delta_6$ that are perpendicular to each other, creating a plane that intersects longitudinal axis $\delta_5$ at stationary pivot point P independently of the orientation of guided master link 32. As a result, the slave telemanipulator produces corresponding movements, thereby virtually maintaining the pivot point of the master telemanipulator, for example, at the fixed incision point on a patient where a trocar passes into a patient's abdomen.

When surgical robot system 10 is positioned such that remote center-of-motion V is aligned with the patient incision, translational movement applied to handle portion 35 is replicated by the end-effector disposed inside the patient. Because the end-effector replicates the movement applied to handle portion 35, this arrangement advantageously eliminates the fulcrum effect between the handle and end-effector.

In addition, master console 20 may include arm support 12, e.g., coupled to base cap 24, sized and shaped to permit the surgeon to rest the surgeon's arms against the arm support during operation of master console 20. Accordingly, arm support 12 remains static during operation of master telemanipulator 22*a*. Master console 20 further may include clutch 11, e.g., a foot pedal, that when actuated prevents macro-synchronization of surgical robot system 10, as described in further detail below.

Figure 2B:
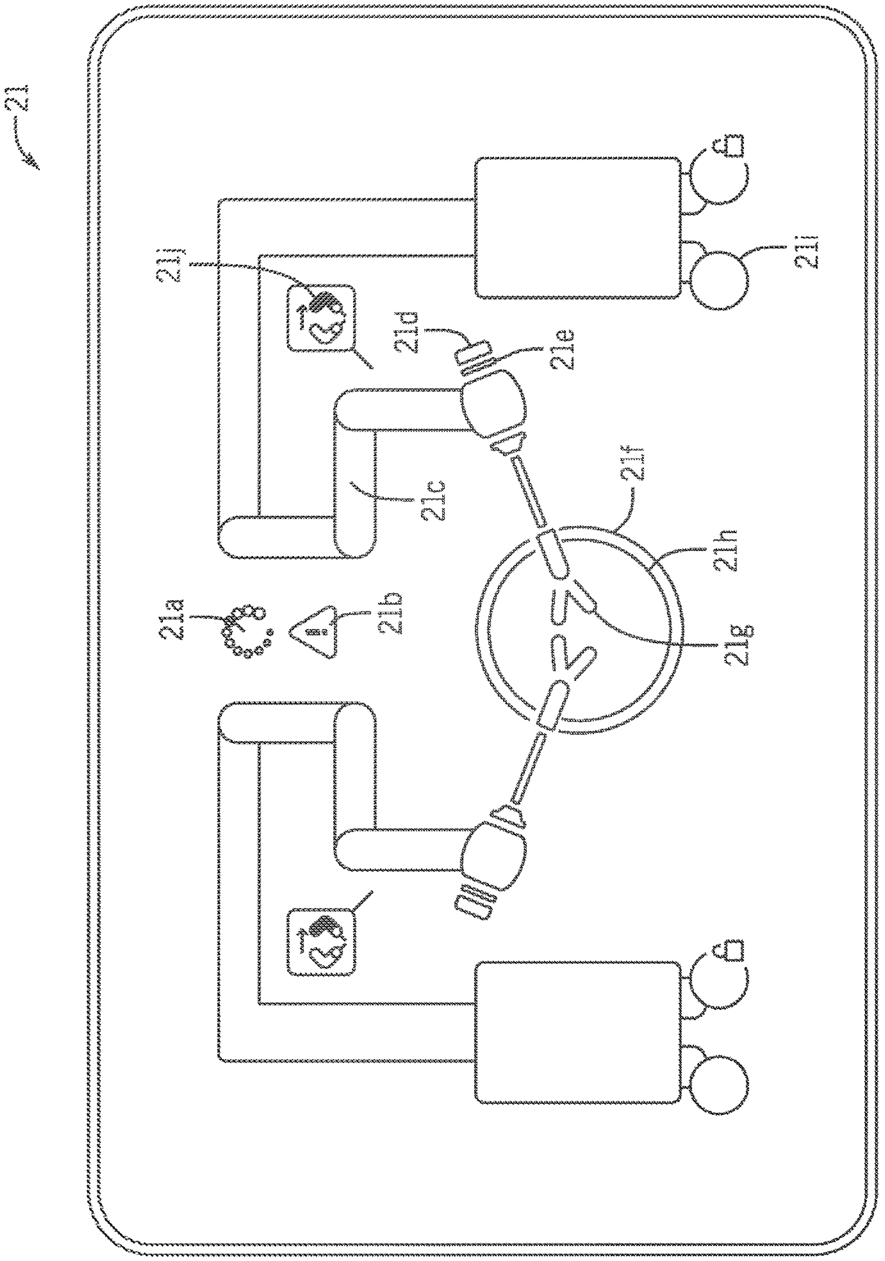
FIG. 2B shows an exemplary display constructed in accordance with the principles of the present invention.

Referring now to FIG. 2B, display 21 is described. Display 21 may have a simplistic design without text, utilizing only visible graphical elements and LEDs, e.g., white, yellow, and red lights. For example, white light conveys that the component is functioning properly, yellow light conveys that the surgeon has conducted an inappropriate action, and red conveys that there is an error with the component. As shown in FIG. 2B, display 21 graphically displays various components of slave console 50 and the status thereof. Icon 21*a* corresponds with the booting of the system, icon 21*b* corresponds with a system warning, icon 21*h* corresponds with the work limit being reached, and icon 21*j* corresponds with whether the respective slave telemanipulators of slave console 50 are in a forward surgical workspace or a reverse surgical workspace, all of which may be invisible when not lit up, whereas all other icons have a visible graphical element even when not lit up. Icon 21*c* corresponds with homing, e.g., home configuration, of slave console 50, icon 21*d* corresponds with the status of instrument 82, icon 21*e* corresponds with the sterile interface of translation instrument interface 81, icon 21*f* corresponds with macro-synchronization, icon 21*g* corresponds with micro-synchronization, and icon 21*i* corresponds with whether the wheels of slave console 50 are locked or unlocked, the functionality of all of which will be described in further detail below. As will be understood by a person having ordinary skill in the art, display 21 may be any display known in the art that may convey information to the surgeon.

Figure 3A:
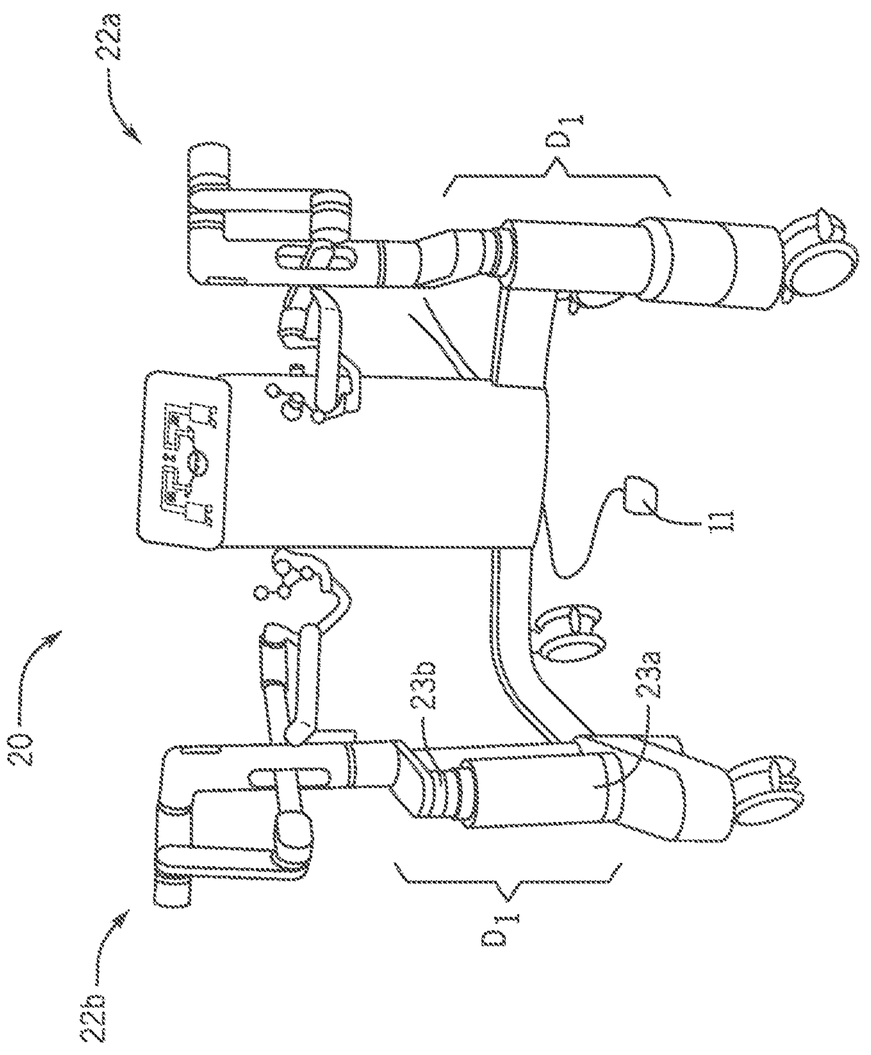
FIG. 3A shows the master console of FIG. 2A in a seated configuration.
Figure 3C:
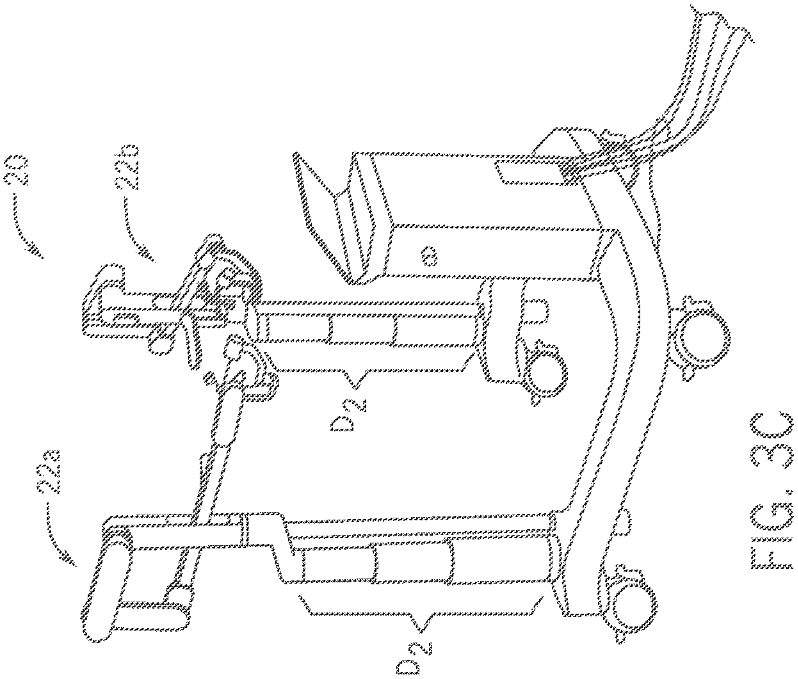
FIGS. 3B and 3C show the master console of FIG. 2A in a standing configuration.
Figure 3B:
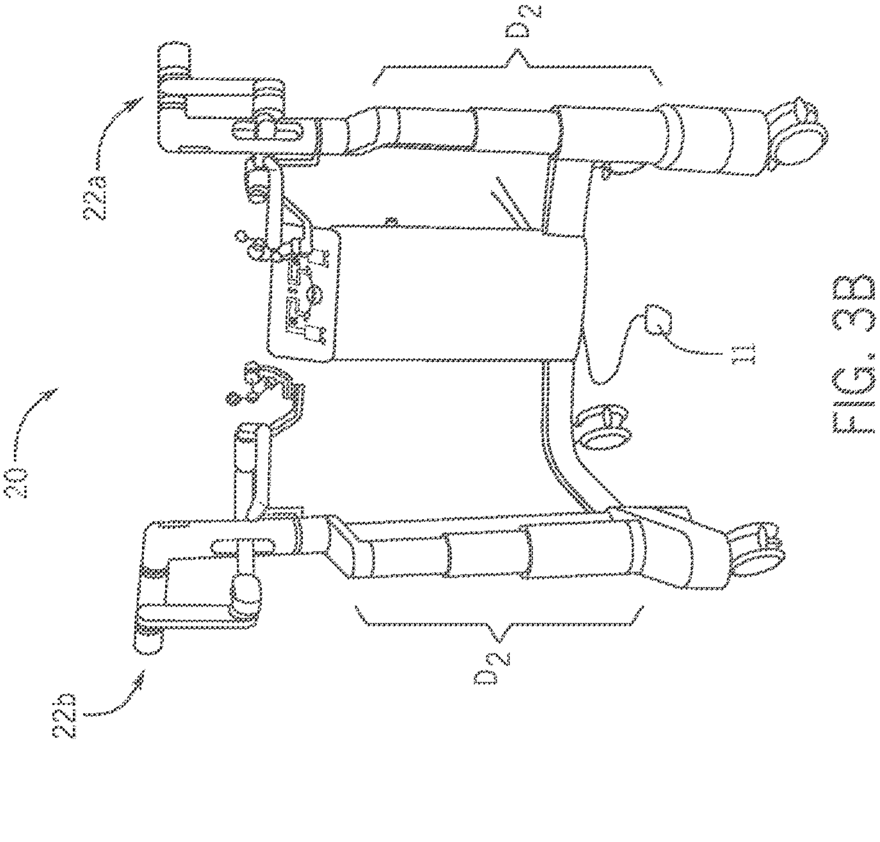

Referring now to FIGS. 3A-3C, master console 20 may be adjusted between a seated configuration and a standing configuration via telescoping bases 23*a* and 23*b*. For example, as illustrated in FIG. 3A, master console 20 may be adjusted to a seated configuration such that telescoping bases 23*a* and 23*b* have a vertical height $D_1$. In this seated configuration, the surgeon may be seated during operation of master console 20. As illustrated in FIGS. 3B and 3C, master console 20 may be adjusted to a standing configuration such that telescoping bases 23*a* and 23*b* have a vertical height $D_2$. In this configuration, the surgeon may be standing during operation of master console 20. In addition, the vertical height of telescoping bases 23*a* and 23*b* may be adjusted via an actuator positioned on master console 20, e.g., on master link 26. For example, the actuator may include up and down buttons that when actuated, cause the vertical height of telescoping bases 23*a* and 23*b* to increase or decrease, respectively. As will be understood by a person having ordinary skill in the art, the vertical height of telescoping bases 23*a* and 23*b* may be adjusted to any vertical height between $D_1$ and $D_2$, as desired by the surgeon.

Figure 4:
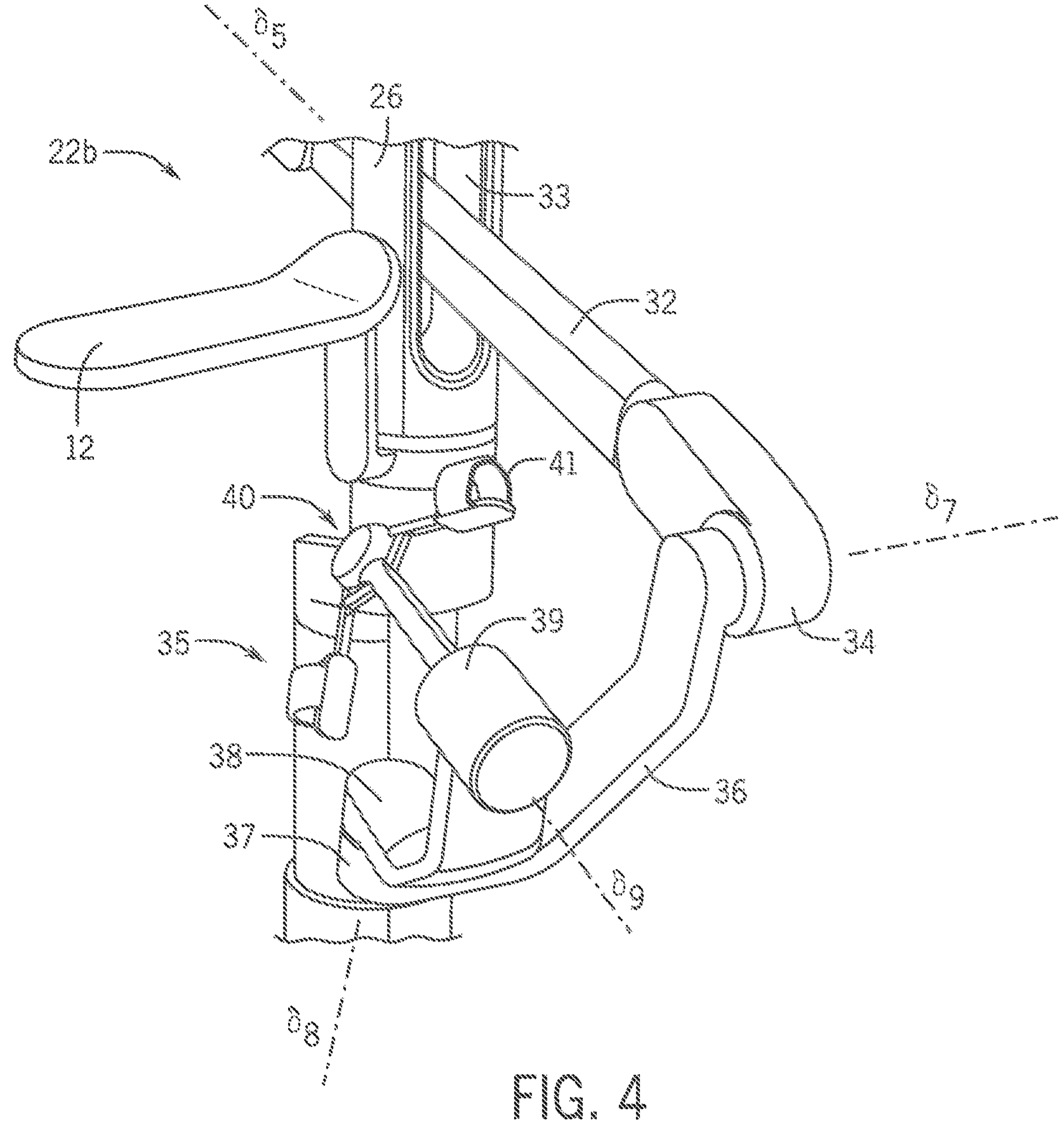
FIG. 4 shows an exemplary master console handle constructed in accordance with the principles of the present invention.

Referring now to FIG. 4, master console handle portion 35 is described. Master console handle portion 35 includes a plurality of handle links, e.g., handle link 36 and handle link 38, interconnected by a plurality of handle joints, e.g., handle joint 37 and handle joint 39. As illustrated in FIG. 4, handle link 36 is rotatably coupled to guided master link 32 via joint 34, and accordingly may rotate relative to guided master link 32 about axis $\delta_7$. In addition, handle link 38 is rotatably coupled to handle link 36 via handle joint 37, and accordingly may rotate relative to handle link 36 about axis $\delta_8$. Moreover, handle grip 40 may be removeably coupled to master console handle portion 35 at joint 39, such that handle grip 40 may rotate relative to handle link 37 about axis $\delta_9$. As shown in FIG. 4, handle grip 40 may include finger strap 41 for engagement with the surgeon's fingers, e.g., thumb and index finger.

Inward/outward movement of handle portion 35 causes guided master link 32 to move inward/outward along longitudinal axis $\delta_5$, the movement of which is sensed by one or more sensors coupled to master telemanipulator 22*a* and transmitted to the control system, which then executes instructions to cause one or more actuators coupled to slave telemanipulator 51*a* to cause the corresponding slave link to replicate the inward/outward movement about virtual longitudinal axis $\omega_9$. Similarly, upward/downward movement of handle portion 35 causes guided master link to move upward/downward along longitudinal axis $\delta_6$, the movement of which is sensed by one or more sensors coupled to master telemanipulator 22*a* and transmitted to the control system, which then executes instructions to cause one or more actuators coupled to slave telemanipulator 51*a* to cause the corresponding slave link to replicate the upward/downward movement about virtual longitudinal axis $\omega_{10}$. Finally, left/right movement of handle portion 35 causes guided master link to move left/right along longitudinal axis $\delta_1$, the movement of which is sensed by one or more sensors coupled to master telemanipulator 22*a* and transmitted to the control system, which then executes instructions to cause one or more actuators coupled to slave telemanipulator 51*a* to cause the corresponding slave link to replicate the left/right movement about virtual longitudinal axis $\omega_5$.

Still referring to FIG. 4, movement applied at handle portion 35 of master telemanipulator 22*a* actuates the articulation degrees-of-freedom, e.g., pitch and yaw, the actuation degree-of-freedom, e.g., open/close, and the rotation degree-of-freedom, e.g., pronosupination, electromechanically via sensors, actuators, and the control system. Master telemanipulator 22*a* preferably includes one or more sensors coupled to handle portion 35 for detecting motion of handle portion 35. As will be understood, the sensors may be any sensor designed to detect rotational movement, such as magnetic-based rotational sensors that includes a magnet on one side and a sensor on another side to measure rotation by measuring angle and position. The sensors are coupled to a control system for generating signals indicative of the rotation measured by the sensors and transmitting the signals to one or more actuators coupled to slave console 50, which may reproduce movements applied on handle portion 35 to the end effector. For example, electrical cables may extend from handle portion 35 to the control system, e.g., a unit containing control electronics, and additional electrical cables may extend from the control system to the one or more actuators coupled to slave console 50.

Figure 5B:
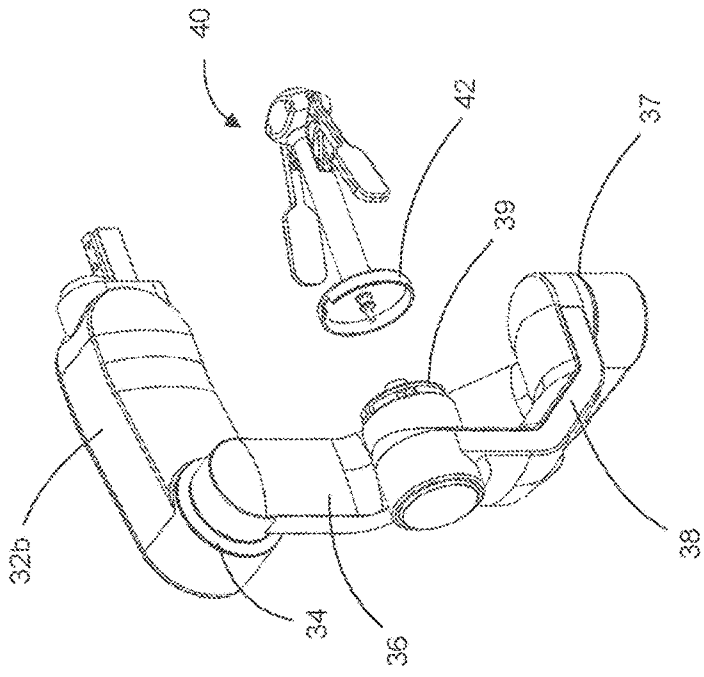
FIGS. 5B and 5C show the handle grip of FIG. 5A removeably coupling with the master console handle of FIG. 4A in accordance with the principles of the present invention.
Figure 5A:
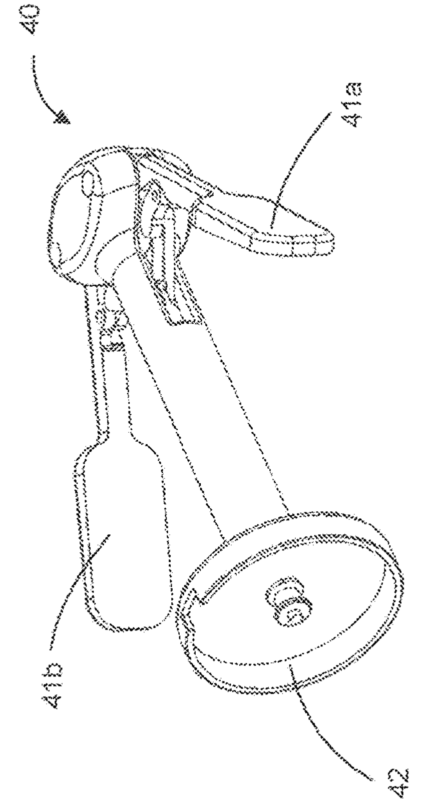
FIG. 5A shows an exemplary handle grip constructed in accordance with the principles of the present invention.

As illustrated in FIG. 5A, handle grip 40 includes triggers 41*a*, 41*b* that are biased toward an open configuration. Accordingly, triggers 41*a*, 41*b* may be actuated to generate a signal that is transmitted via the control system, which executes instructions that causes the actuators coupled to slave console 50 to actuate the end-effector to open/close.

Referring back to FIG. 4, handle grip 40 may be rotatable about handle axis $\delta_9$, such that rotation of the handle grip 40 is detected by a sensor that generates and transmits a signal via the control system, which executes instructions that causes the actuators coupled to slave console 50 to cause rotation of the end-effector in the pronosupination degree-of-freedom.

Handle portion 35 also is rotatable about handle axis $\delta_8$, such that the rotation about handle axis $\delta_8$ is detected by a sensor, which generates and transmits a signal via the control system, which executes instructions that causes the actuators coupled to slave console 50 to cause movement of the end-effector in the yaw degree-of-freedom. In addition, handle portion 35 may be rotatable about handle axis $\delta_7$, such that the rotation of handle portion 35 about handle axis $\delta_7$ is detected by a sensor, which generates and transmits a signal via the control system, which executes instructions that causes the actuators coupled to slave console 50 to cause movement of the end-effector in the pitch degree-of-freedom.

Figure 5C:
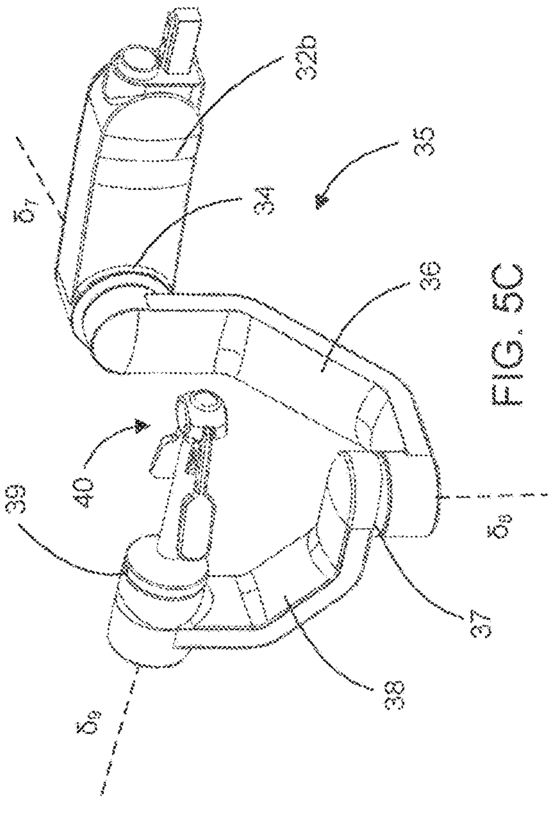

As illustrated in FIGS. 5B and 5C, handle grip 40 may be removeably coupled to handle portion 35 of master telemanipulator 22*a* via joint 39. Accordingly, handle grip 40 may be removed between surgeries to be sterilized, and reconnected to master telemanipulator 22*a* just before a surgery. Thus, as the entirety of master console 20 may be covered with a sterile drape during operation of surgical robot system 10, handle grip 40 will be sterile and may be connected to master console 20 outside of the sterile drape. This permits the surgeon to directly contact handle grip 40 without a physical barrier therebetween, thereby improving tactile feedback and overall performance.

Figure 6A:
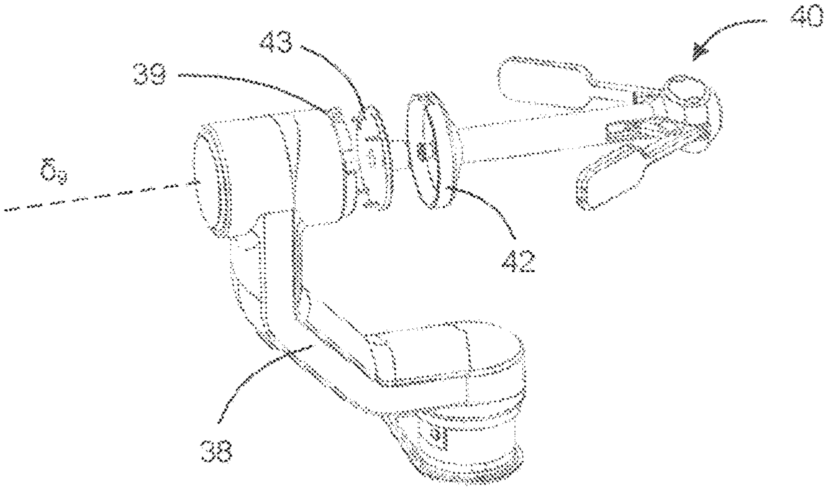
FIGS. 6A-6C show an exemplary handle grip removeably coupling with a master console handle via a clip attachment in accordance with the principles of the present invention.
Figure 6B:
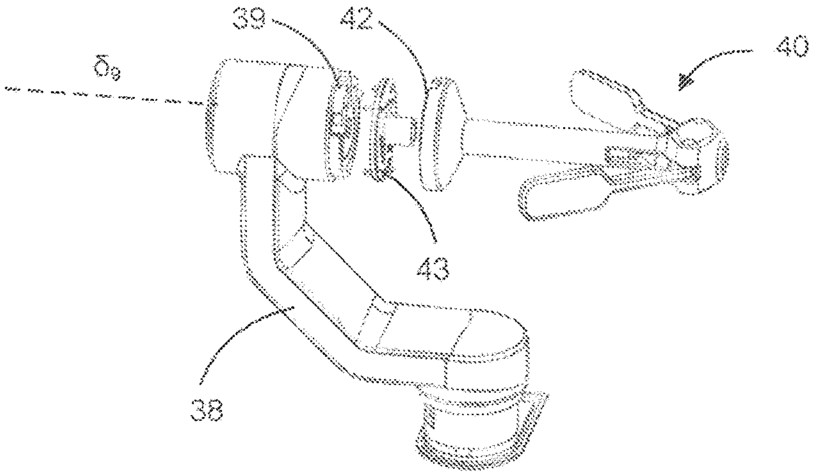
Figure 6C:
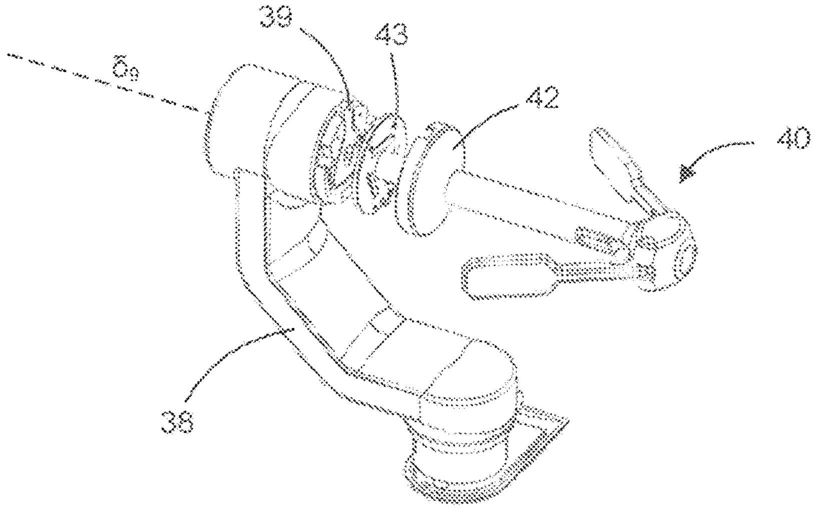
Figure 7:
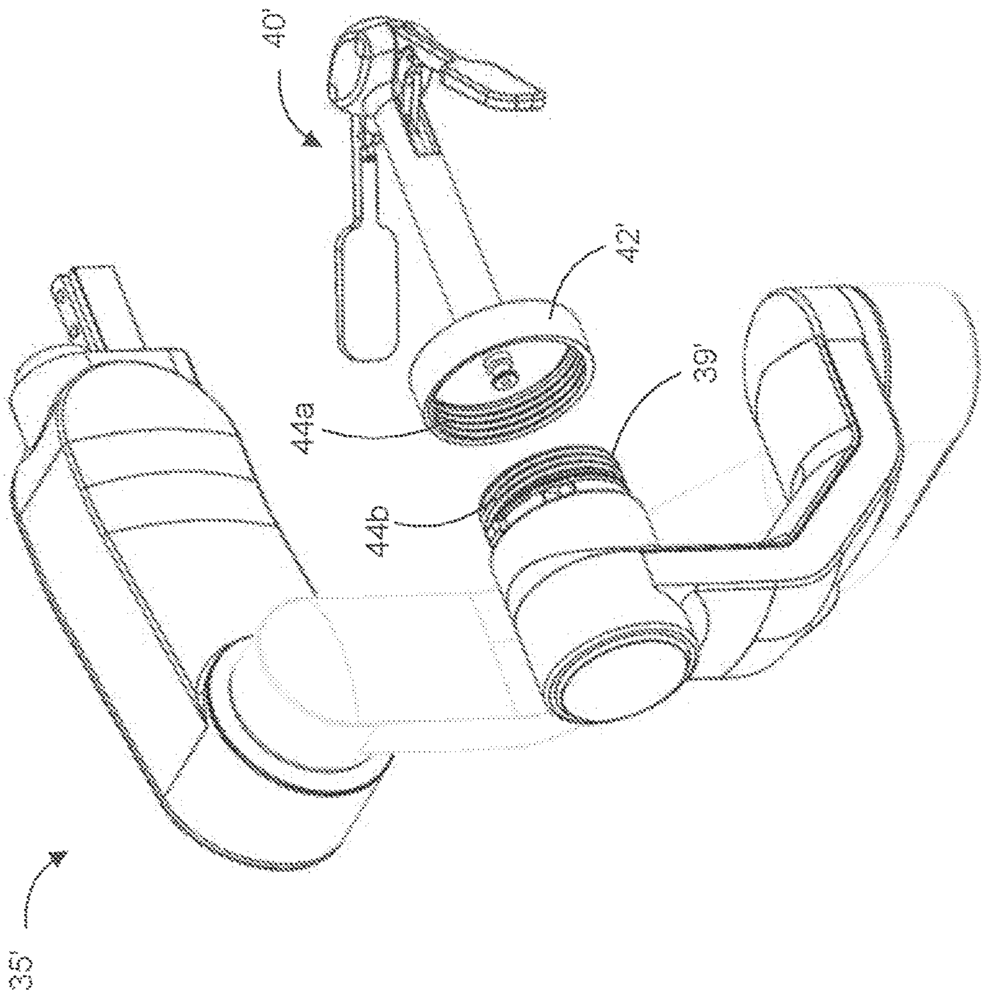
FIG. 7 shows an exemplary handle grip removeably coupling with a master console handle via a screw attachment in accordance with the principles of the present invention.

Referring now to FIGS. 6A-6C, handle grip 40 may be removeably coupled to handle portion 35 of master console 20 via a clip attachment. As shown in FIGS. 6A-6C, spring 43 may be connected to joint 39 of handle portion 35 and clip portion 42 of handle grip 40 to preload the attachment to eliminate fixation backlash. In accordance with another aspect of the present invention, as shown in FIG. 7, handle grip 40' may be removeably coupled to handle portion 35' of master console 20 via a screw attachment. As shown in FIG. 7, screw portion 42' of handle grip 40' having inner threaded portion 44*a* may engage with outer threaded portion 44*b* at joint 39' of handle portion 35', such that handle grip 40' is screwed onto handle portion 35'.

Figure 8A:
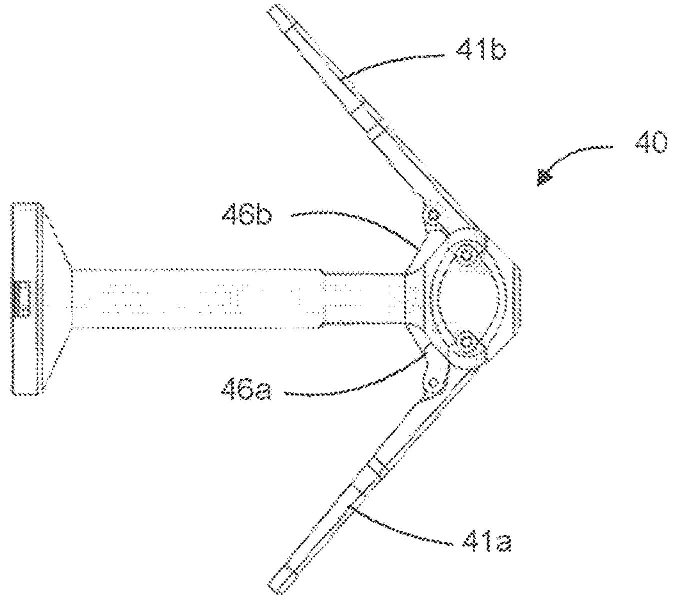
FIGS. 8A-8C show actuation steps of the handle grip of FIG. 5A in accordance with the principles of the present invention.
Figure 8B:
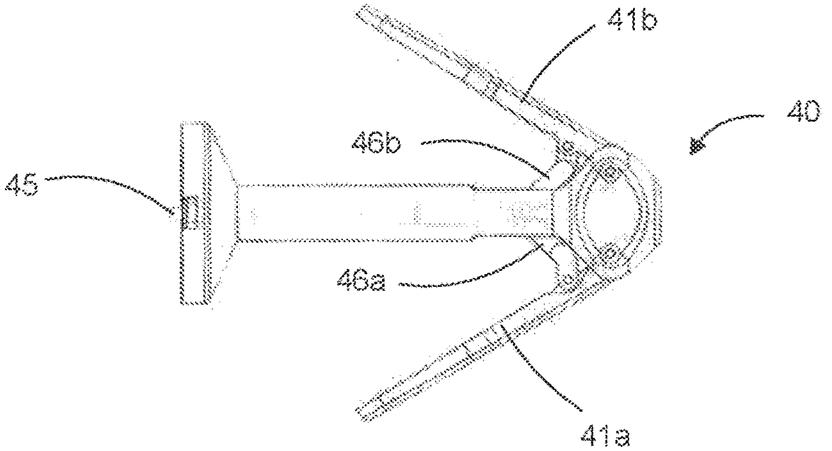
Figure 8C:
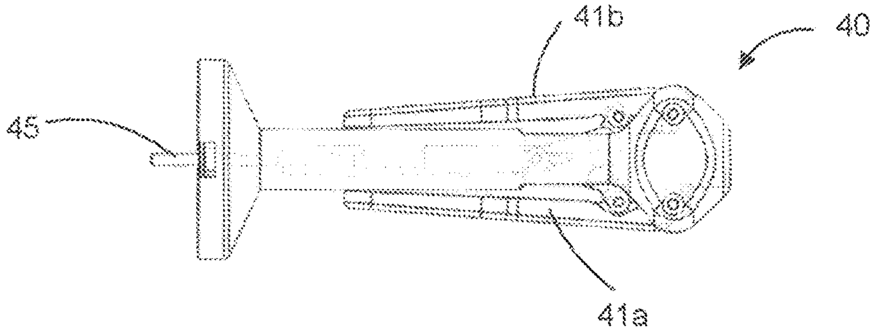

Referring now to FIGS. 8A-8C, actuation steps of handle grip 40 are described. As illustrated in FIGS. 8B and 8C, handle grip 40 includes retractable piston 45 positioned within a central lumen of handle grip 40. Retractable piston 45 is mechanically coupled to triggers 41*a*, 41*b* of handle grip 40 via connectors 46*a*, 46*b*, respectively. As shown in FIG. 8A, when triggers 41*a*, 41*b* are in a relaxed state, e.g., biased toward an open configuration, retractable piston 45 is completely within the central lumen of handle grip 40. As shown in FIGS. 8B and 8C, as handle grip 40 is actuated, e.g., triggers 41*a*, 41*b* are pressed toward each other, connectors 46*a*, 46*b* cause retractable piston 45 to protrude out of the central lumen of handle grip 40. The movement of retractable piston 45 beyond the central lumen of handle grip 40 may be sensed by sensors within handle portion 35.

Figure 9A:
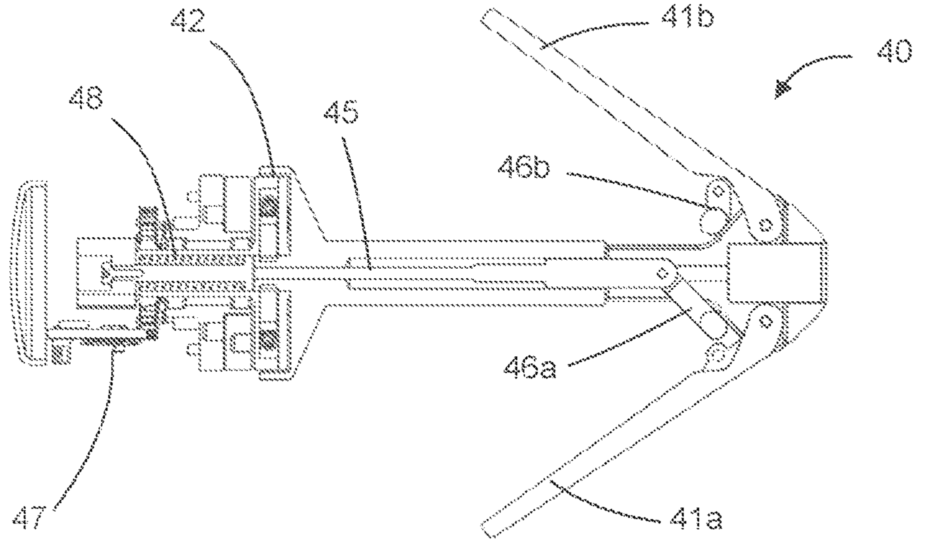
FIGS. 9A and 9B are cross-sectional views of the handle grip of FIG. 5A coupled to the master console handle.
Figure 9B:
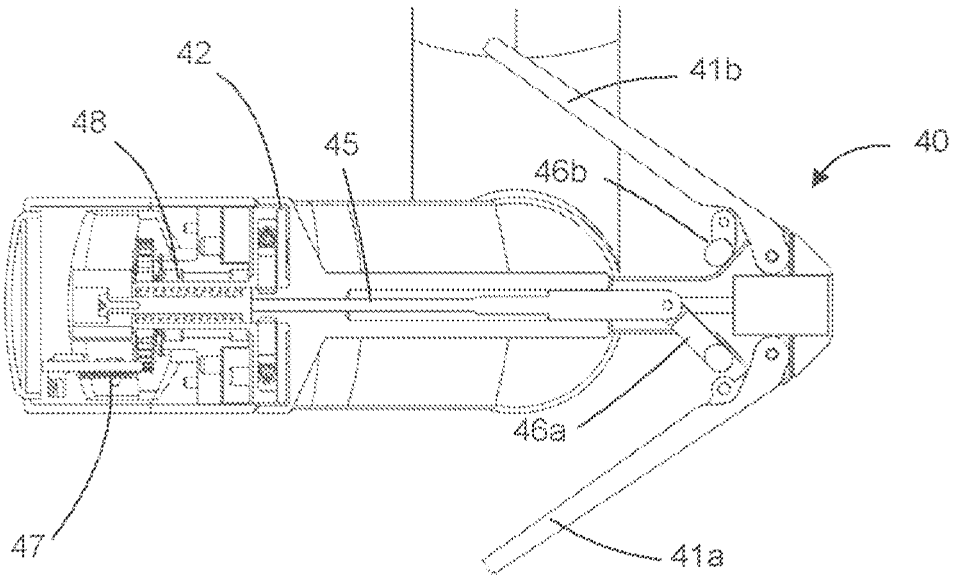

For example, as shown in FIGS. 9A and 9B, the portion of master console adjacent to where handle grip 40 is removeably coupled to handle portion 35 may include one or more sensors 47 for sensing movement at handle portion 35. Accordingly, one or more sensors 47 may transmit a signal to the control system indicating movement of retractable piston 45, and the control system may execute instructions to cause one or more actuators to cause movement by the end-effector. This may serve as a fail-safe because the control system will not instruct the actuators to cause movement by the end-effector without sensors 47 sensing movement of retractable piston 45. For example, when triggers 41*a*, 41*b* of handle grip 40 are in a relaxed state, no movement will be sensed due to small incidental movements of triggers 41*a*, 41*b* until triggers 41*a*, 41*b* are purposefully actuated by the surgeon. Thus, triggers 41*a*, 41*b* may have to be actuated at least a pre-specified amount in order for retractable piston 45 to protrude beyond the central lumen of handle grip 40. In addition, as illustrated in FIGS. 9A and 9B, handle portion 35 may include spring 48 for pushing against retractable piston 45 to bias triggers 41*a*, 41*b* in an open configuration via connectors 46*a*, 46*b*.

Figure 10B:
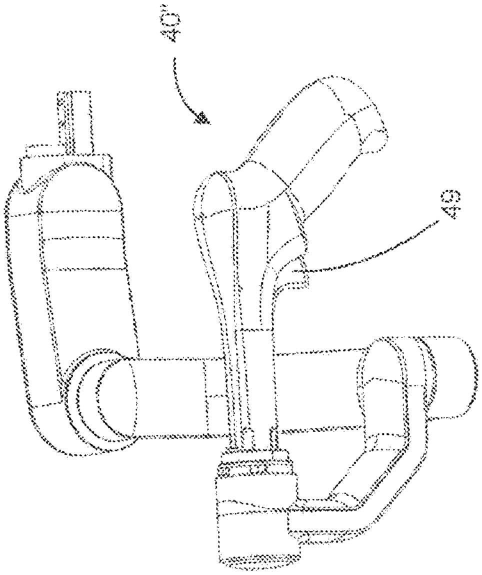
FIGS. 10A-10C show another exemplary master console handle constructed in accordance with the principles of the present invention.
Figure 10A:
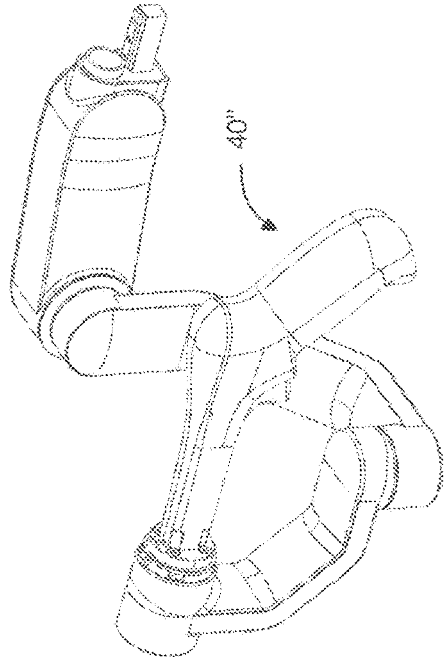
Figure 10C:
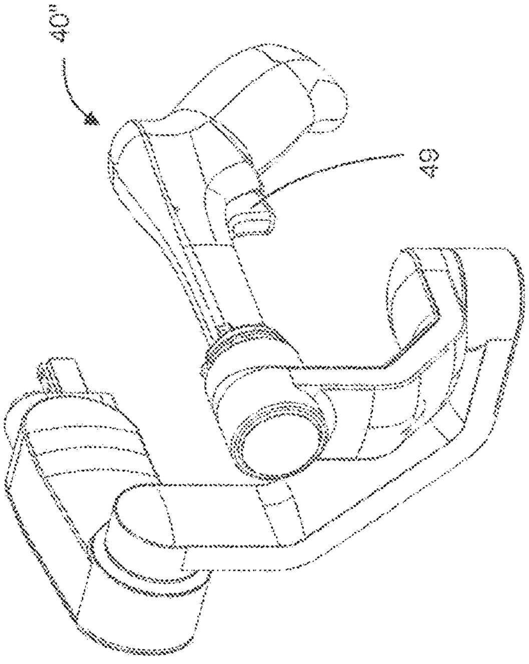

In accordance with another aspect of the present invention, as illustrated in FIGS. 10A-10C, handle grip 40" may be removeably coupled to handle portion 35 of master telemanipulator 22*a*. For example, handle grip 40" may have a pistol shape including a handle and trigger 49 for performing a desired surgical task. As will be understood by a person having ordinary skill in the art, various shaped handle grips may be removeably coupled to the master telemanipulator to actuate a desired movement by the end-effector of the slave telemanipulator. Accordingly, the handle grips may have an integrated identifier element, e.g., an RFID tag, such that the control system detects the identifier element and identifies whether the handle grip is authorized for use with surgical robot system 10.

Figure 11A:
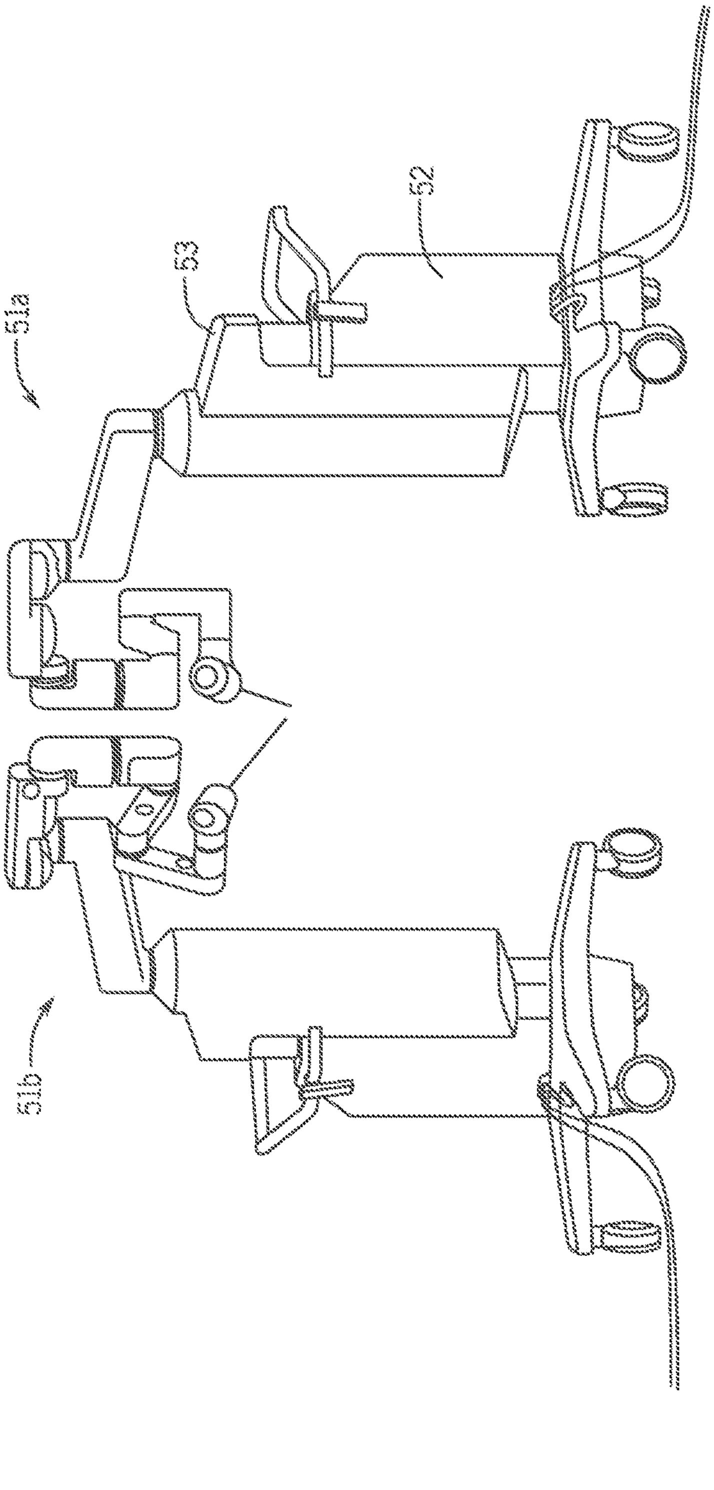
FIGS. 11A and 11B show an exemplary slave console constructed in accordance with the principles of the present invention.
Figure 11B:
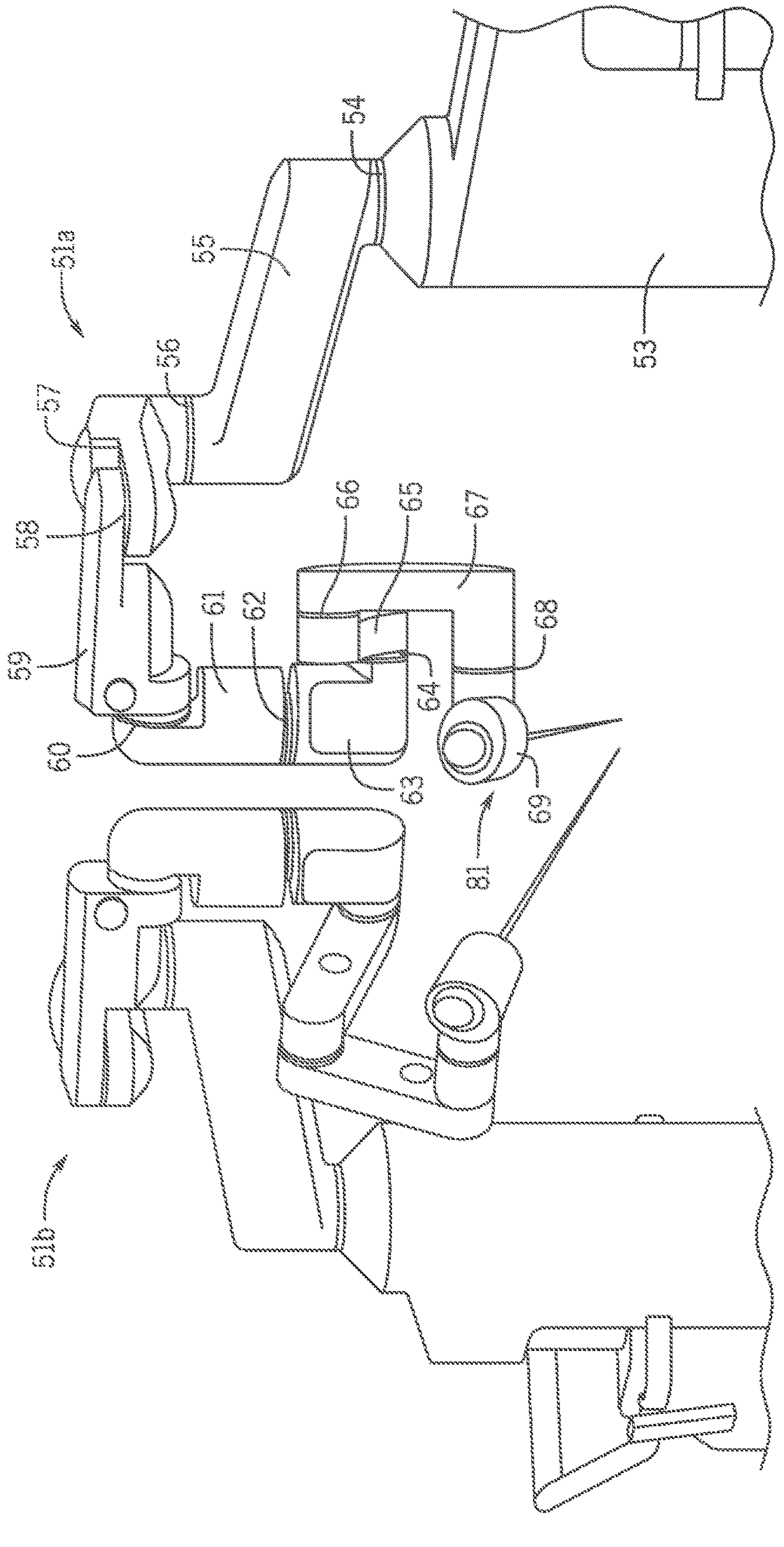

Referring now to FIGS. 11A and 11B, slave console 50 is described. As shown in FIG. 11A, slave console 50 includes right slave telemanipulator 51*a* and left slave telemanipulator 51*b*. As left slave telemanipulator 51*b* may be a structurally mirrored version of right slave telemanipulator 51*a* as illustrated, the description below of right slave telemanipulator 51*a* applies also to left slave telemanipulator 51*b*.

Figure 12:
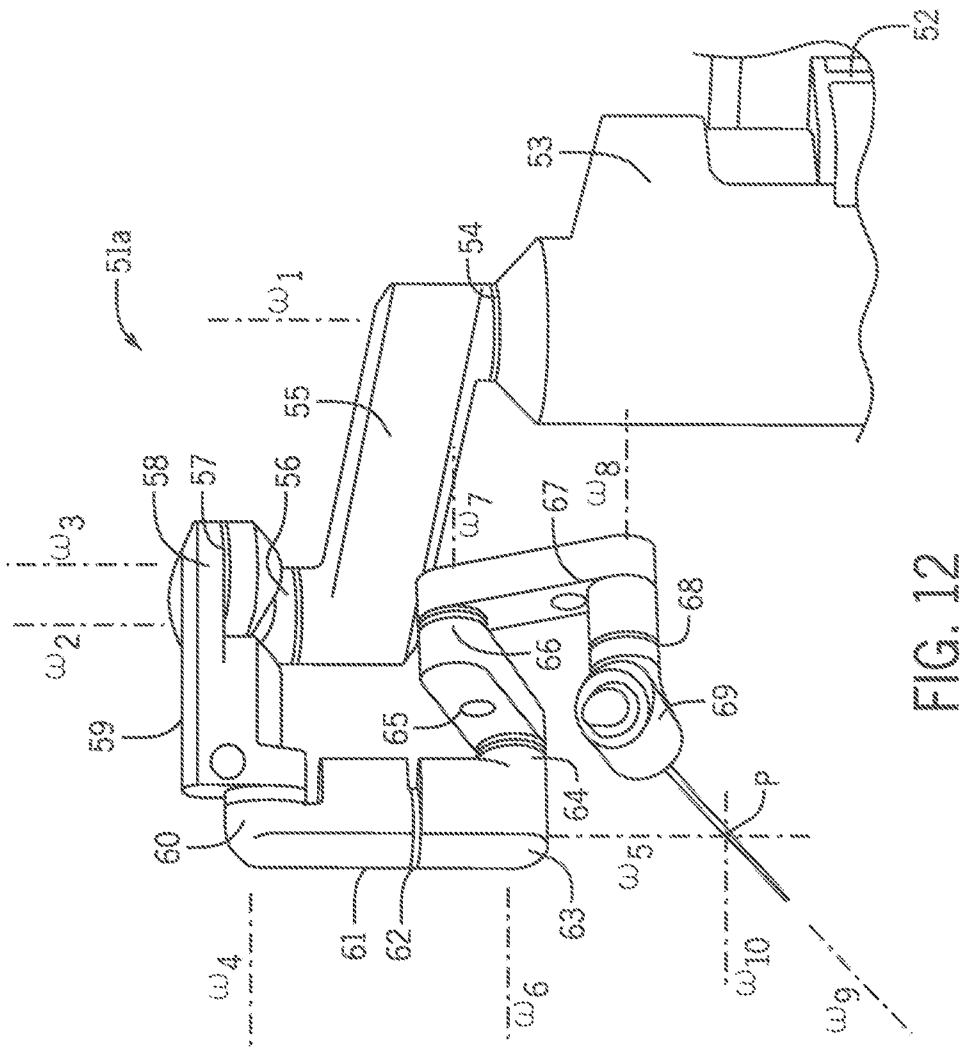
FIG. 12 shows a left slave console constructed in accordance with the principles of the present invention.

As illustrated in FIG. 12, slave telemanipulator 51*a* includes a plurality of slave links, e.g., first slave link 55, second slave link 57, third slave link 59, fourth slave link, e.g., angulation link 61, fifth slave link 63, sixth slave link 65, seventh slave link 67, and eighth slave link, e.g., slave hub 69, interconnected by a plurality of slave joints, e.g., first slave joint, e.g., proximal Scara joint 54, second slave joint, e.g., median Scara joint 56, third slave joint, e.g., distal Scara joint 58, fourth slave joint, e.g., angulation joint 60, fifth slave joint, e.g., alpha joint 62, sixth slave joint, e.g., beta joint 64, seventh slave joint, e.g., gamma joint 66, and eighth slave joint, e.g., theta joint 68. As shown in FIG. 12, translational instrument interface 81 is coupled to slave telemanipulator 51*a* via theta joint 68.

Translational instrument interface 81 may be constructed as described in U.S. Patent Application Publication No. 2018/0353252 to Chassot, assigned to the assignee of the instant application, the entire contents of which are incorporated by reference herein. For example, translational instrument interface 81 includes slave hub 69 and a surgical instrument. As shown in FIG. 11B, slave hub 69 may be affixed to link 67 of slave telemanipulator 51*a*. The surgical instrument includes the end-effector disposed at the distal end of the shaft of the surgical instrument, and may be coupled to slave hub 69. For example, the end-effector may be removeably coupled to slave hub 69. A sterile interface may be positioned between slave hub 69 and the surgical instrument. In addition, translational instrument interface 81 includes a translation transmission system that extends from one or more actuators positioned within slave hub 69 to the components of the end-effector. For example, the end-effector includes a plurality of end-effector links interconnected by a plurality of end-effector joints coupled to the translation transmission system of translational instrument interface 81, such that actuation of the translation transmission system by the one or more actuators causes movement of the end-effector via the plurality of end-effector links and joints.

In addition, slave telemanipulator 51*a* includes base portion 52 having and adjustable column, and slave support 53 fixed atop the adjustable column. Link 55 is rotatably coupled to slave support 53 via proximal Scara joint 54. Thus, link 55, and accordingly all the slave joints and links distal to link 55, may rotate relative to slave support 53 about axis $\delta_1$ at proximal Scara joint 54. As shown in FIG. 12, link 57, and accordingly all the slave joints and links distal to link 57, may rotate relative to link 55 about axis $\omega_2$ at median Scara joint 56, link 59, and accordingly all the slave joints and links distal to link 59, may rotate relative to link 57 about axis $\omega_3$ at distal Scara joint 58, angulation link 61, and according all the slave joints and links distal to angulation link 61, may rotate relative to link 59 about axis $\omega_4$ at angulation joint 60, link 63, and accordingly all the slave joints and links distal to link 63, may rotate relative to angulation link 61 about alpha axis $\omega_5$ at alpha joint 62, link 65, and accordingly all the slave joints and links distal to link 65, may rotate relative to link 63 about beta axis ω6 at beta joint 64, link 67, and accordingly all the slave joints and links distal to link 67, may rotate relative to link 65 about gamma axis $\omega_7$ at gamma joint 66, and slave hub 69, and accordingly translational instrument interface 81 when translational instrument interface 81 is coupled to slave hub 69, may rotate relative to link 67 about theta axis $\omega_8$ at theta joint 68.

The column integrated into slave support 53 contains an actuator, e.g., an electric motor, that allows for extending and retracting the column, thereby adjusting the height of all links distal to slave support 53 relative to the ground. Alternatively, instead of a column integrated into slave support 53, slave support 53 may include a mechanical linear guidance system having a counter-balance system based on a counter-weight, and an electric brake to block the vertical movement. Accordingly, when the electric brake is released, the vertical height of all links distal to slave support 53 may be adjusted relative to the ground. Proximal Scara joint 54, median Scara joint 56, and distal Scara joint 58 each contain an electric brake that may block the movement of the corresponding joint when the respective brake is engaged and permit manual movement of the respective joint when the respective brake is released. Angulation joint 60 contains an actuator, e.g., an electromagnetic motor, that allows for adjustment of the angular position of link 61 about link 59. Alpha joint 62, beta joint 64, gamma joint 66, and theta joint 68 are each linked to a dedicated electromagnetic motor and brake pair such that the control system may adjust the angular position of each joint by applying a position command to the respective motor, and stop any movement of the joint by activating the respective brake.

As will be understood by a person having ordinary skill in the art, slave console 50 may include a plurality of sensors and master console 20 may include a plurality of actuators such that movement applied at slave console 50 may cause movement to be applied at master console 20, thereby providing tactile feedback.

Figure 13:
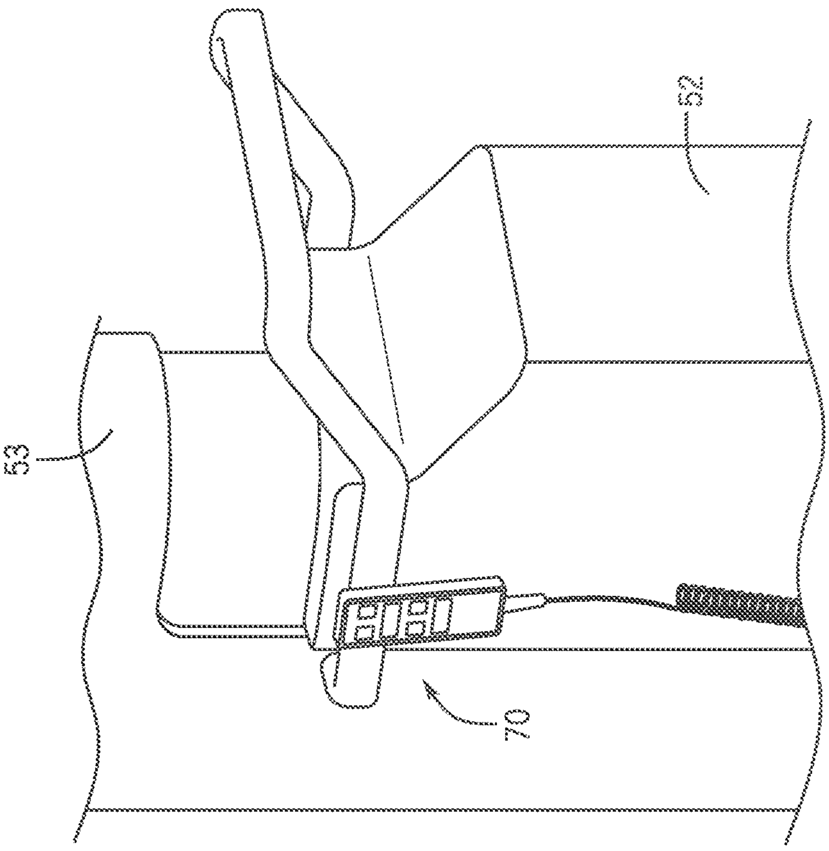
FIG. 13 shows an exemplary controller of the remotely actuated surgical robot system.
Figure 14C:
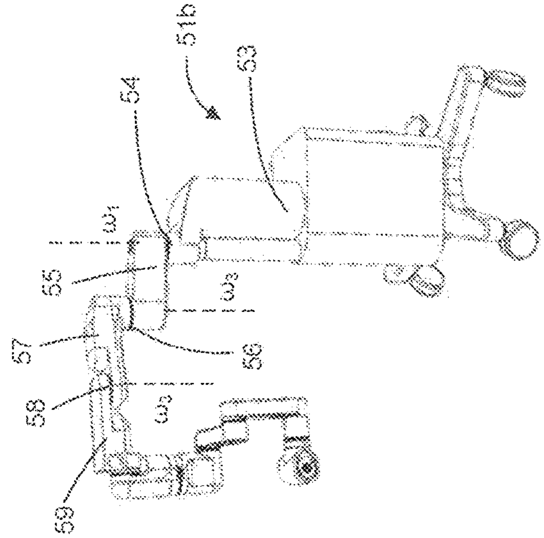
FIGS. 14A-14E show Scara movement of the slave console in accordance with the principles of the present invention.
Figure 14E:
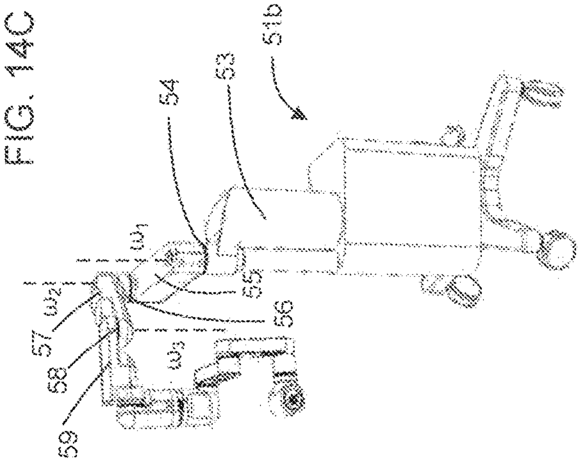
Figure 14B:
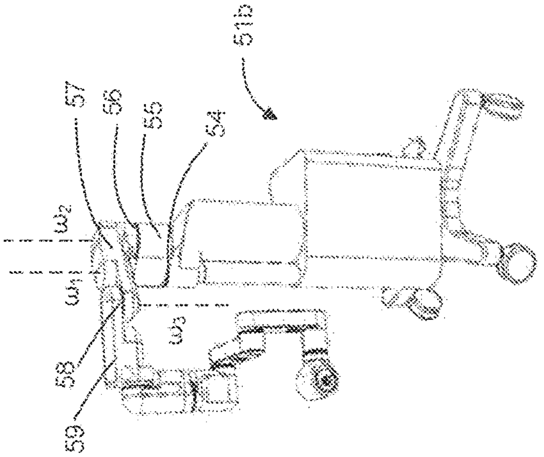
Figure 14D:
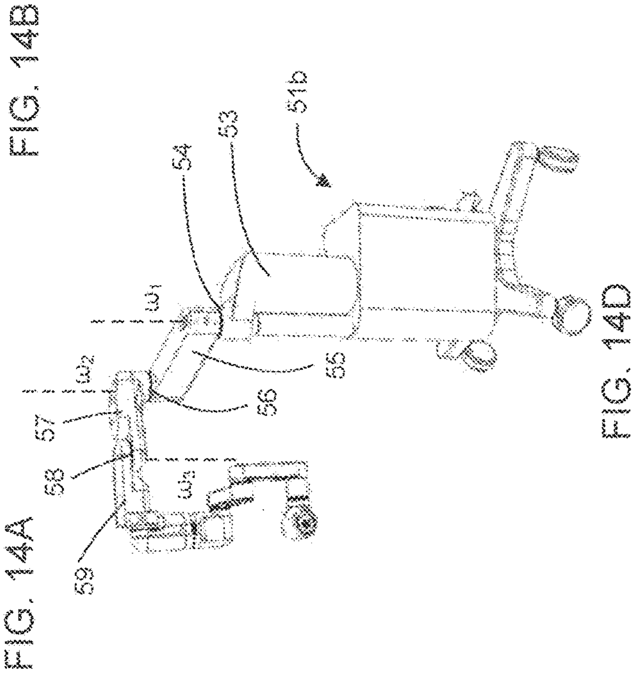
Figure 14A:
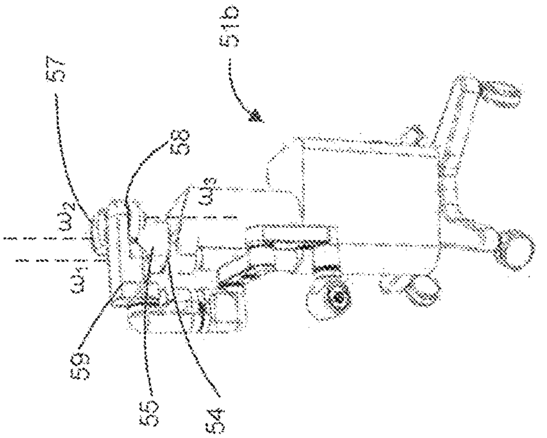

Referring now to FIG. 13, controller 70 is described. Controller 70 may be a remote controller or a graphical user interface operatively coupled to the control system of surgical robot system 10, or a series of actuators integrated into the left and right telemanipulator 51*a* and 51*b*, respectively. Accordingly, controller 70 may include a plurality of actuators, e.g., buttons, or a touchscreen interface whereby a user may select a plurality of options via touch. For example, controller 70 may provide a user with the option to select at least one of the following commands: Scara brake engagement and release, vertical adjustment of slave console, vertical column brake release, home configuration, increase and decrease the forward angulation, flipping from forward to reverse gear or from reverse gear to forward gear, laparoscopic configuration, and park position configuration. Controller 70 is operatively coupled to one or both slave controllers and/or the master controller. Responsive to user input at controller 70, the respective slave controller executes instructions stored thereon to execute the command (s) explained below inputted by the user. Each slave console may include its own dedicated controller 70 or a common controller 70 may be used for both slave consoles.

For example, as illustrated in FIGS. 14A-14E, controller 70 may permit a user to release the brakes in proximal Scara joint 54, median Scara joint 56, and distal Scara joint 56 so that the surgeon may manually reposition the slave arm horizontally by grabbing, holding and pushing/pulling the slave arm links distal to proximal Scara joint 54 while slave support 53 of the slave telemanipulator remains stationary. Specifically, during Scara movement, slave links 55, 57, 59 are permitted to move about axes $\omega_1$, $\omega_2$, $\omega_3$, at joints 54, 56, and 58, while slave support 53 of the slave telemanipulator remains stationary, and while the slave joints and link distal to slave link 59 are fixed relative to slave link 59. Accordingly, the user may adjust the distal end of the slave telemanipulator, e.g., slave hub 69, to a desired position over the patient undergoing surgery.

Figure 15C:
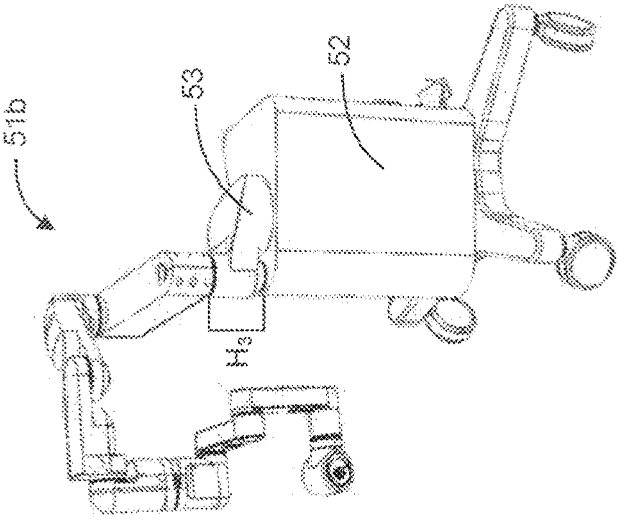
FIGS. 15A-15C show vertical adjustment of the slave console in accordance with the principles of the present invention.
Figure 15B:
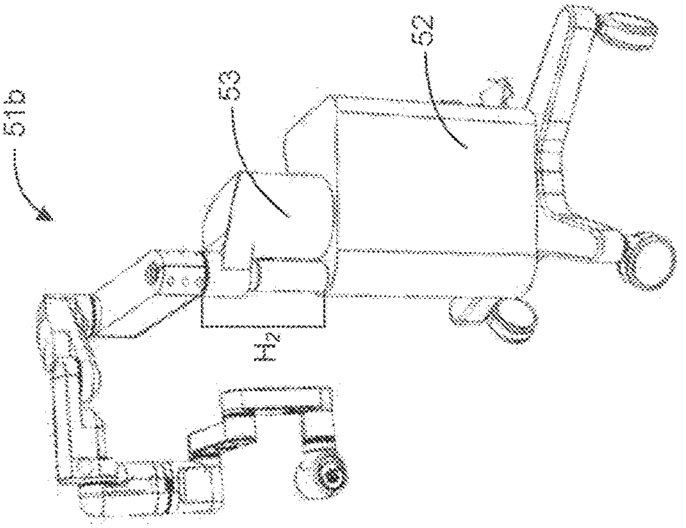
Figure 15A:
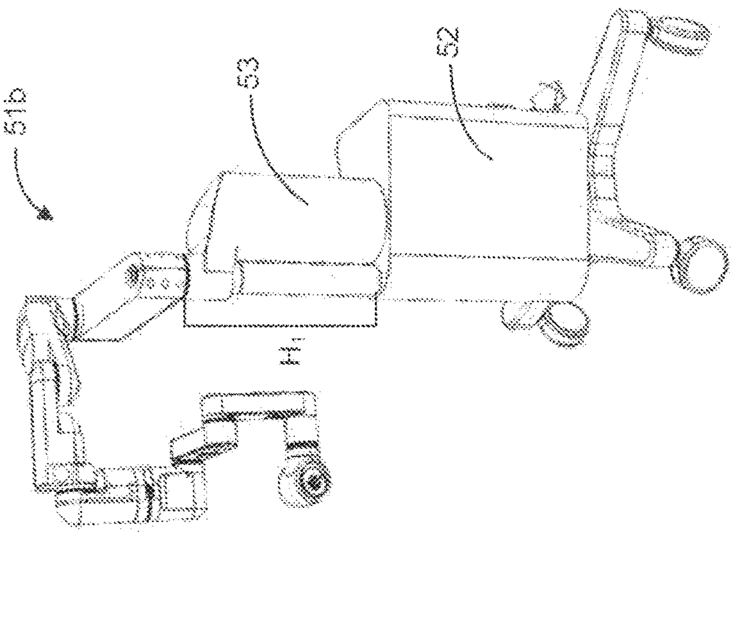

As illustrated in FIGS. 15A-15C, controller 70 may permit a user to select a vertical adjustment of slave console command whereby the control system will execute instructions to cause the actuator, e.g., motor, coupled to the column in slave support 53 to extend or retract. Specifically, during vertical adjustment of the slave telemanipulator, the relative distance between slave link 55 and the top surface of base portion 52 of the slave telemanipulator may be adjusted. For example, as shown in FIG. 15A, the vertical distance between slave link 55 and the top surface of base portion 52 of the slave telemanipulator is $H_1$, as shown in FIG. 15B, the vertical distance between slave link 55 and the top surface of base portion 52 of the slave telemanipulator is $H_2$, and as shown in FIG. 15C, the vertical distance between slave link 55 and the top surface of base portion 52 of the slave telemanipulator is $H_3$. Accordingly, the user may adjust the relative distance between slave link 55 and the top surface of base portion 52 of the slave telemanipulator to a desired height over the patient undergoing surgery. In the embodiment where the slave console includes a mechanical linear guidance system having a counter-balance system based on a counter-weight, controller 70 may permit a user to select a vertical adjustment of slave console command whereby the control system will execute instructions to cause an electric brake in the column to be released so that the mechanically counter-balanced linear guidance system may move up or down, thereby adjusting the relative distance between slave link 55 and the top surface of base portion 52 of the slave telemanipulator to a desired height over the patient undergoing surgery.

Figure 16:
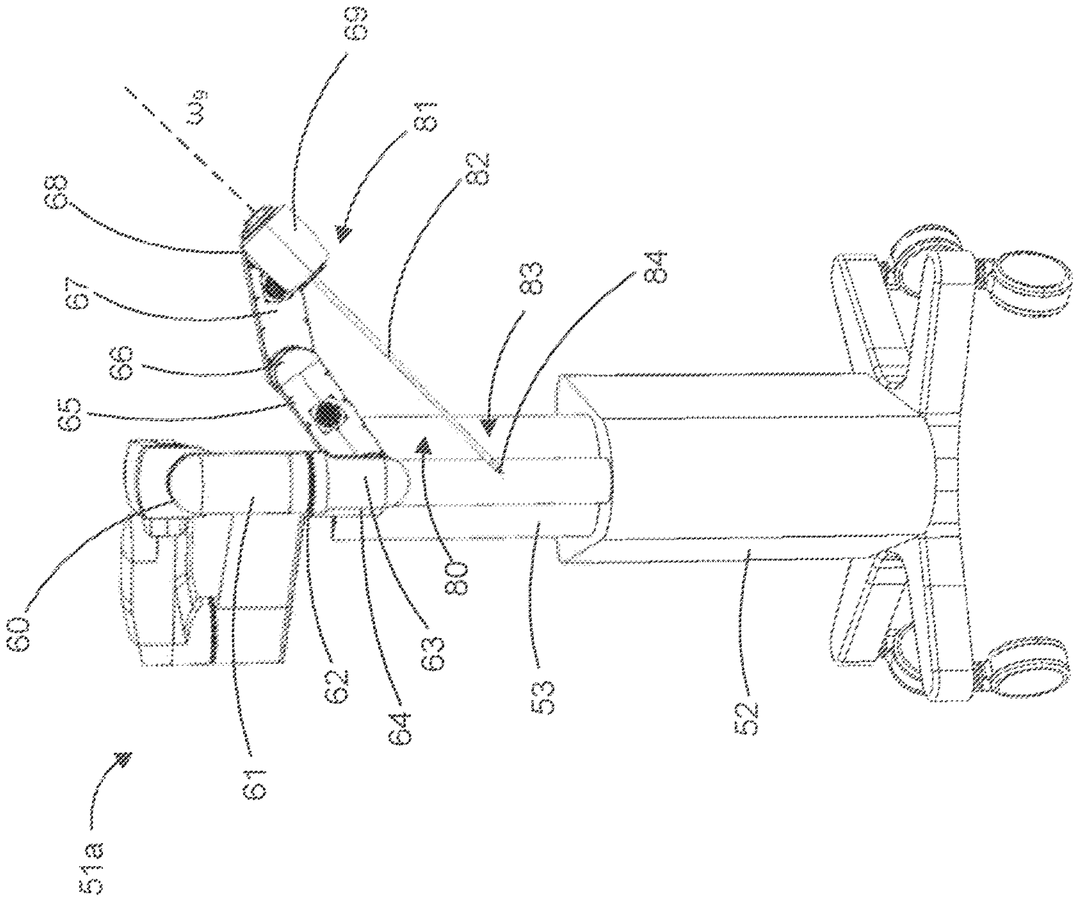
FIG. 16 shows the slave console in a home configuration in accordance with the principles of the present invention.
Figure 17A:
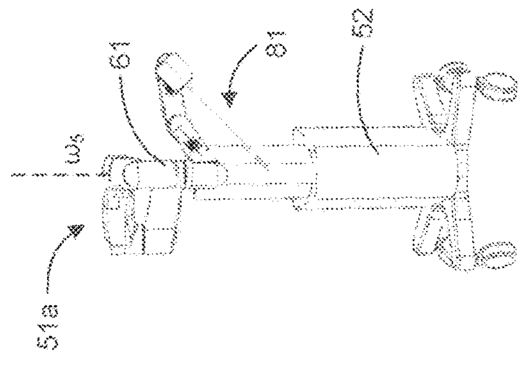
FIGS. 17A-17D show movement of an exemplary translational instrument interface coupled to the slave console in a forward configuration during zero-degree angulation of the slave console.
Figure 17B:
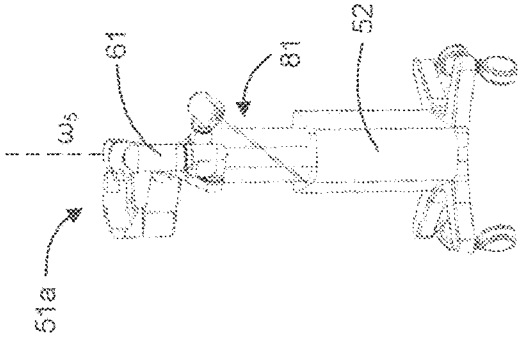
Figure 17C:
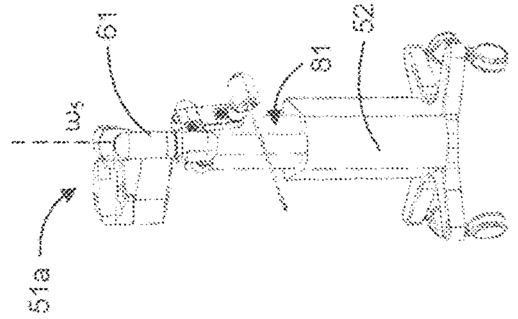
Figure 17D:
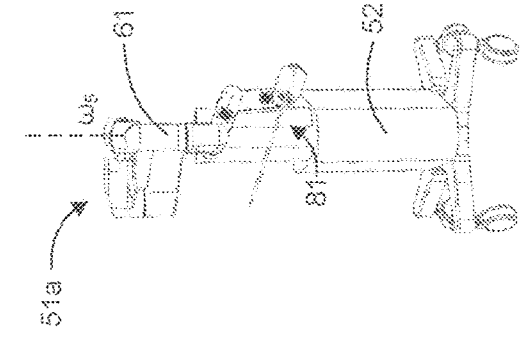

As illustrated in FIG. 16, controller 70 may permit a user to select a home configuration command whereby the control system will execute instructions to cause the actuators coupled to beta joint 64, gamma joint 66, and theta joint 68 to move the slave links and joints to a retracted position such that slave hub 69 of the slave telemanipulator is in a desirable position for positioning the shaft of translational instrument interface 81 within a trocar within the patient undergoing surgery. In the home position, slave hub 69 will be positioned relative to the trocar within the patient such that an instrument 82 may be inserted through and coupled to slave hub 69, such that instrument tip 84 will slide into, but not pass through the trocar, hence permitting the surgeon to insert the instrument safely and without the need for supervising the distal end of the trocar with the help of an endoscope.

In addition, controller 70 may permit a user to select an angulation command whereby the control system will execute instructions to cause the actuator coupled to angulation joint 60 to adjust the angulation of angulation link 61 about axis $\omega_4$ at angulation joint 60 to a desired angulation angle, e.g., between zero and 45-degrees relative to base 52 of slave telemanipulator 51*a*. Specifically, when the angulation command is actuated, angulation link 61, and accordingly all the slave links and joints distal to angulation link 61, will rotated about axis $\omega_4$ at angulation joint 60, while slave link 59 and all the slave links and joints proximal to slave link 59, and base portion 52 of the slave telemanipulator remains stationary. By adjusting the angulation angle of the slave telemanipulator, the angle of the surgical workspace of the slave telemanipulator will be adjusted, providing more access by the surgeon to the patient via translational instrument interface 81.

Figure 18A:
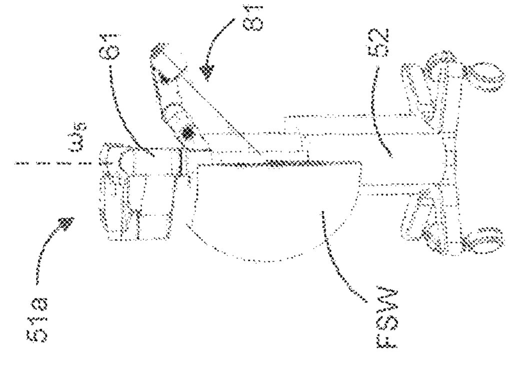
FIGS. 18A-18D illustrates the forward surgical workspace of FIGS. 17A-17D.
Figure 18B:
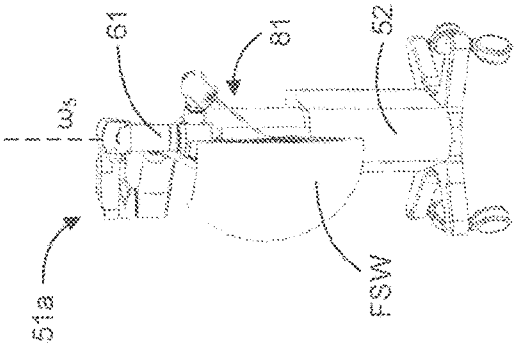
Figure 18C:
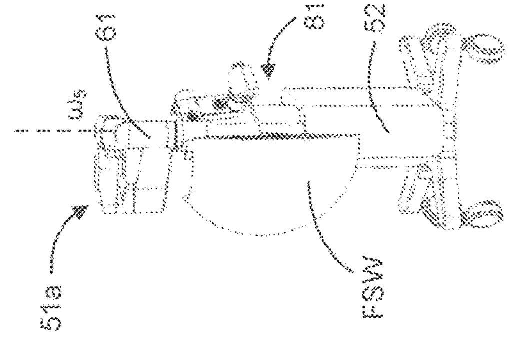
Figure 18D:
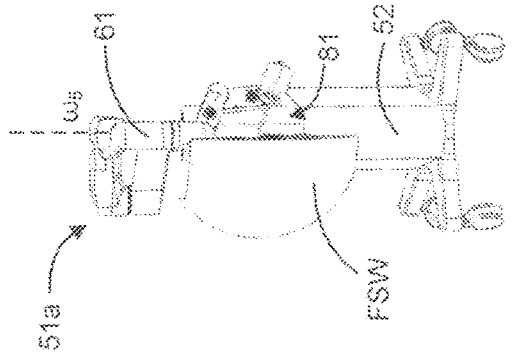
Figure 18E:
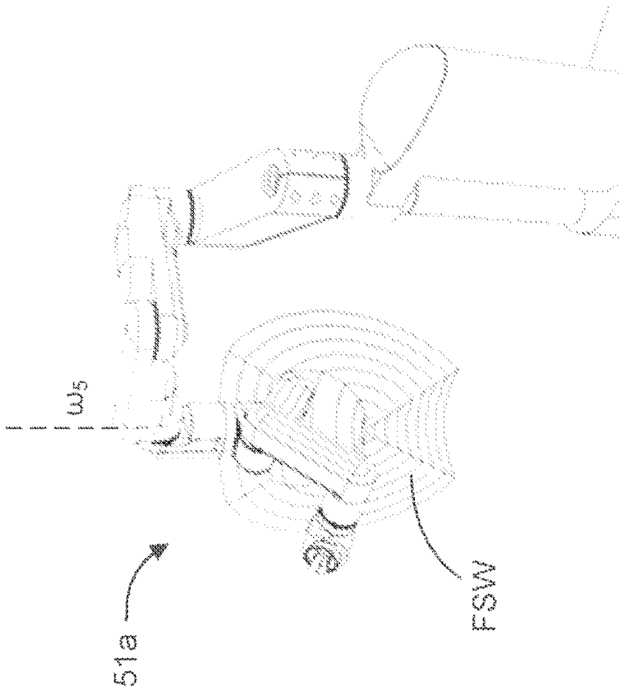
FIG. 18E is a back view of the forward surgical workspace of the slave console of FIGS. 18A-18D.

For example, FIGS. 17A-17D illustrate movement of translational instrument interface 81 coupled to slave telemanipulator 51*a* during zero-degree angulation of the slave console. As shown in FIGS. 17A-17D, angulation link 61, and accordingly angulation axis $\omega_5$, are parallel with the longitudinal axis of base 52 of slave telemanipulator 51*a*, and perpendicular with the ground floor. During operation of slave telemanipulator 51*a*, the control system only executes instructions to cause the actuators coupled to slave console 20 to apply movement to the slave links and joints distal to angulation link 61. Accordingly, as shown in FIGS. 18A-18D, translational instrument interface 81 of slave telemanipulator 51*a* has forward surgical workspace FSW, e.g., the extent to which translational instrument interface 81 can reach in a forward configuration during zero-degree angulation of the slave console. FIG. 18E is a back view of forward surgical workspace FSW of the slave console of FIGS. 18A-18D.

Figure 19C:
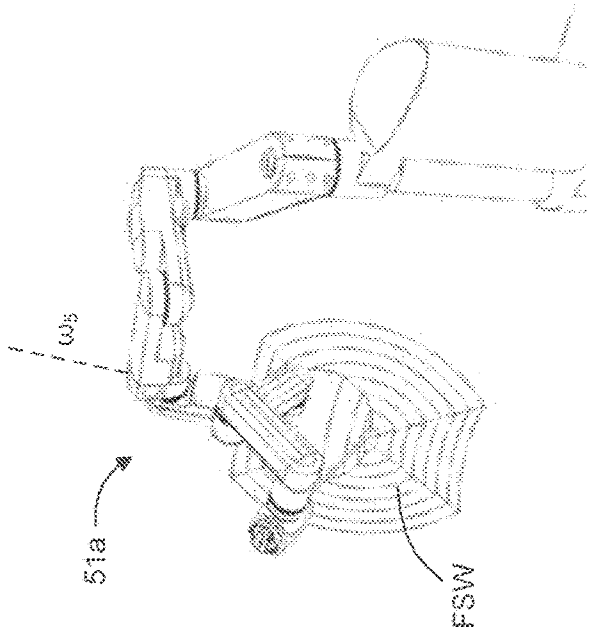
FIGS. 19A-19C show the forward surgical workspace of an exemplary instrument coupled to the slave console in a forward configuration during twenty-degree angulation of the slave console.
Figure 19A:
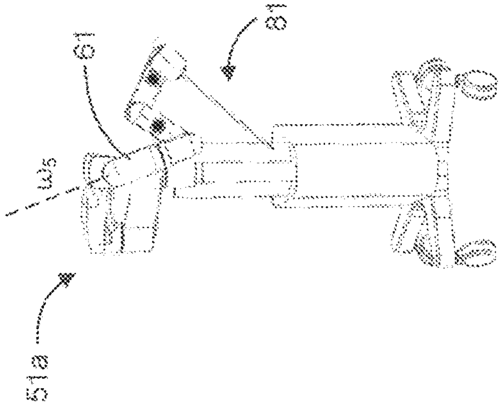
Figure 19B:
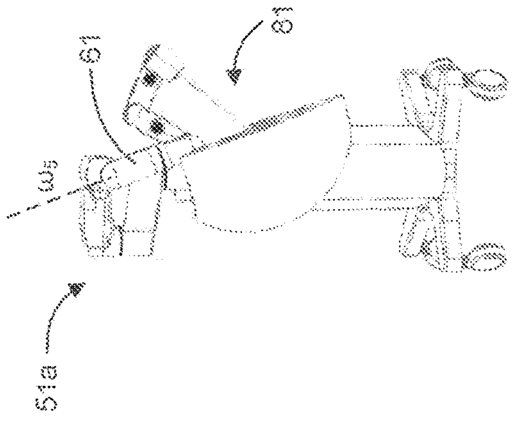

FIGS. 19A-19C illustrate movement of translational instrument interface 81 coupled to slave telemanipulator 51*a* during 20-degree angulation of the slave console. As shown in FIGS. 19A, angulation link 61, and accordingly angulation axis $\omega_5$, is adjusted to a 20-degree angle relative to the longitudinal axis of base 52 of slave telemanipulator 51*a*. During operation of slave telemanipulator 51*a*, the control system only executes instructions to cause the actuators coupled to slave console 20 to apply movement to the slave links and joints distal to angulation link 61. Accordingly, as shown in FIGS. 19B, translational instrument interface 81 of slave telemanipulator 51*a* has forward surgical workspace FSW, e.g., the extent to which translational instrument interface 81 can reach in a forward configuration during 20-degree angulation of the slave console. FIG. 19C is a back view of forward surgical workspace FSW of the slave console of FIG. 19B during 20-degree angulation of the slave console.

Figure 20A:
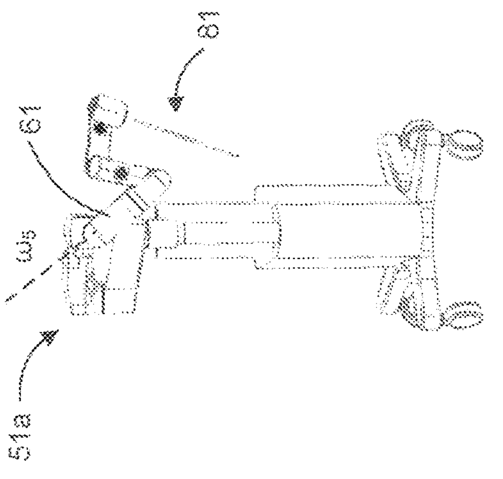
FIGS. 20A-20C show the forward surgical workspace of an exemplary instrument coupled to the slave console in a forward configuration during forty-degree angulation of the slave console.
Figure 20B:
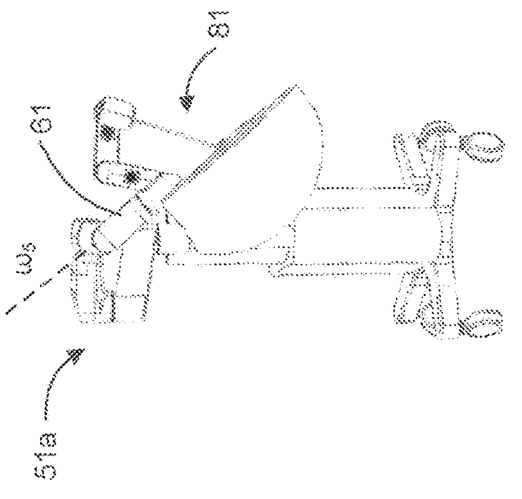
Figure 20C:
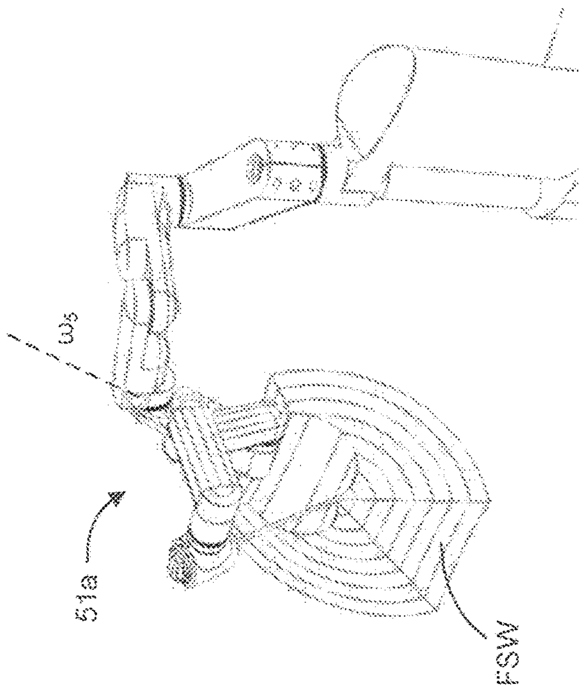

FIGS. 20A-20C illustrate movement of translational instrument interface 81 coupled to slave telemanipulator 51*a* during 40-degree angulation of the slave console. As shown in FIGS. 20A, angulation link 61, and accordingly angulation axis $\omega_5$, is adjusted to a 40-degree angle relative to the longitudinal axis of base 52 of slave telemanipulator 51*a*. During operation of slave telemanipulator 51*a*, the control system only executes instructions to cause the actuators coupled to slave console 20 to apply movement to the slave links and joints distal to angulation link 61. Accordingly, as shown in FIGS. 20B, translational instrument interface 81 of slave telemanipulator 51*a* has forward surgical workspace FSW, e.g., the extent to which translational instrument interface 81 can reach in a forward configuration during 40-degree angulation of the slave console. FIG. 20C is a back view of forward surgical workspace FSW of the slave console of FIG. 19B during 40-degree angulation of the slave console.

As illustrated in FIGS. 21A-21J, controller 70 may permit a user to select a flipping command whereby the control system will execute instructions to cause the plurality of actuators coupled to the slave console to move slave telemanipulator 51*a* between a forward surgical workspace and a reverse surgical workspace. For example, the control system may cause the plurality of actuators coupled to the slave console to invert slave telemanipulator 51*a* from a forward surgical workspace to a reverse surgical workspace, and vice versa. Specifically, during actuation of the flipping command, link 65, and accordingly all slave links and slave joints distal to link 65, are rotated about beta joint 64 of slave telemanipulator 51*a*. In addition, as link 65 rotates about beta joint 64, link 67 rotates relative to link 65 at gamma joint 66, and slave hub 69 rotates relative to link 67 about theta joint 68, until slave telemanipulator 51*a* is in a reverse surgical workspace configuration. As illustrated in FIGS. 21B-21H, translational instrument interface 81 is removed from slave hub 69 prior to actuation of the flipping command to prevent translational instrument interface 81 from injury the patient. As slave telemanipulator 51*a* is able to flip between a forward surgical workspace and a reverse surgical workspace by simply removing translational instrument interface 81 and actuating the flipping command without having to unlock slave telemanipulator 51*a* and move it about the operating room, and without having to actuate the Scara brake release command or the vertical adjustment of slave console command, the user will save a lot of time and be able to quickly continue operating on the patient in a different surgical workspace.

Figures 21A, 21B, 21C, 21D, 21E, 21F, 21G, 21H, 21I, 21J:
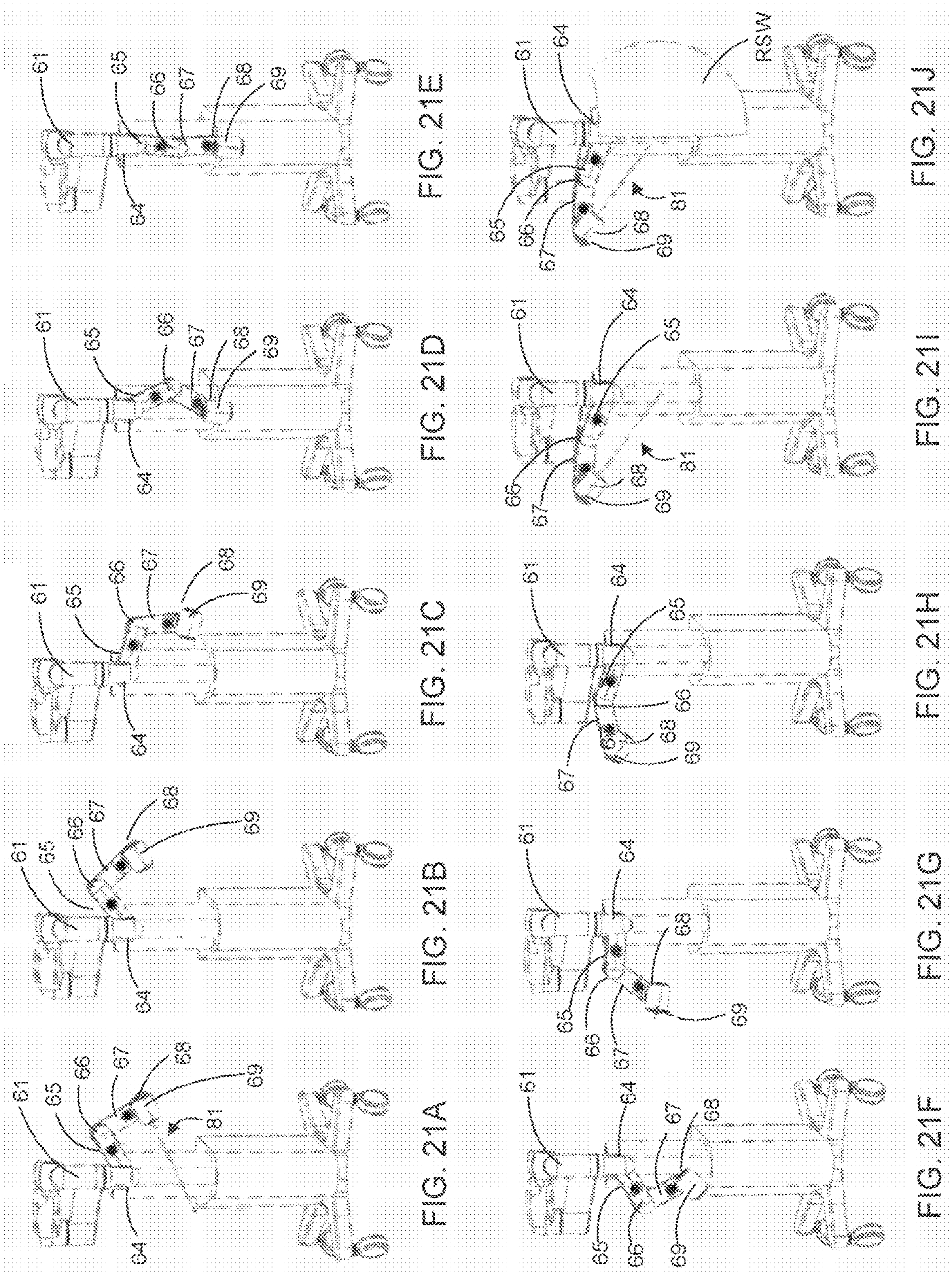
FIGS. 21A-21J show flipping of the slave console between a forward configuration and a reverse configuration in accordance with the principles of the present invention.
Figure 21K:
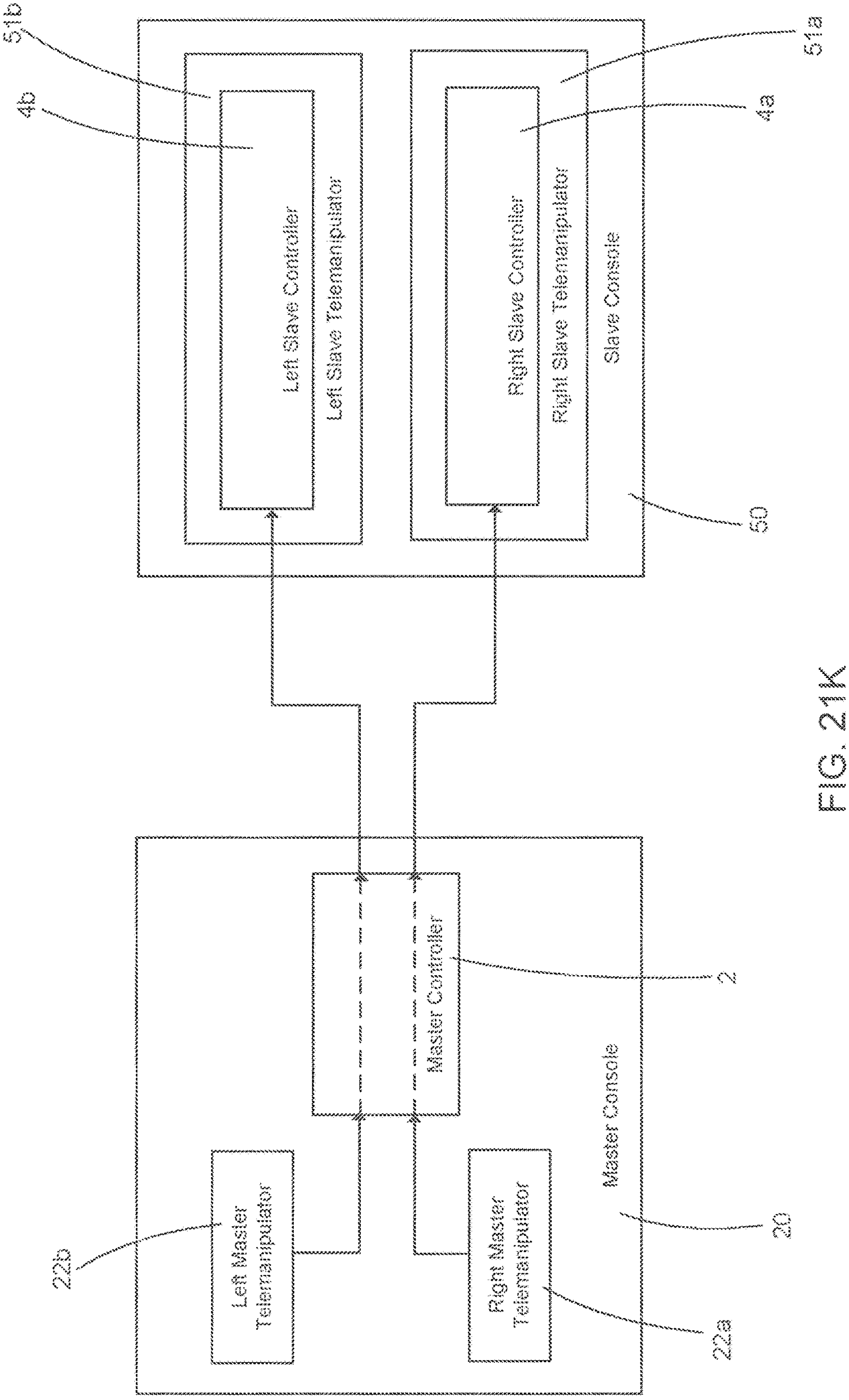
FIGS. 21K and 21L are a schematic of the master console and slave console during the forward configuration and the reverse configuration, respectively, in accordance with the principles of the present invention.
Figure 21L:
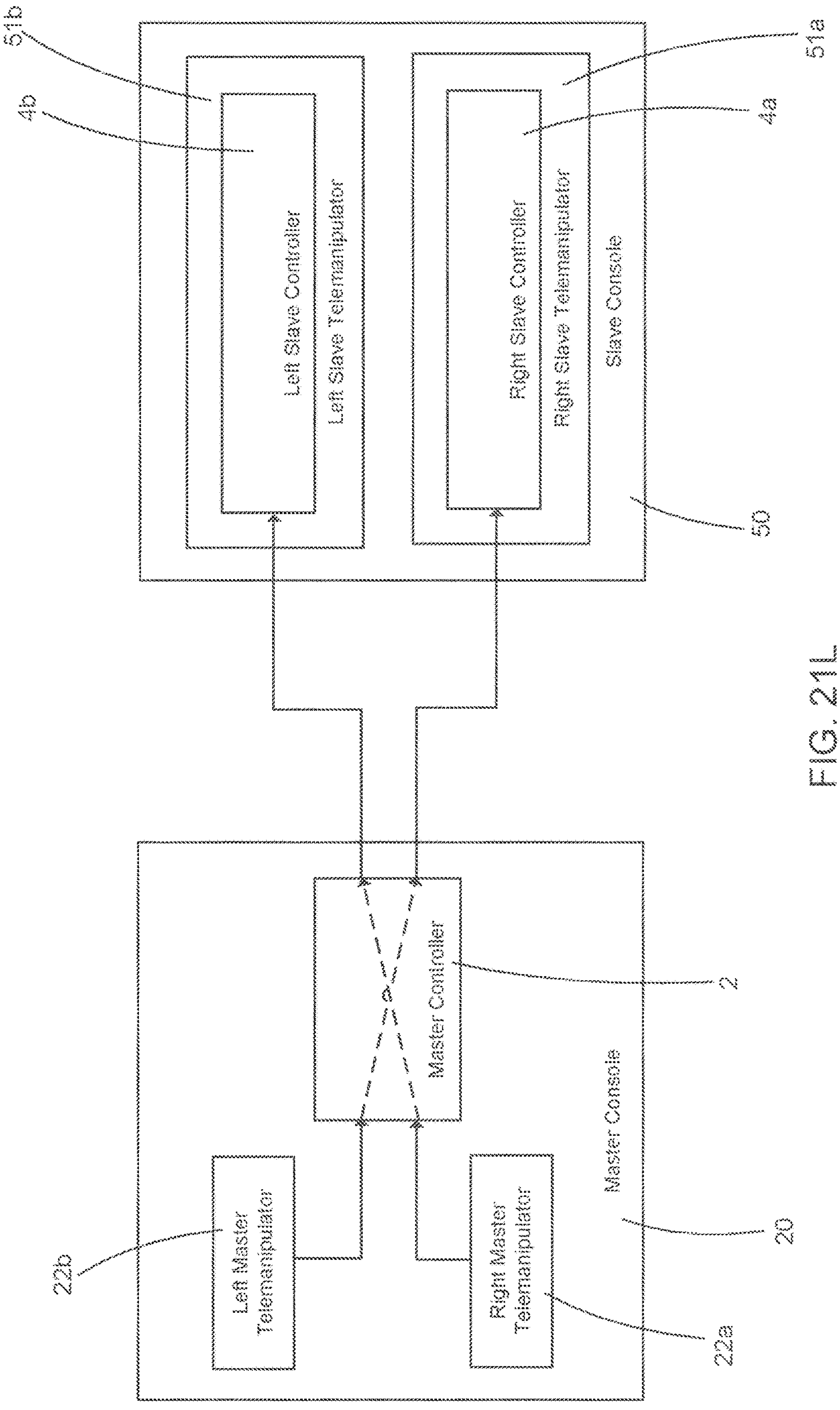

Referring now to FIGS. 21K and 21L, a schematic of the master console and slave console having a forward surgical workspace and a reverse surgical workspace, respectively, is provided. As shown in FIG. 21K, when the telemanipulators of slave console 50 have a forward surgical workspace, master controller 2 of master console 20 is programmed such that right master telemanipulator 22*a* communicates with right slave telemanipulator 51*a*, and left master telemanipulator 22*b* communicates with left slave telemanipulator 51*b*. Accordingly, master controller 2 may receive signals indicative of movement applied at right master telemanipulator 22*a* by the one or more sensors of master console 20, and execute instructions stored thereon to perform coordinate transforms necessary to activate the one or more actuators of slave console 50, send the processed signals to respective slave controllers 4*a* that execute instructions stored thereon to move right slave telemanipulator 51*a* in a manner corresponding to movement of right master telemanipulator 22*a* based on the processed signals. Similarly, master controller 2 may receive signals indicative of movement applied at left master telemanipulator 22*b* by the one or more sensors of master console 20, and execute instructions stored thereon to perform coordinate transforms necessary to activate the one or more actuators of slave console 50, send the processed signals to respective slave controllers 4*b* that execute instructions stored thereon to move left slave telemanipulator 51*b* in a manner corresponding to movement of left master telemanipulator 22*b* based on the processed signals.

As shown in FIG. 21L, when the telemanipulators of slave console 50 have a reverse surgical workspace, master controller 2 of master console 20 behaves as a switch board and is programmed such that right master telemanipulator 22*a* communicates with left slave telemanipulator 51*b*, and left master telemanipulator 22*b* communicates with right slave telemanipulator 51*a*. This is necessary so that the surgeon positioned at master console 20 and viewing the surgery site via display 21 may operate what appears to the surgeon as the "right" slave telemanipulator (left slave telemanipulator 51*b* in the reverse surgical workspace) with right master telemanipulator 22*a* and what appears to the surgeon as the "left" slave telemanipulator (right slave telemanipulator 51*a* in the reverse surgical workspace) with left master telemanipulator 22*a*. Accordingly, master controller 2 may receive signals indicative of movement applied at right master telemanipulator 22*a* by the one or more sensors of master console 20, and execute instructions stored thereon to perform coordinate transforms necessary to activate the one or more actuators of slave console 50, send the processed signals to respective slave controllers 4*b* that execute instructions stored thereon to move left slave telemanipulator 51*b* in a manner corresponding to movement of right master telemanipulator 22*a* based on the processed signals. Similarly, master controller 2 may receive signals indicative of movement applied at left master telemanipulator 22*b* by the one or more sensors of master console 20, and execute instructions stored thereon to perform coordinate transforms necessary to activate the one or more actuators of slave console 50, send the processed signals to respective slave controllers 4*a* that execute instructions stored thereon to move right slave telemanipulator 51*a* in a manner corresponding to movement of left master telemanipulator 22*b* based on the processed signals.

Thus, in the forward surgical workspace configuration, master controller 2 communicates with right slave controller 4*a* to cause right slave telemanipulator 51*a* to move responsive to movement at right master telemanipulator 22*a* and master controller 2 communicates with left slave controller 4*b* to cause left slave telemanipulator 51*b* to move responsive to movement at left master telemanipulator 22*b*. Additionally, in the reverse surgical workspace configuration, master controller 2 communicates with left slave controller 4*b* to cause left slave telemanipulator 51*b* to move responsive to movement at right master telemanipulator 22*a* and master controller 2 communicates with right slave controller 4*a* to cause right slave telemanipulator 51*a* to move responsive to movement at left master telemanipulator 22*b*.

Figure 22A:
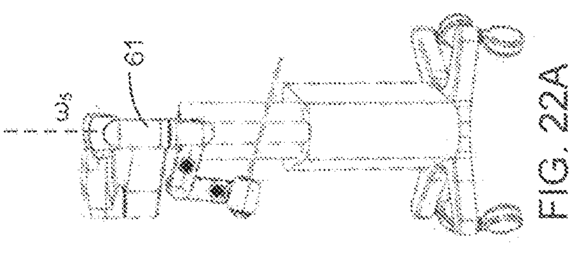
FIGS. 22A-22C show an exemplary translational instrument interface coupled to the slave console in a reverse configuration during zero, twenty, and forty-degree angulation, respectively, of the slave console.
Figure 22B:
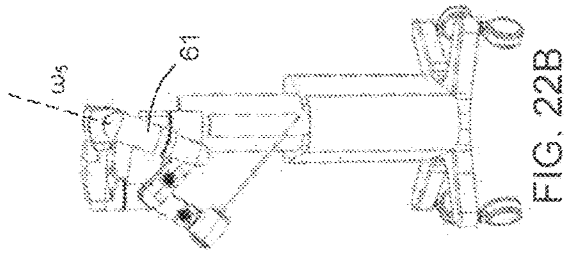
Figure 22C:
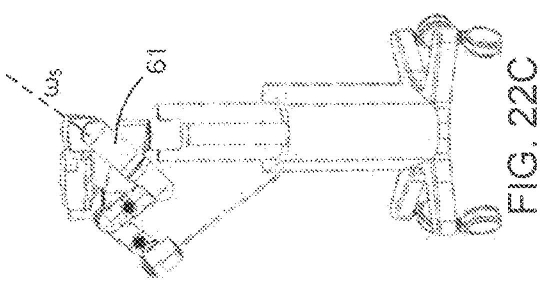
Figure 23A:
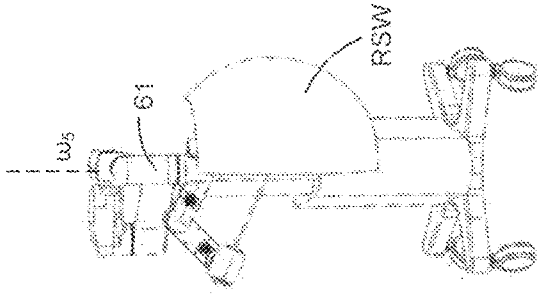
FIGS. 23A-23C illustrates the reverse surgical workspaces of FIGS. 22A-22C.
Figure 23B:
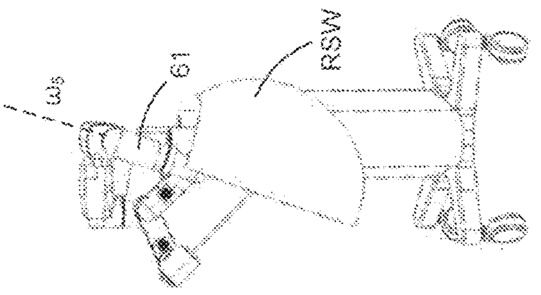
Figure 23C:
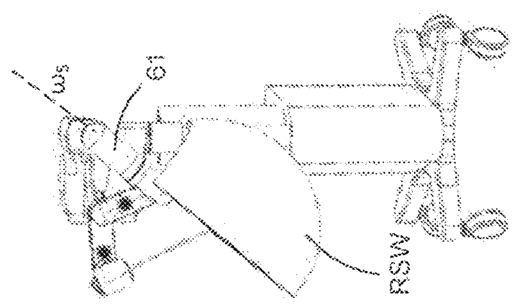

FIG. 22A illustrates slave telemanipulator 51*a* in a reverse configuration during zero-degree angulation of the slave console, FIG. 22B illustrates slave telemanipulator 51*a* in a reverse configuration during 20-degree angulation of the slave console, and FIG. 22C illustrates slave telemanipulator 51*a* in a reverse configuration during 40-degree angulation of the slave console. In addition, as shown in FIGS. 23A-23C, translational instrument interface 81 of slave telemanipulator 51*a* has reverse surgical workspace RSW, e.g., the extent to which translational instrument interface 81 can reach in a reverse configuration during zero-degree angulation, 20-degree angulation, and 40-degree angulation, respectively, of the slave console.

Figure 24A:
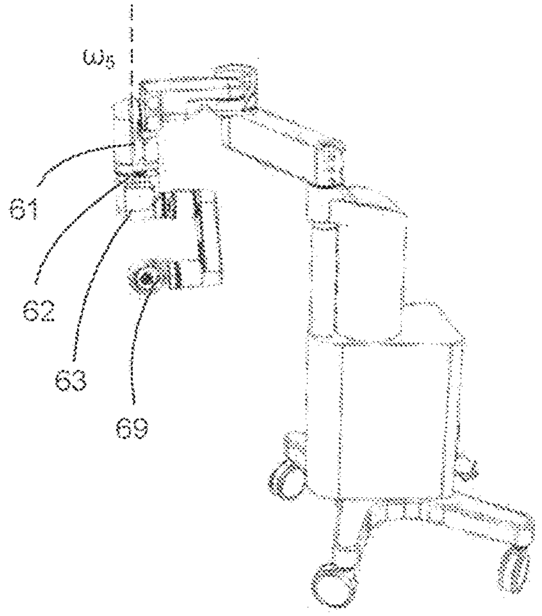
FIGS. 24A-24D show adjustment of the slave console for integrated laparoscopy in accordance with the principles of the present invention.
Figure 24B:
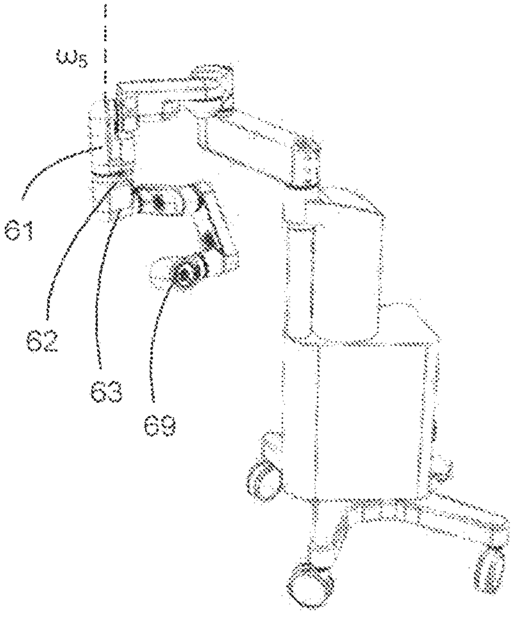
Figure 24C:
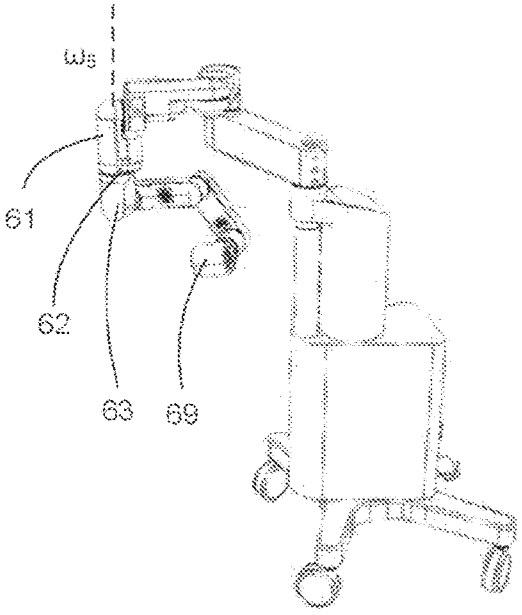
Figure 24D:
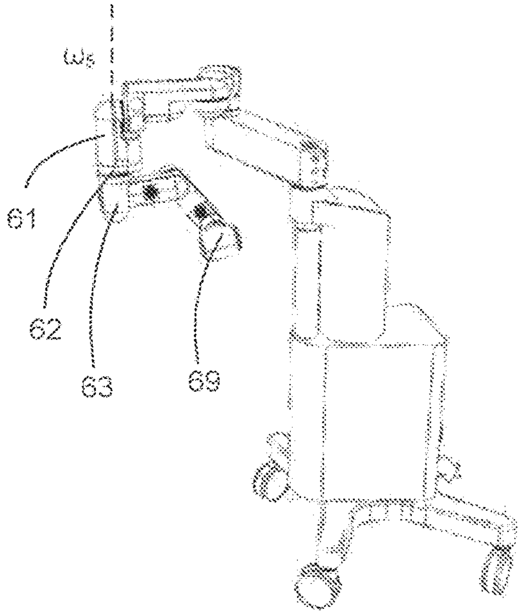

As illustrated in FIGS. 24A-24D, controller 70 may permit a user to select a laparoscopic configuration command whereby the control system will execute instructions to cause the plurality of actuators coupled to the slave console to move slave hub 69 away from the patient undergoing surgery so that the surgeon may quickly and safely move from master console 20 to the surgical site on the patient to manually perform laparoscopic tasks on the patient. Specifically, actuation of the laparoscopic configuration command causes link 63, and accordingly all the slave links and joints distal to link 63, to rotate about alpha axis $\omega_3$ at joint 62 while angulation link 61, and accordingly all the slave links and joints proximal to angulation link 61 including base 52 of slave telemanipulator 51*a* remain stationary, until slave hub 69 is facing away from the patient as shown in FIG. 24D. Accordingly, translational instrument interface 81 must be removed from slave hub 69 prior to actuation of the laparoscopic configuration command.

Figure 25:
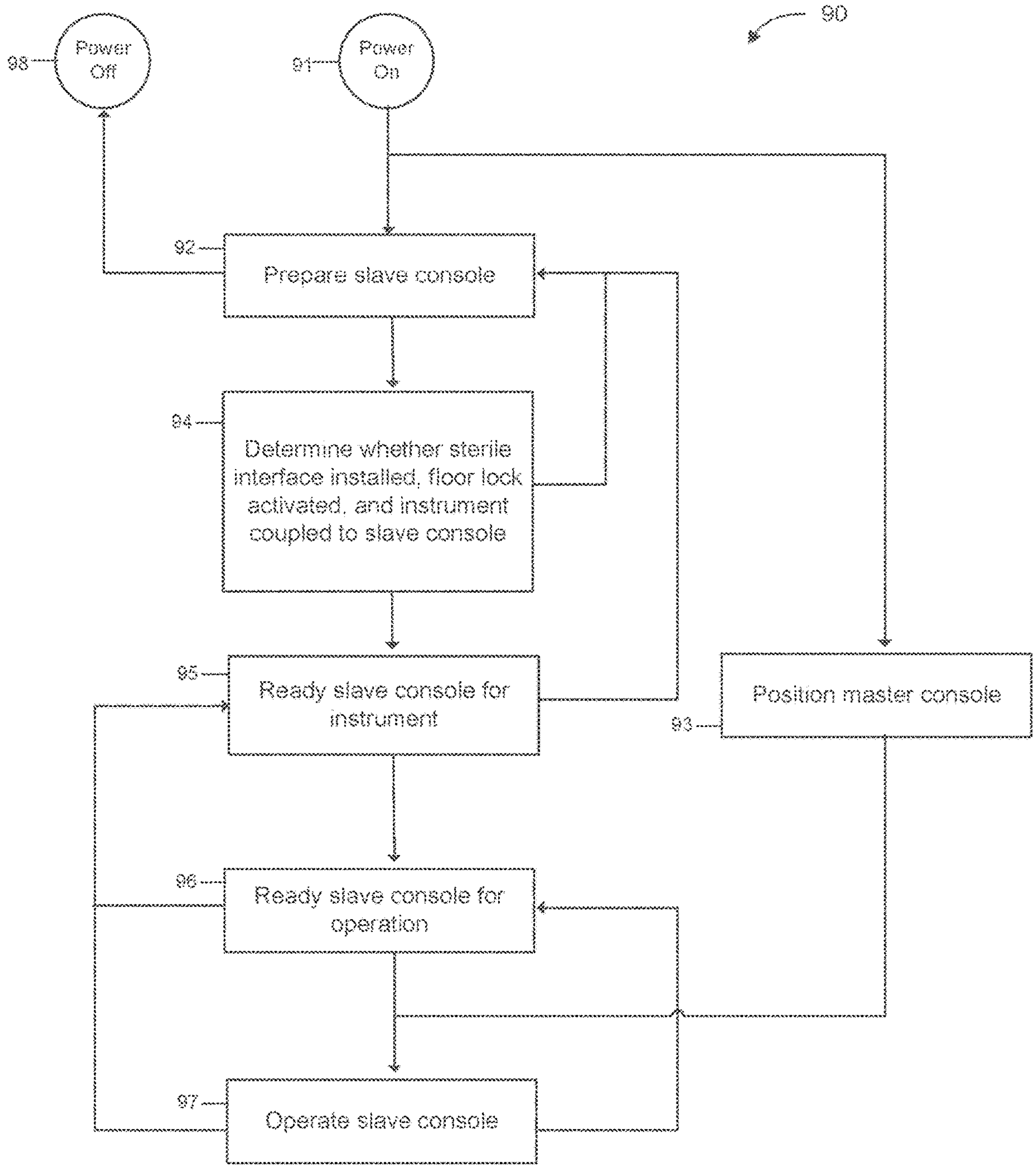
FIG. 25 is a flow chart illustrating use of the remotely actuated surgical robot system of FIG. 1 in accordance with the principles of the present invention.

Referring now to FIGS. 25-30, exemplary method 90 for using of surgical robot system 10 via the control system is described. As will be understood by one skilled in the art, the steps of the methods described herein may be executed by one or more processors of the control system (e.g., at the master controller, the first slave controller, and/or the second slave controller) that execute instructions stored in one or more memory components responsive to user input. As shown in FIG. 25, at step 91, system 10 is powered on. At step 92, slave console 50 is prepared to be ready for operating on the patient undergoing surgery as further illustrated in FIG. 27, and at step 93, master console 20 is positioned to the surgeon's desired configuration during operation as further illustrated in FIG. 26.

Figure 26:
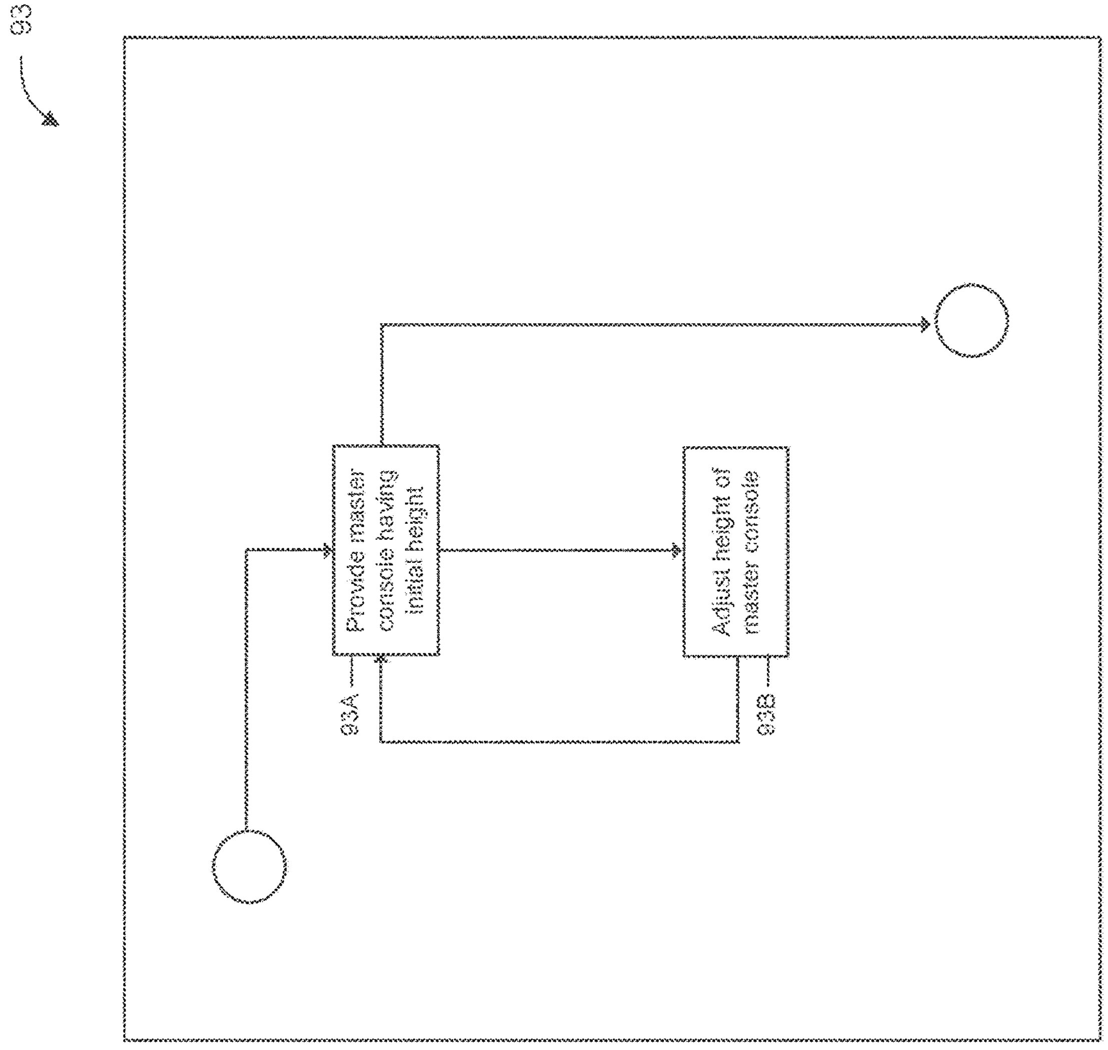
FIG. 26 is a flow chart illustrating the surgeon console positioning step of FIG. 25 in accordance with the principles of the present invention.

For example, FIG. 26 illustrates step 93 of positioning master console 20 to the surgeon's desired configuration. Master console 20 may be moved about the operating room via the wheels at its base while the wheels are unlocked. Upon reaching the desired location within the operating room, the wheel locks are activated to keep master console 20 in place. As shown in FIG. 26, at step 93A, the master telemanipulators are stationary and telescoping bases 23*a*, 23*b* have an initial height. A controller operatively coupled to master console 20, e.g., a button, may then be actuated to adjust the height of telescoping bases 23*a*, 23*b*, e.g., to increase or decrease the height of telescoping bases 23*a*, 23*b*, until master console 20 is at the surgeon's desired height at step 93B. For example, master console 20 may be adjusted to a seated configuration where the surgeon may be seated during operation of master console 20, or a standing configuration where the surgeon may be standing during operation of master console 20. Accordingly, the controller may be actuated to return master console 20 to the initial height, e.g., for storage purposes.

Figure 27:
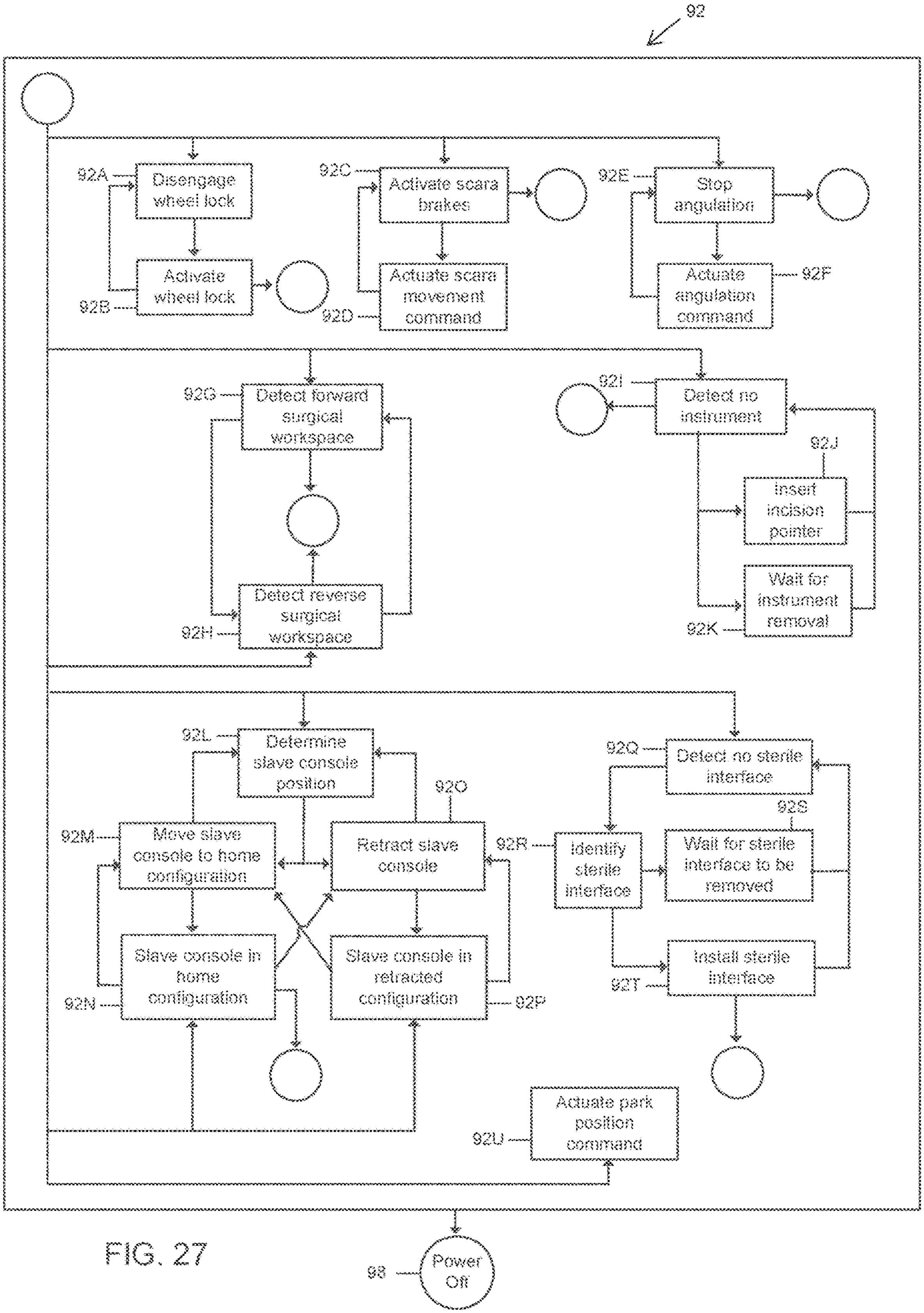
FIG. 27 is a flow chart illustrating the preparation step of FIG. 25 in accordance with the principles of the present invention.

Referring now to FIG. 27, step 92 of preparation of slave console 50 is described. As shown in FIG. 27, at step 92A, the wheel locks of the slave telemanipulator are disengaged such that slave console 50 may be moved about the operating room to the desired location relative to the patient. The wheel locks can only be disengaged when no instrument 82 is inserted into slave hub 69 so as to avoid injuring the patient. As multiple slave telemanipulators may be used, each slave telemanipulator is positioned during step 92A. When slave console 50 is in the desired position within the operating room adjacent the patient undergoing surgery, the wheel locks of slave console 50 are activated at step 92B such that slave console 50 is prevented from further movement about the operating room via its wheels. Accordingly, the wheel locks may be disengaged again at step 92A if slave console 50 needs to be moved to a different desired position.

At step 92C, the Scara brake release command has not been actuated and Scara brakes of slave console 50 are on. At step 92D, the Scara brake release command may be actuated by the user to position the distal end of the slave telemanipulator, e.g., the slave links distal to link 59, at a desired position over the patient undergoing surgery. Specifically, upon actuation of the Scara brake release command, slave links 55, 57, 59 are permitted to move about axes $\omega_1$, $\omega_2$, $\omega_3$, at joints 54, 56, and 58, while slave support 53 of the slave telemanipulator remains stationary, and while the slave joints and link distal to slave link 59 are fixed relative to slave link 59. When the distal end of the slave telemanipulator is in the desired positioned over the patient, actuation of the Scara brake release command ceases at step 92C. In addition, as described above with reference to FIGS. 15A-15C, the vertical height of the slave telemanipulators may be adjusted such that the distal end of the slave telemanipulator is at a desired height relative to the trocar within the patient. The Scara brake release command can only be enabled when no instrument 82 is present in slave hub 69 so as to avoid injuring the patient.

Referring again to FIG. 27, at step 92E, angulation link 61 of the slave telemanipulator is stationary relative to slave link 59. For example, the slave telemanipulator may initially have an angulation angle of zero degrees. At step 92F, the angulation command may be actuated to adjust the angulation of angulation link 61 about axis $\omega_4$ at angulation joint 60 to a desired angulation angle, e.g., between zero and 45-degrees relative to base 52 of slave telemanipulator 51*a*. Specifically, upon actuation of the angulation command, angulation link 61, and accordingly all the slave links and joints distal to angulation link 61, will rotated about axis $\omega_4$ at angulation joint 60, while slave link 59 and all the slave links and joints proximal to slave link 59, and base portion 52 of the slave telemanipulator remains stationary. When the desired angle of angulation of the slave telemanipulator is achieved, actuation of the angulation command ceases at step 92E such that angulation link 61 of the slave telemanipulator is stationary relative to slave link 59. The angulation command may have two buttons, one to increase and another one to decrease the angulation.

At step 92G, the slave telemanipulator has a forward surgical workspace, or alternatively, at step 92H, the slave telemanipulator has a reverse surgical workspace. During both steps 92G and 92H, instrument 82 cannot be in slave hub 69. If the slave telemanipulator has a forward surgical workspace at step 92G, and the user desires a reverse surgical workspace, the flipping command may be actuated to invert slave telemanipulator 51*a* from a forward surgical workspace to a reverse surgical workspace. Specifically, upon actuation of the flipping command, link 65, and accordingly all slave links and slave joints distal to link 65, are rotated about beta joint 64 of slave telemanipulator 51*a*. In addition, as link 65 rotates about beta joint 64, link 67 rotates relative to link 65 at gamma joint 66, and slave hub 69 rotates relative to link 67 about theta joint 68, until slave telemanipulator 51*a* is in a reverse surgical workspace configuration. Similarly, if the slave telemanipulator has a reverse surgical workspace at step 92H, and the user desires a forward surgical workspace, the flipping command may be actuated to invert slave telemanipulator 51*a* from a forward surgical workspace to a reverse surgical workspace.

At step 92I, translational instrument interface 81 is not coupled to slave hub 69 of the slave telemanipulator. At step 92J, a temporary incision pointer may be removeably coupled to the slave telemanipulator. For example, the temporary incision pointer is removeably coupled to the slave telemanipulator such that it points to virtual remote center-of-motion V located at a predetermined point on axis $\omega_5$, such that virtual remote center-of-motion V may be brought in coincidence with the surgical incision point, reducing trauma to the patient and improving cosmetic outcomes of the surgery. The temporary incision pointer may be removed prior to installation of the translational instrument interface 81 if necessary. During preparation step 92, instrument 82 should not be coupled to slave hub 69 of the slave telemanipulator. Thus, if instrument 82 is coupled to slave hub 69 of the slave telemanipulator, at step 92K, the control system will prevent further actions until translational instrument interface 81 is removed.

At step 92L, the slave links and joints distal to link 61 of the slave telemanipulator may be in any position. Accordingly, at step 92M, the home configuration command may be actuated to move the slave links and joints to a retracted position such that slave hub 69 of the slave telemanipulator is in a desirable position for positioning instrument tip 84 within a trocar within the patient undergoing surgery. At step 92N, the slave telemanipulator is in the home position, wherein slave hub 69 is positioned relative to the trocar within the patient such that instrument 82 may be inserted through and coupled to slave hub 69, and the instrument tip 84 will slide into, but not pass through the trocar.

At step 92O, the laparoscopic configuration command may be actuated to move slave hub 69 away from the patient undergoing surgery so that the surgeon may quickly and safely move from master console 20 to the surgical site on the patient to manually perform laparoscopic tasks on the patient. Specifically, upon actuation of the laparoscopic configuration command, link 63, and accordingly all the slave links and joints distal to link 63, to rotate about alpha axis $\omega_3$ at joint 62 while angulation link 61, and accordingly all the slave links and joints proximal to angulation link 61 including base 52 of slave telemanipulator 51*a* remain stationary, until slave hub 69 is facing away from the patient. At step 92P, slave hub 69 is in the retracted position.

At step 92Q, the sterile interface of translational instrument interface 81 is not coupled to slave hub 69 of the slave telemanipulator. At step 92R, the sterile interface is coupled to the slave hub, and the control system determines whether the sterile interface is identified, e.g., by reading an RFID tag integrated into the sterile interface. If the sterile interface is not identified, at step 92S, the control system awaits removal of the sterile interface until the sterile interface is decoupled from slave hub 69 at step 92Q. If the sterile interface is identified, the sterile interface is successfully installed at step 92T.

At step 92U, the park position command may be actuated to move slave telemanipulator 51*b* into a position suitable for transportation and storage. Specifically, upon actuation of the park position command, the vertical column in slave support 53 retracts to a minimum height, the Scara brakes release to fold the Scara arm into a folded position, the angulation returns to zero-degree angulation, and the joints distal to joint 62 move to fold the slave arm into a compact position. Surgical robot system 10 may be powered off if necessary after step 92.

If surgical robot system 10 is not powered off after step 92, at step 94, the control system determines whether the sterile interface has been successfully installed and whether the floor lock is activated. If it is determined that either the sterile interface has not been successfully installed or that the floor lock is disengaged, surgical robot system 10 must return to preparation step 92 to rectify the above. If it is determined at step 94 that the sterile interface has been successfully installed and that the floor lock is activated, surgical robot system 10 may proceed to step 95.

Figure 28:
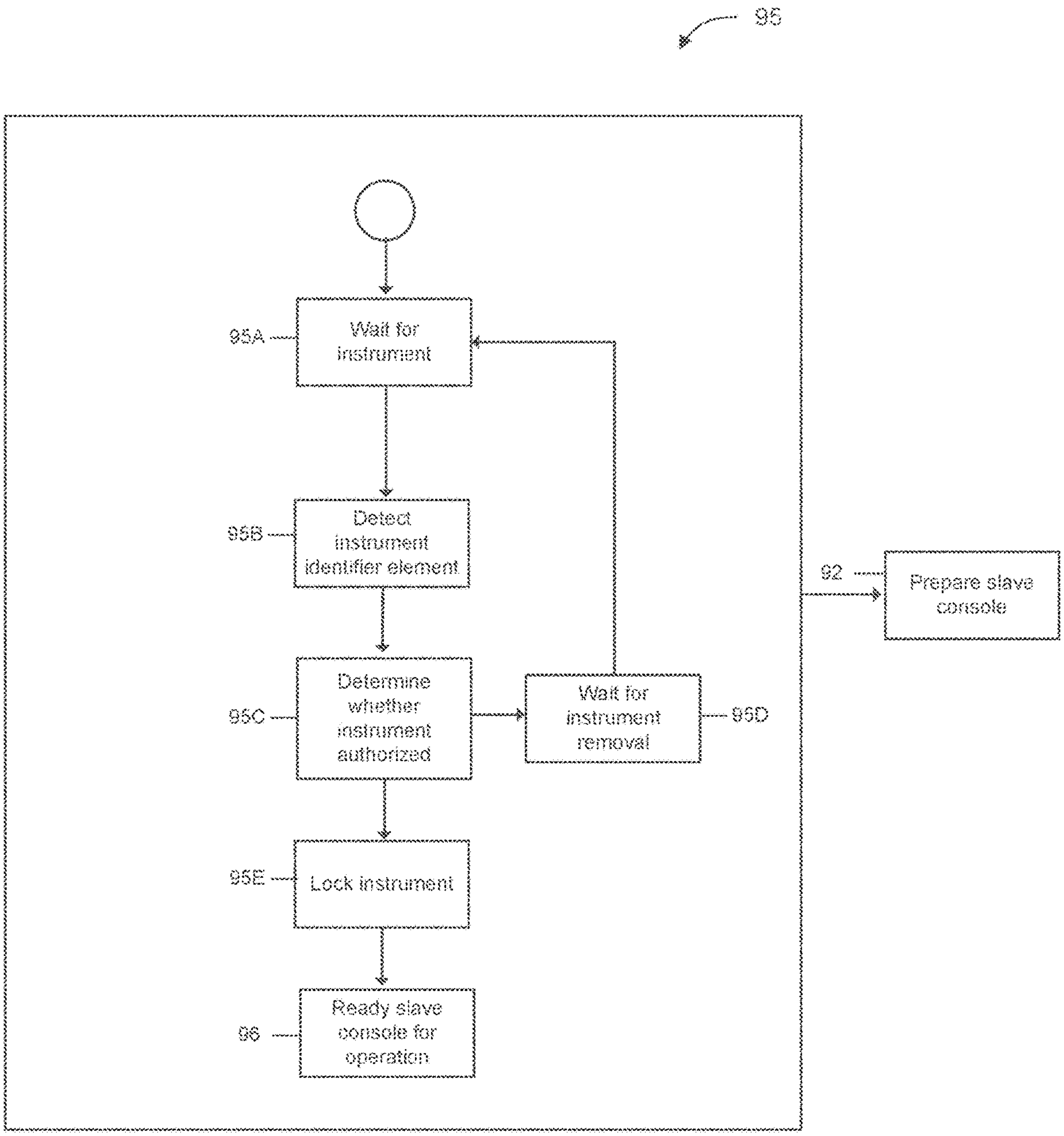
FIG. 28 is a flow chart illustrating the ready for instrument step of FIG. 25 in accordance with the principles of the present invention.

At step 95, surgical robot system is ready for instrument 82 as shown in FIG. 28. For example, at step 95A, the control system of slave console 50 waits for instrument 82 until instrument 82 is coupled to slave hub 69 of the slave telemanipulator. Accordingly, an instrument 82 is selected and inserted within slave hub 69. To ensure that the instrument doesn't fall out of the slave hub, the user may mechanically lock the instrument into slave hub 69 by rotating the proximal end of the instrument. Slave hub 69 has an integrated sensor to detect whether the instrument is locked. At step 95B, sensors positioned within slave hub 69 read out an identifier element integrated with the selected instrument, e.g., an RFID tag, where the RFID tag contains identification information of the selected instrument. At step 95C, the control system determines whether the selected instrument is authorized based on the detection of the RFID tag. If the selected instrument is not authorized, the control system waits until it is removed at step 95D. When the unauthorized instrument is removed, step 95D returns to step 95A. If the selected instrument is authorized and locked within slave hub 69 of the slave telemanipulator at step 95E, method 90 may proceed to step 96. If at any time during step 95 the sterile interface is removed, the floor lock is disengaged, the flipping command is actuated, the Scara brake release command is actuated, the home configuration command is actuated, or the incision pointer is inserted, method 90 may return to preparation step 92.

Figure 29:
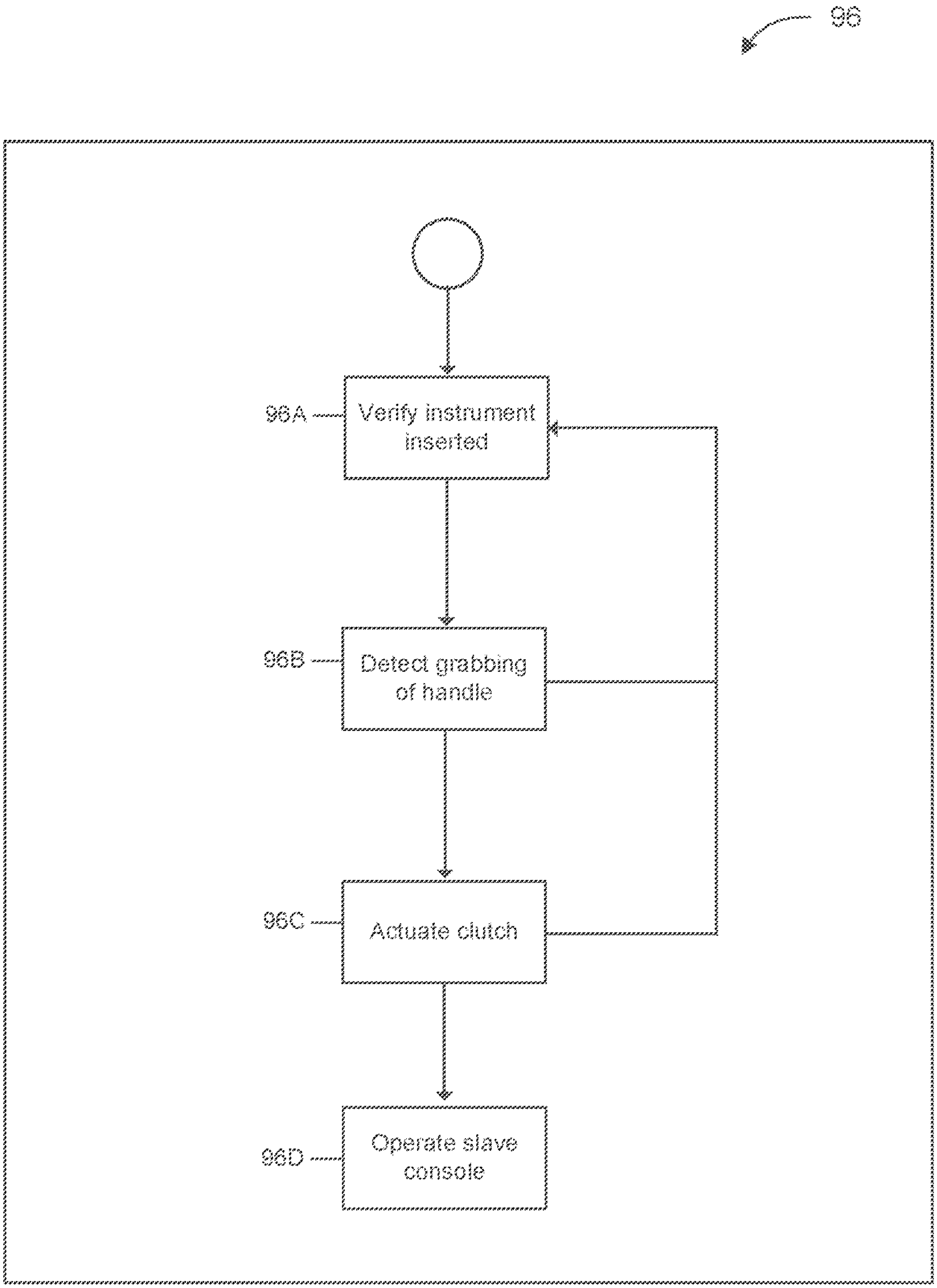
FIG. 29 is a flow chart illustrating the ready for operation step of FIG. 25 in accordance with the principles of the present invention.

At step 96, surgical robot system 10 is ready for operation. As shown in FIG. 29, at step 96A, the control system verifies that instrument 82 is coupled to slave hub 69 of the slave telemanipulator. At step 96B, the control system detects when the surgeon grabs handle grip 40 of handle portion 35. As shown in FIGS. 9A and 9B, sensors within the handle may detect that the surgeon has grabbed the handle. At step 96C, clutch 11 is actuated to prepare the control system for macro-synchronization as described in step 97A.

Figure 30:
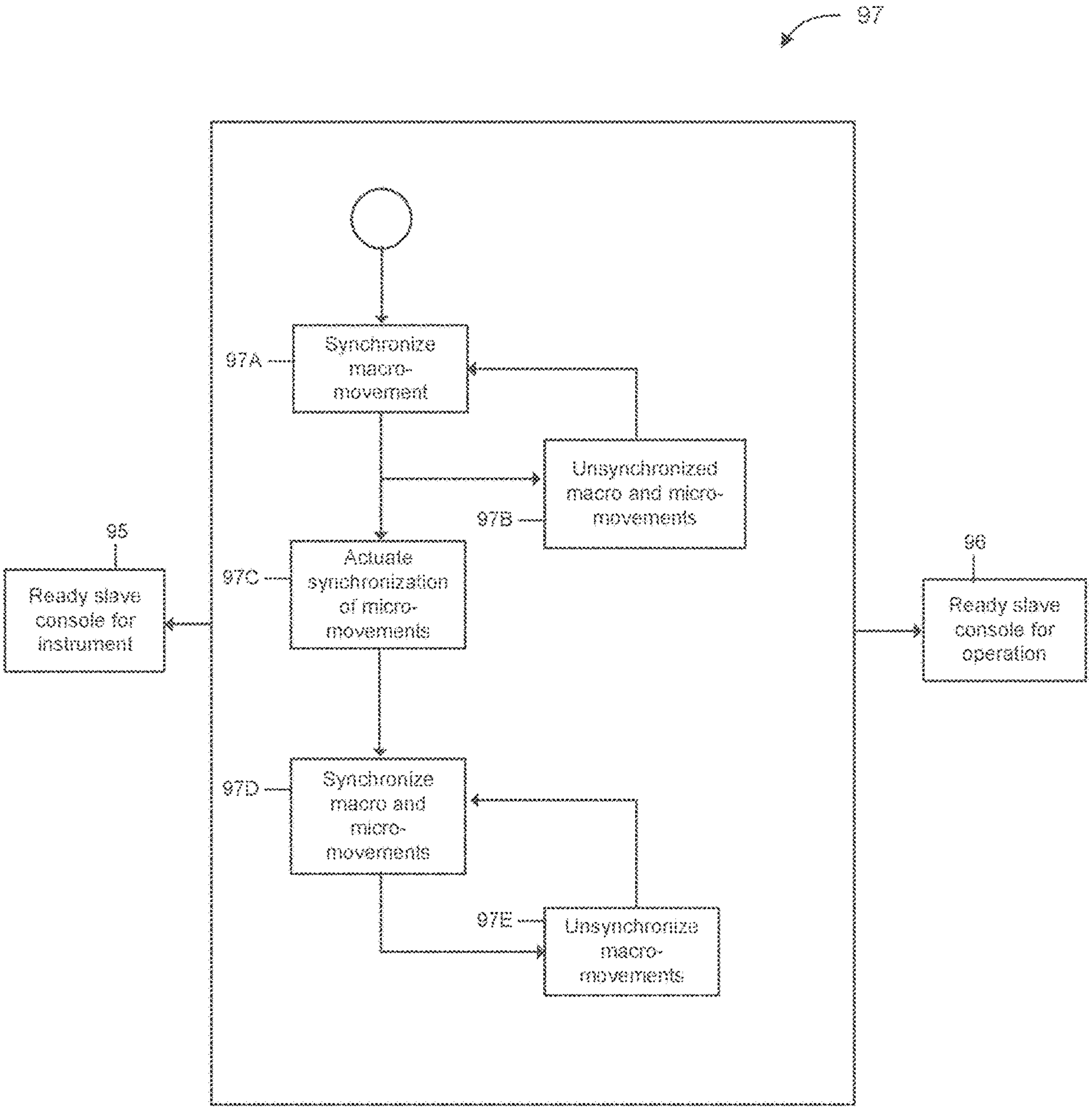
FIG. 30 is a flow chart illustrating the operating step of FIG. 25 in accordance with the principles of the present invention.

As shown in FIG. 30, surgical robot system 10 may now be operated. For example, at step 97A, surgical robot system 10 is in a macro-synchronization state, but not in a micro-synchronization state. In the macro-synchronization state, translational macro-movements applied at master console 20 will be sensed and transmitted to the control system, which instructs the actuators coupled to slave console 50 to cause the corresponding slave links and joints to move in a manner so that the macro-movements (i.e. up/down, left/right, in/out) of instrument tip 84 corresponds to the macro-movements of the handle at the master console 20. However, in the unsynchronized macro state, the control system does not cause macro-movements applied at master console 20 to be made in a corresponding manner at slave console 50. In the micro-synchronization state, micro-movements applied at handle portion 35 of master console 20 will be sensed and transmitted to the control system, which instructs the actuators coupled to slave console 50 to cause the instrument tip 84 move in a manner corresponding to those micro-movements applied at handle portion 35 of master console 20. However, in the unsynchronized micro state, the control system does not cause micro-movements applied at master console 20/handle portion 35 to be made in a corresponding manner at slave console 50/end-effector. Thus, at step 97A, translational macro-movements are replicated, but micro-movements are unsynchronized. Clutch 11 may be actuated to transition surgical robot system 10 to unsynchronized macro state at step 97B where translation macro-movements may be prevented by master console 20, and thus not replicated by slave console 50. For example, clutch 11 may be a foot pedal that when stepped on, maintains surgical robot system 10 in the unsynchronized macro state. Upon release of clutch 11, surgical robot system 10 returns to the macro-synchronization state at step 97A.

In addition, the control system may be programmed to detect an actuation pattern by handle portion 35 such that micro-movements at handle portion 35 are not replicated by the end-effector unless the control system detects the actuation pattern. For example, the actuation pattern may include a quick, double actuation of handle grip 40. Thus, when the user presses handle grip 40 twice repeatedly at step 97C, the control system detects the actuation pattern, and surgical robot system 10 is in a micro-synchronization state where micro-movements at handle portion 35 will be replicated by the end-effector. When transitioning from an unsynchronized micro state to a micro-synchronization state, the control system executes instructions to cause the micro-position of instrument tip 84 to have the same spatial orientation relative to the instrument shaft 82 as the spatial orientation of handle portion 35 relative to corresponding link 32 of master telemanipulator 22*a*. At step 97D, surgical robot system 10 is fully in both a macro-synchronization state and a micro-synchronization state, e.g., when the end-effector is in the target position for the operation, and the surgeon can use surgical robot system 10 to perform surgical tasks. Upon actuating clutch 11, at step 97E, surgical robot system 10 is in a micro-synchronization state, but in the unsynchronized macro state.

In accordance with another aspect of the present invention, a remotely actuated surgical robot system having hybrid telemanipulators, which may be used in minimally invasive surgical procedures or in other applications, constructed in accordance with the principles of the present invention, is described herein.

Figure 31A:
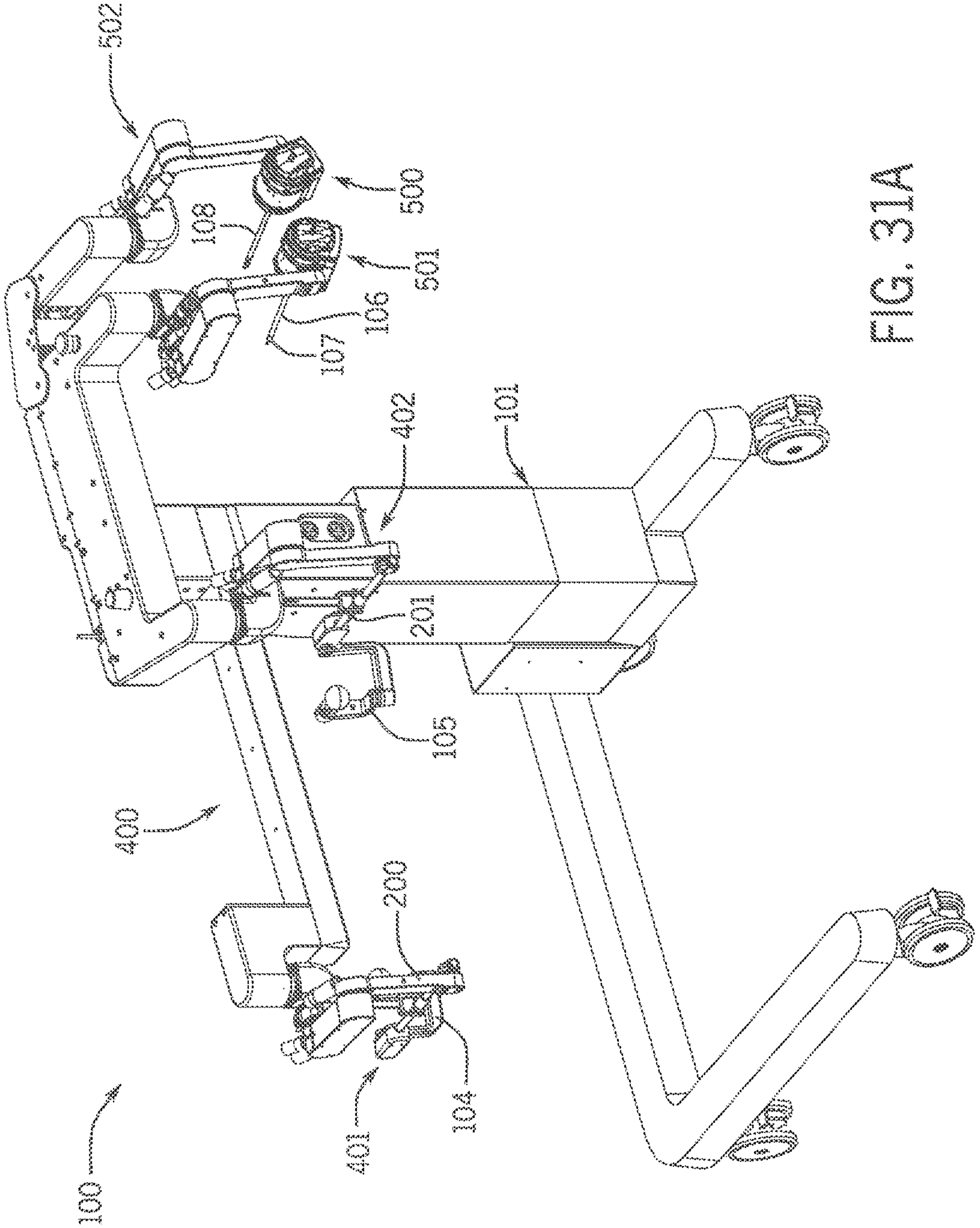
FIGS. 31A and 31B show an exemplary remotely actuated surgical robot system having hybrid telemanipulators constructed in accordance with the principles of the present invention.
Figure 31B:
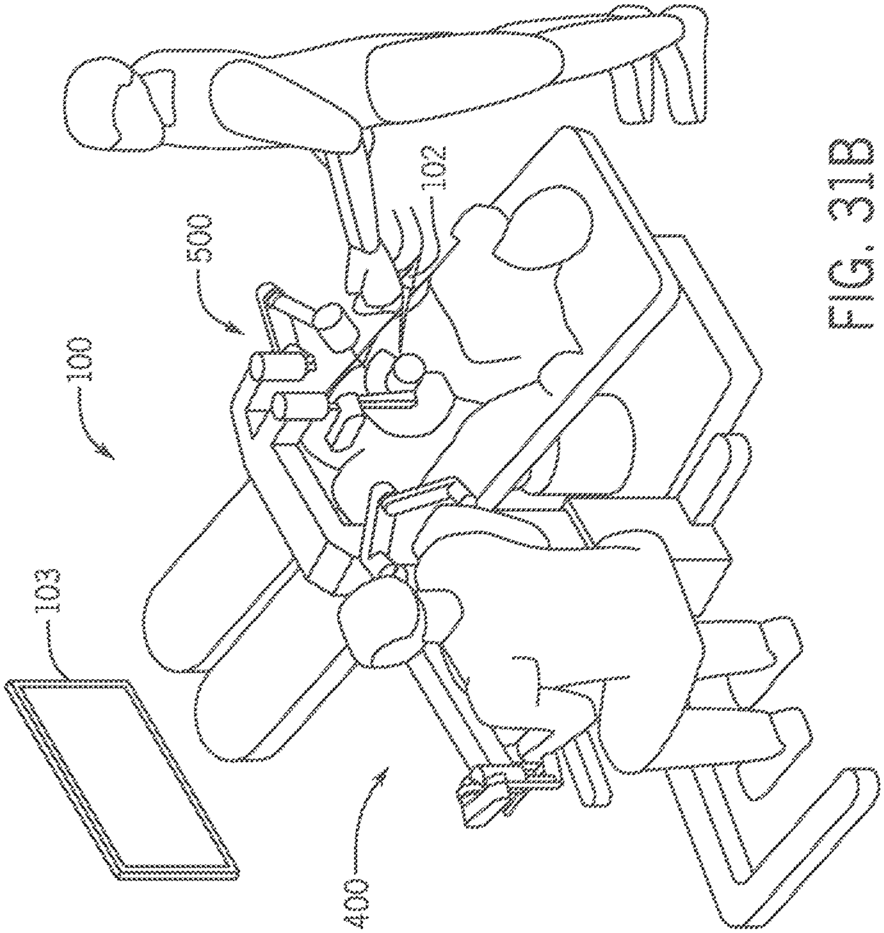

Referring to FIGS. 31A and 31B, exemplary remotely actuated surgical robot system 100 having hybrid telemanipulators is described. Surgical robot system 100 illustratively is affixed atop moveable cart 101, to which the hybrid telemanipulators also may be mounted for mobility and ease of transport within an operating room. Surgical robot system 100 includes master region 400, where a surgeon may be situated to operate system 100, and remote slave region 500 in proximity to the sterile zone, where a patient to be operated upon may be positioned. As shown in FIG. 31B, the operating surgeon preferably is seated with ready access to master region 400, while another surgeon or assistant may be situated near slave region 500, which is positioned over a patient. In the embodiment of FIGS. 31A and 31B, master region 400 is situated laterally adjacent to slave region 500. In addition, camera system 102 may be used with surgical robot system 100, e.g., an endoscope that is manipulated by the assistant situated at slave region 500 may be operate and/or held in position as shown in FIG. 31B. Camera system 102 also may include display 103 for displaying the surgical site captured by camera 102 to the surgeon in real-time. Display 103 may be mounted to master region 400, or anywhere in proximity to master region 400 that is easily observable by the surgeon during a surgical procedure.

Referring again to FIG. 31A, system 100 includes two hybrid telemanipulators 104 and 105, including left hybrid telemanipulator 104 that is manipulated by the surgeon's left hand, and right hybrid telemanipulator 105 that is manipulated by the surgeon's right hand. Hybrid telemanipulators 104 and 105 may be operated simultaneously and independently from the other, e.g., by the surgeon's left and right hands. Preferably, the teleoperated remotely actuated surgical robot system 100 is optimized for use in surgical procedures.

Each hybrid telemanipulator provides input to a master-slave configuration, in which a slave unit, made of a plurality of rigid slave links and slave joints, is driven kinematically by a master unit, made of a plurality of rigid master links and master joints. For example, left hybrid telemanipulator 104 includes master unit 401 and corresponding slave unit 501, and right hybrid telemanipulator 105 includes master unit 402 and corresponding slave unit 502. Master units 401 and 402 are disposed within master region 400 of system 100, while slave units 501 and 502 are within slave region 500 of system 100. Preferably, slave units 501 and 502 mimics the movement of the corresponding portions of master units 401 and 402, respectively, without deviating, during operation of the device, from a remote center-of-motion, as described in further detail below.

Still referring to FIG. 31A, teleoperated surgical instrument 106, e.g., translational instrument interface, having end effector 107 is coupled to the distal end of slave unit 501, and a handle is coupled to the distal end of master unit 401 such that movement applied to the handle induces a corresponding micro-movement of end-effector 107 via a processor-driven control system. For example, the control system may receive a signal indicative of movement applied at the handle by one or more sensors coupled to the handle, and perform coordinate transforms necessary to activate one or more actuators operatively coupled to end-effector 107 to replicate a corresponding movement of the end effector. Slave instrument 106 of the translational instrument interface may be removeably attached to and operated by slave unit 501, such that the translation degrees-of-freedom, e.g., left/right, upward/downward, inward/outward, are actuated by direct mechanical coupling, whereas the articulation degrees-of-freedom, e.g., pitch and yaw, the actuation degrees-of-freedom, e.g., open/close, and the rotation degree-of-freedom, e.g., pronosupination, are electromechanically replicated via sensors, actuators, and a control system as described in further detail below.

Figure 32A:
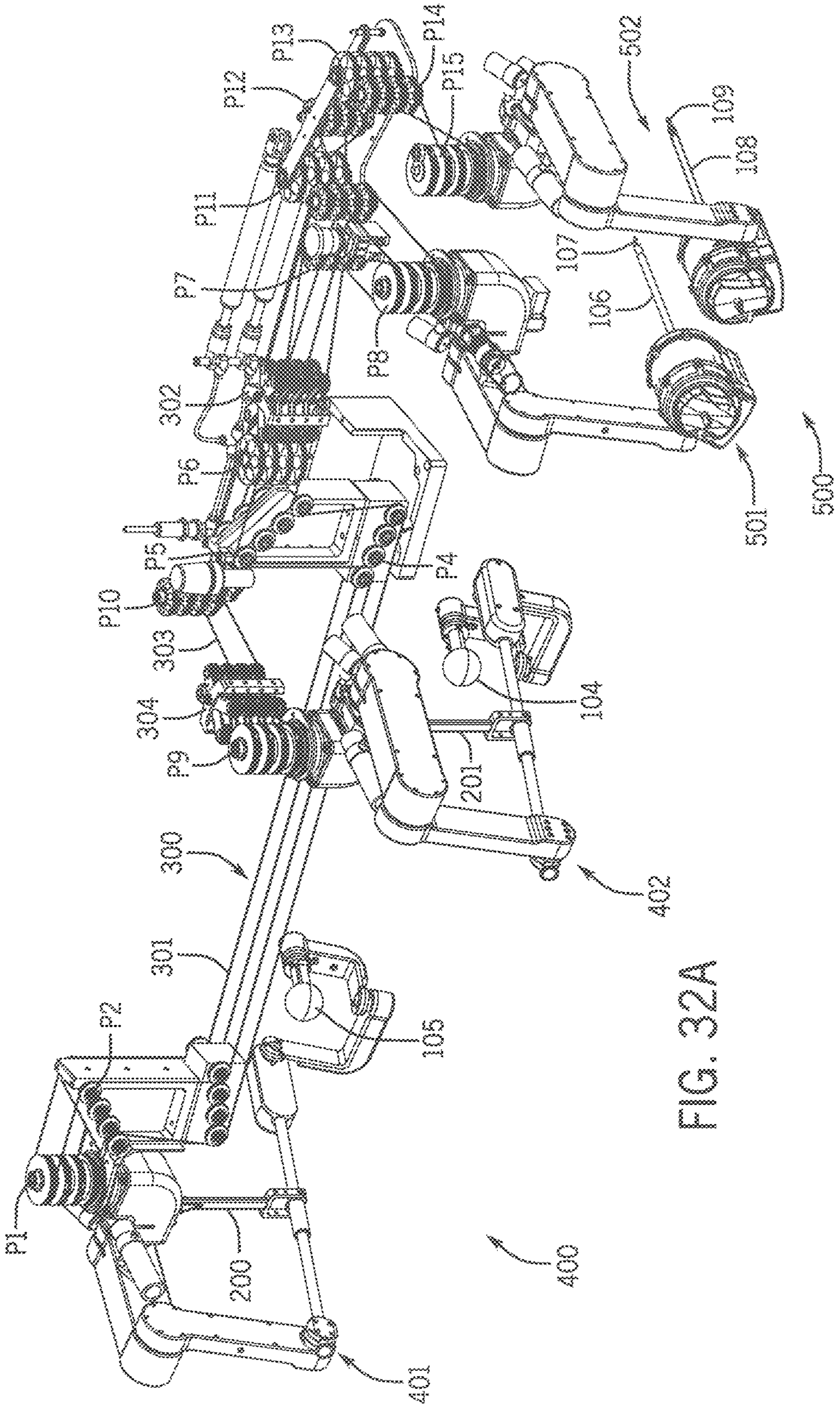
FIGS. 32A and 32B show partially exploded perspective views of the surgical robot system of FIGS. 31A and 31B.
Figure 32B:
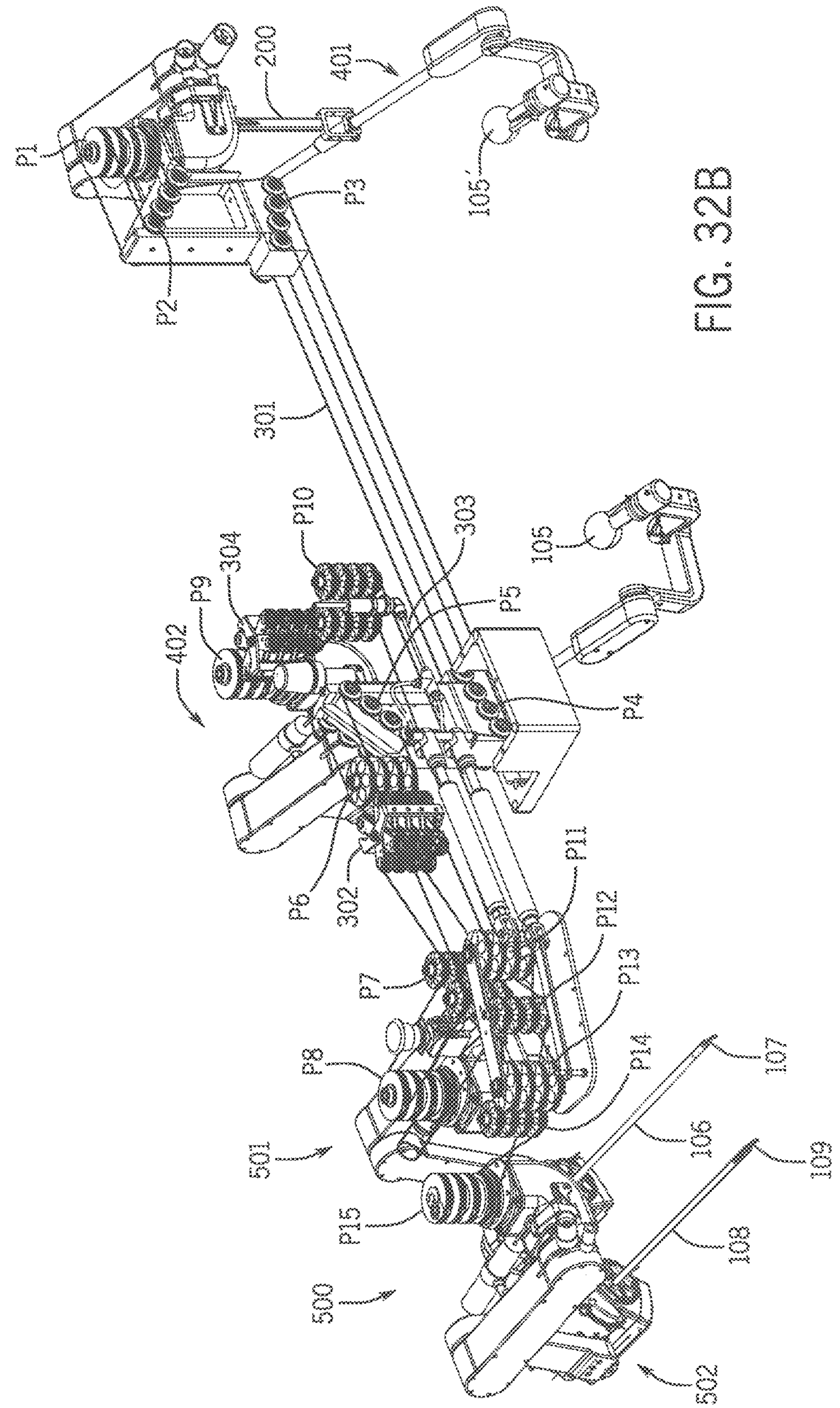

Referring now to FIGS. 32A and 32B, the mechanisms of exemplary remotely actuated surgical robot system 100 having hybrid telemanipulators are illustrated, in which the external covers depicted in FIG. 31 are omitted for clarity. In FIGS. 32A and 32B, mechanical transmission 300 is arranged to directly couple slave unit 501 with master unit 401, such that translational macro-movement applied to the plurality of master joints of master unit 401 is replicated by corresponding respective joints of the plurality of slave joints of slave unit 501. Likewise, mechanical transmission 300 also directly couples slave unit 502 with master unit 402, such that translational macro-movement applied to the plurality of master joints of master unit 402 is replicated by corresponding respective joints of the plurality of slave joints of slave unit 502. Transmission 300 illustratively includes one or more cables 301 routed via one or more pulleys from master unit 401 to slave unit 501, and one or more cables 303 routed via one or more pulleys from master unit 402 to slave unit 502, for controlling one of four degrees-of-freedom of slave unit 501 and 502. Mechanical constraint 200 of master unit 401 constrains movement of master unit 401 by removing a degree-of-freedom of motion, thereby limiting movement in three translational degrees-of-freedom, e.g., left/right, upward/downward, inward/outward.

For example, one or more cables 301 may form one or more closed loops beginning at pulley P1 coupled to master unit 401, and extending through pulleys P2, P3, P4, P5, P6, tensioning system 302, pulley P7, and around pulley P8 coupled to slave unit 501, and extending back through pulley P7, tensioning system 302, pulleys P6, P5, P4, P3, P2, and ending at pulley P1. Thus, rotation of pulley P1 clockwise or counter-clockwise causes a cable of one or more cables 301 to rotate pulley P8, thereby actuating a slave unit 501 in one of four degrees-of-freedoms. Mechanical constraint 200 of master unit 401, however, constrains movement of master unit 401 by removing one degree-of-freedom of motion, thereby limiting movement of slave unit 501 to three translational degrees-of-freedom, e.g., left/right, upward/downward, inward/outward. Each of pulleys P1, P2, P3, P4, P5, P6, P7, and P8 may include a number of individual pulleys corresponding to the number of degrees-of-freedom of motion actuable of slave unit 501 by master unit 401. Similarly, one or more cables 301 may include a number of closed cable loops corresponding to the number of degrees-of-freedom of motion actuable of slave unit 501 by master unit 401.

Similarly, one or more cables 303 may form one or more corresponding closed loops beginning at pulley P9, coupled to master unit 402, and extending through tensioning system 304, pulleys P10, P11, P12, P13, P14, and around pulley P15 coupled to slave unit 502, and extending back through pulleys P14, P13, P12, P11, P10, tensioning system 304, and ending at pulley P9. In this manner, rotation of pulley P9 clockwise or counter-clockwise may cause a cable of one or more cables 303 to rotate pulley P15, thereby actuating a slave unit 502 in one of four degrees-of-freedoms. Mechanical constraint 201 of master unit 402 (see FIG. 32A) likewise constrains movement of master unit 402 by removing a degree-of-freedom of motion, thereby limiting movement of slave unit 502 to three translational degrees-of-freedom, e.g., left/right, upward/downward, inward/outward. Each of pulleys P9, P10, P11, P12, P13, P14, and P15 may include a number of individual pulleys corresponding to the number of degrees-of-freedom of motion actuable of slave unit 502 by master unit 402. Similarly, one or more cables 303 may include a number of closed cable loops corresponding to the number of degrees-of-freedom of motion actuable of slave unit 502 by master unit 402.

As will be understood by a person having ordinary skill in the art, the number of pulleys P2-P7 employed to route cables 301 between pulleys P1 and P8, and the number of pulleys P10-P14 employed to route cables 303 between pulleys P9 and P15 will depend on the construction of the right and left hybrid telemanipulators, respectively.

Figure 33:
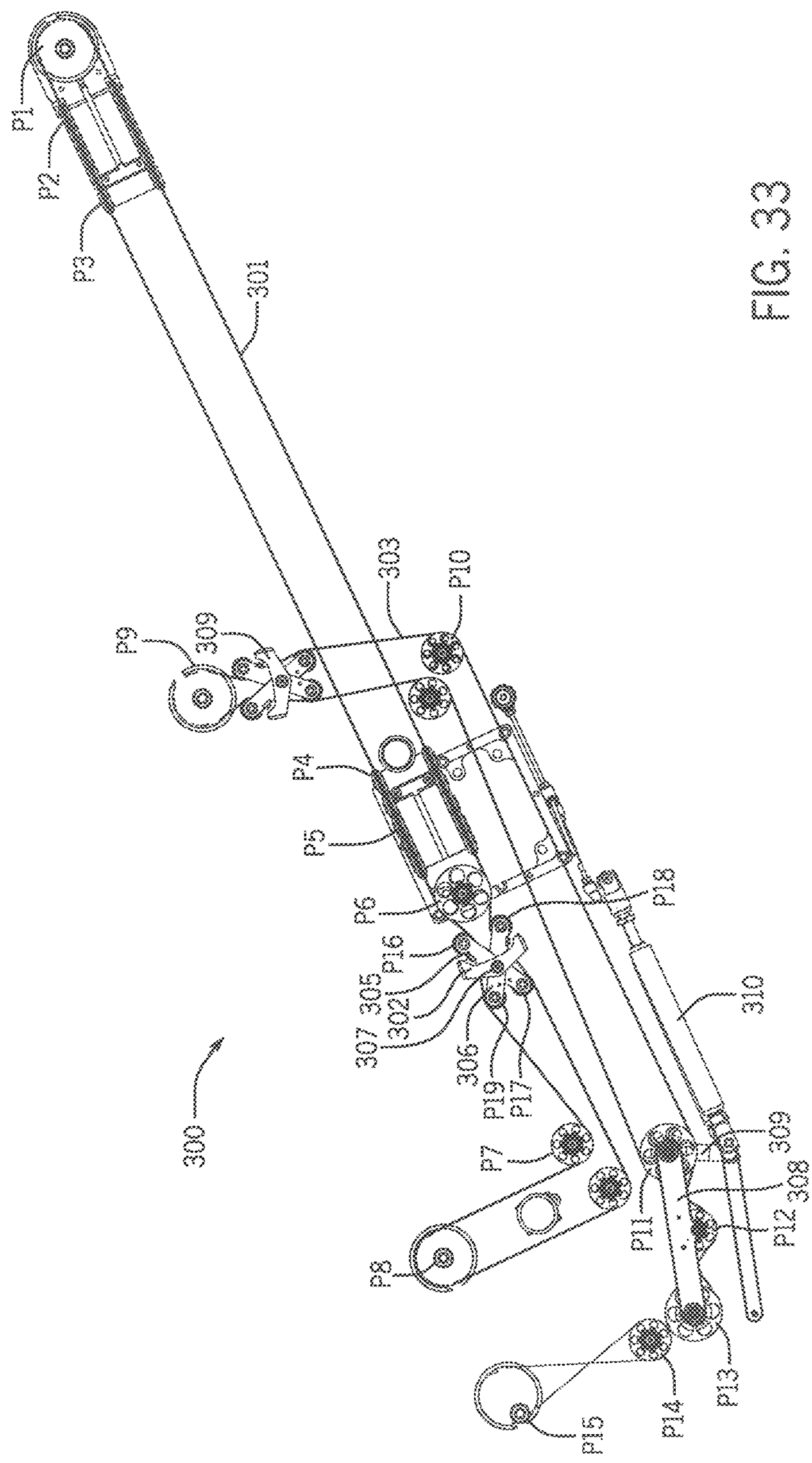
FIG. 33 shows a top view, partially exploded, of an exemplary mechanical transmission system constructed in accordance with the principles of the present invention.

Referring now to FIG. 33, one or more cables 301 of mechanical transmission 300 pass through tensioning system 302, and one or more cables 303 passes through tensioning system 304. Tensioning system 302 is designed to apply a predetermined tension force to cables 301, while tensioning system 304 is designed to apply a predetermined tension force to cables 303. For example, tensioning system 302 may include pulley P16 coupled to pulley P17 via tension link 305, and pulley P18 coupled to pulley P19 via tension link 306. Tension link 305 is adjustably and rotatably coupled to tension link 306 about a vertical axis running through axle 307, such that a predetermined tension force is applied to cables 301 by pulleys P16, P17, P18, and P19. In addition, tensioning system 302 may be used to calibrate mechanical transmission 300, thereby ensuring that the angles of corresponding master and slave joints are identical. Tensioning system 304 may be identical in structure to tensioning system 302.

Also in FIG. 33, pulleys P11, P12, and P13 of the mechanical transmission of the right hybrid telemanipulator are coupled to slave link 308, which is rotatably coupled to positioning system 310 via slave link 309. Positioning system 310 may be, e.g., a hydraulic device, that restricts movement of slave unit 502 with respect to slave unit 501 along a single plane. For example, the position of pulley P8 may be fixed, such that the position of P15 is moveable relative to P8 along the horizontal plane (x- and y-direction).

Figure 34A:
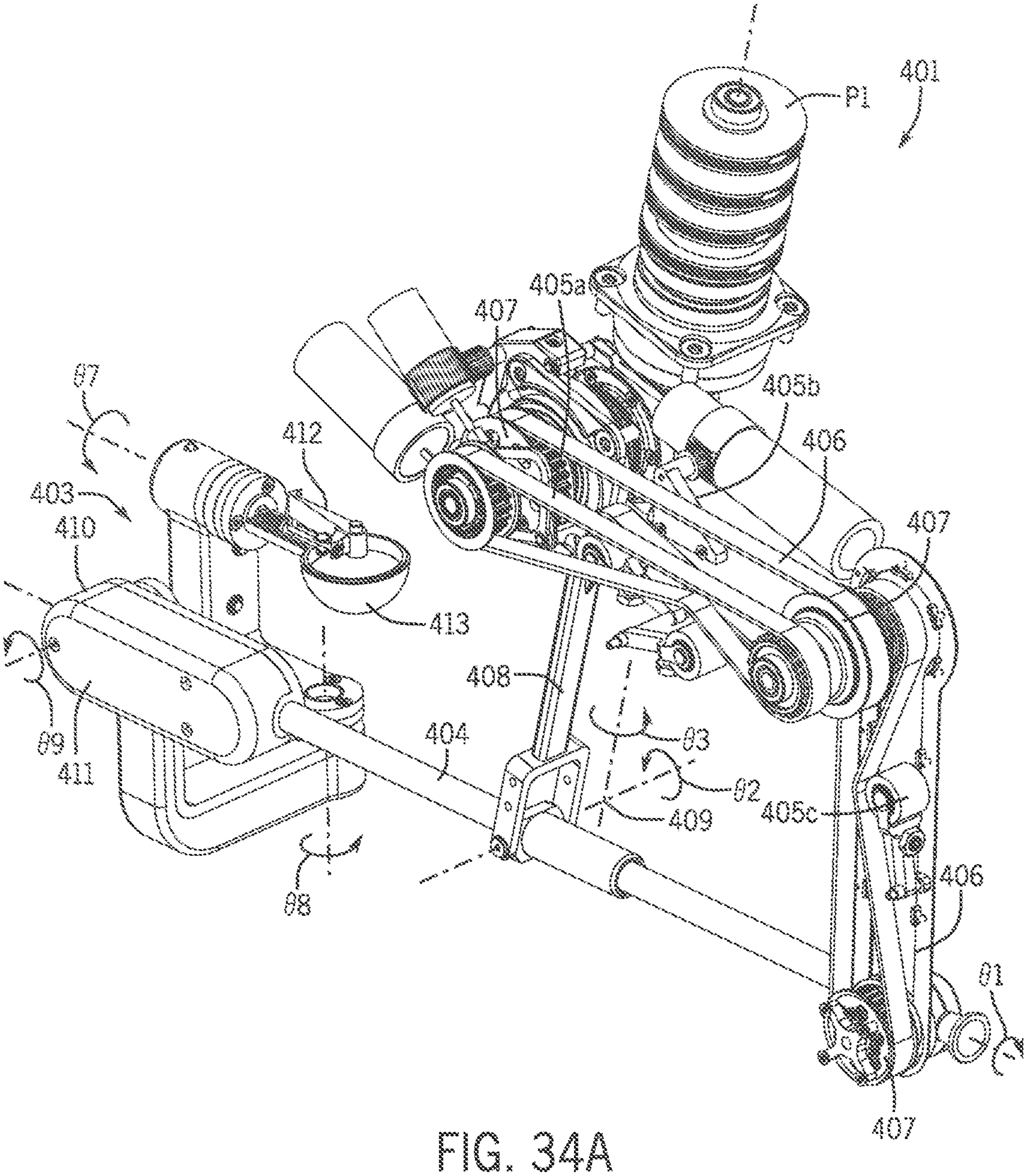
FIGS. 34A and 34B show side perspective views of an exemplary master unit constructed in accordance with the principles of the present invention.
Figure 34B:
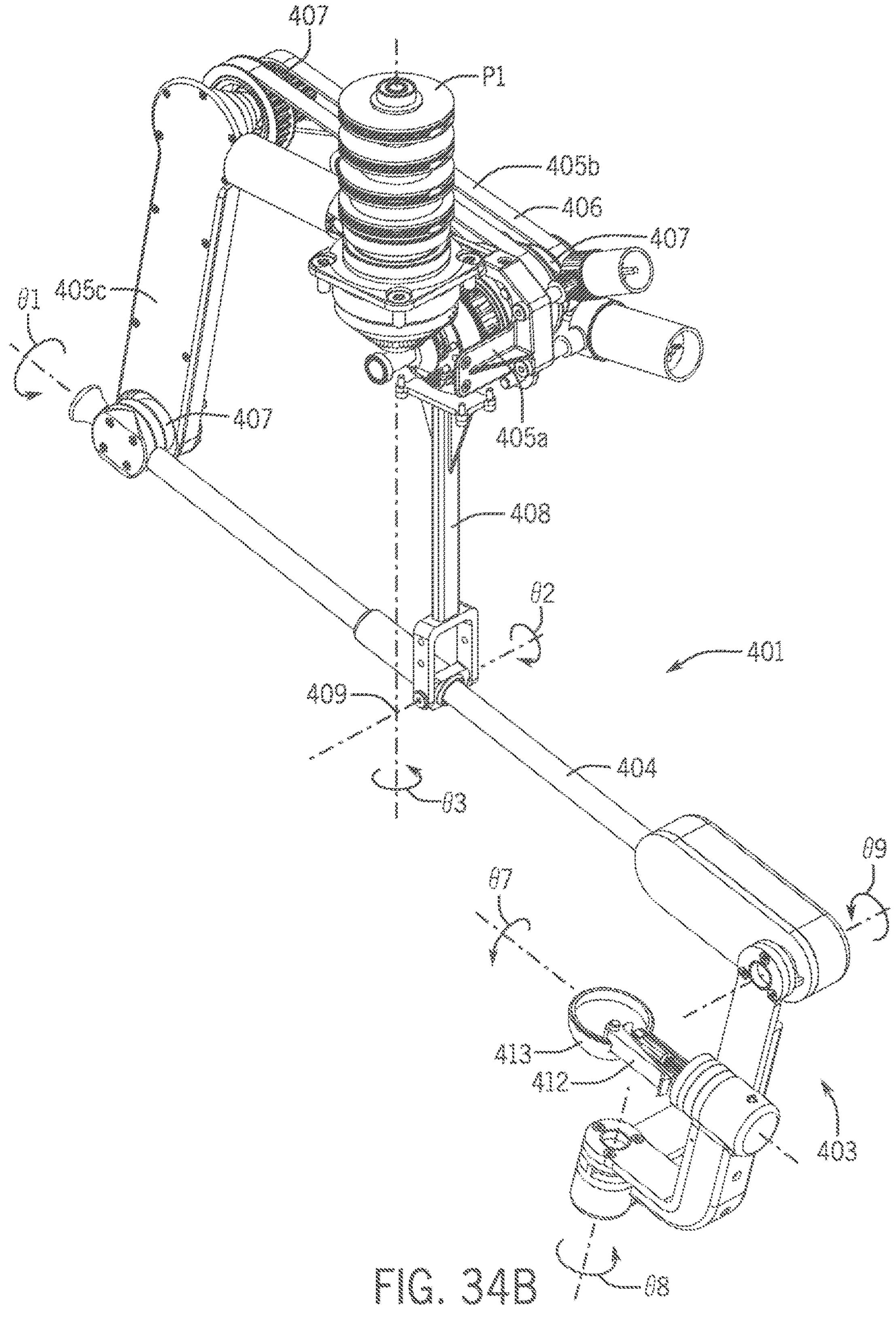

Referring now to FIGS. 34A and 34B, components of an exemplary master unit of system 100 is described. As master unit 401 is identical in structure to master unit 402, respectively, the description below of master unit 401 applies also to master unit 402.

Master unit 401 includes a plurality of master links, e.g., first master link 405*a*, second master link 405*b*, third master link 405*c*, and fourth master link, e.g., guided master link 404, interconnected by a plurality of master joints. Handle 403 is connected to a distal end of master unit 401 via guided master link 404, e.g., master rod, and includes a plurality of handle links interconnected by a plurality of handle joints for operating the hybrid telemanipulator. For example, translational macro-movement applied on handle 403 causes corresponding movement of the plurality of master joints via the plurality of master links, which is transmitted to the corresponding slave joints of slave unit 501 via mechanical transmission 300, thereby replicating the translational macro-movement at slave unit 501. Translational movement of handle 403 causes guided master link 404 to transmit motion to pulley P1 via first master link 405*a*, second master link 405*b*, and third master link 405*c*, thereby causing slave unit 501 to mimic the translational movement via mechanical transmission 300. First master link 405*a*, second master link 405*b*, third master link 405*c*, and guided master link 404 are coupled to pulley P1 via a transmission system including, e.g., one or more toothed belts 406 routed via one or more pulleys 407. Alternatively, the transmission system coupling pulley P1 and the plurality of master links and joints of master unit 501 may include a system of cables and pulleys, and/or rigid transmission links.

Figure 35A:
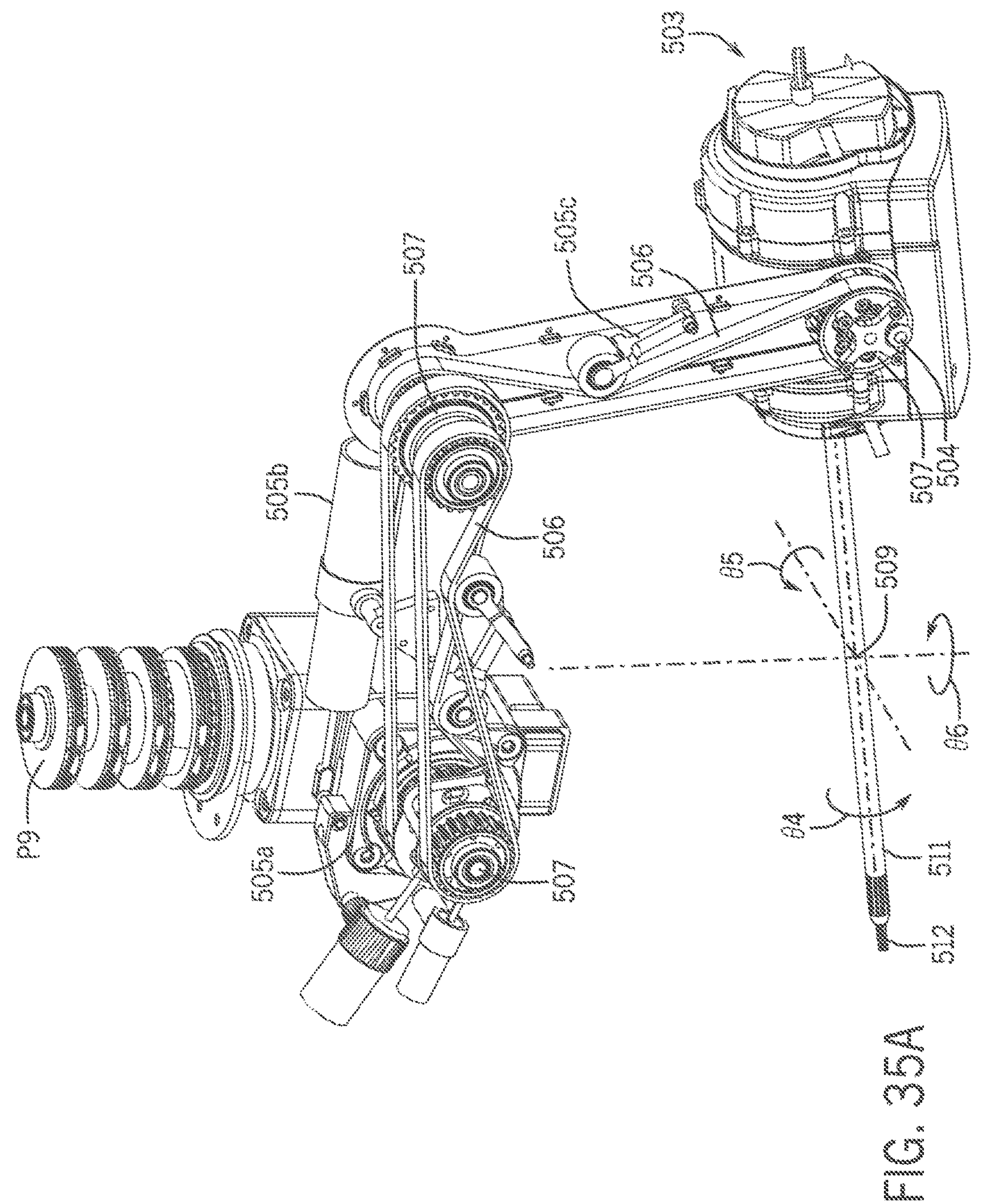
FIGS. 35A and 35B show side perspective views of an exemplary slave unit constructed in accordance with the principles of the present invention.
Figure 35B:
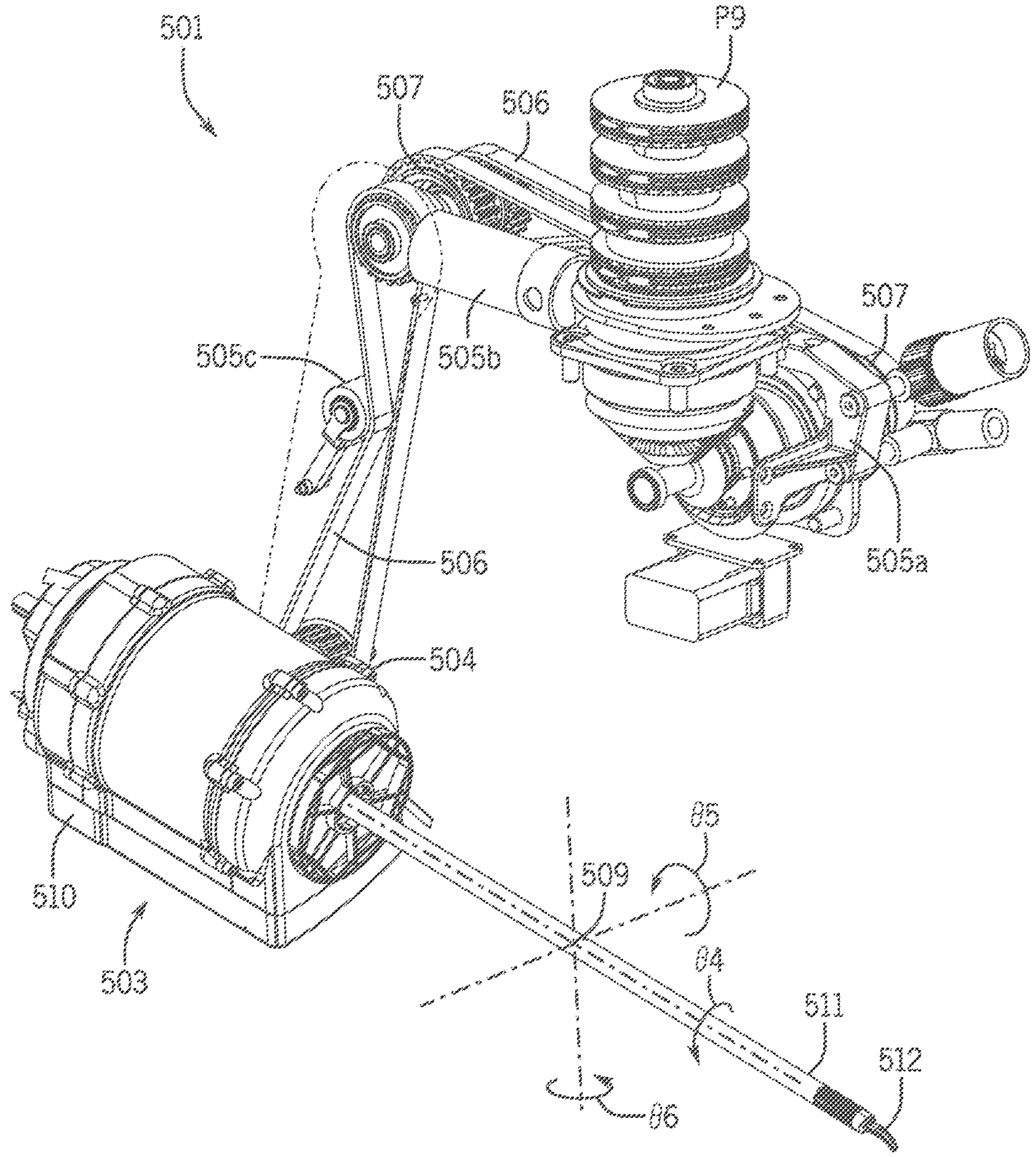

In FIGS. 34A and 34B, mechanical constraint 408 on master unit 401 includes a yoke pivotally coupled to a sleeve that slides on guided master link 404 and constrains movements of the distal end of slave unit 501 in correspondence with a remote center of motion that is aligned with the incision point on a patient, e.g., the point at which a trocar passes into a patient's abdomen. For example, mechanical constraint 408 ensures that, when the hybrid telemanipulator is actuated, guided master link 404 of master unit 401 translates along longitudinal axis $\theta_1$ so that the corresponding slave link of slave unit 501, e.g., translational instrument interface coupled to the distal end of slave unit 501, also translates along virtual axis $\theta_4$ parallel to longitudinal axis $\theta_1$ of guided master link 404 in the vicinity of the remote manipulation, as depicted in FIGS. 35A and 35B. In addition, mechanical constraint 408 enables guided master link 404 to rotate about second and third axes $\theta_2$, $\theta_3$ that are perpendicular to each other. Referring still to FIGS. 34A and 34B, axis $\theta_3$ is coaxial to the axis of pulley P1. The plane defined by longitudinal axis $\theta_1$ of guided master link 404 and second axis $\theta_2$ intersects third axis $\theta_3$ at stationary single point 409 independently of the orientation of master link 404. This configuration allows the corresponding slave link of slave unit 501 to rotate about fifth and sixth virtual axes $\theta_5$, $\theta_6$ that are perpendicular to each other. Longitudinal axis $\theta_4$ of the corresponding slave link and fifth and sixth virtual axes $\theta_5$, $\theta_6$ always intersect each other at virtual stationary single point 509, e.g., the remote center-of-motion, in the vicinity of the patient incision.

When surgical robot system 100 is positioned such that remote center-of-motion 509 is aligned with the patient incision, translational movement applied to handle 403 is replicated by the end-effector disposed inside the patient.

Because the end-effector perfectly replicates the movement applied to handle 403, this arrangement advantageously eliminates the fulcrum effect between the handle and end-effector, and ensures that the instrument always passes through the remote center-of-motion. Whereas in previously-known surgical robots, maintaining a fixed point of movement of the surgical instrument as it passes through the patient incision requires complex control electronics, in the system of the present invention, mechanical constraint 408 provides translational replication between master unit 401 and slave unit 501 that ensures that the instrument always passes through remote center-of-motion 509.

Inward/outward movement of handle 403 of the embodiments of FIGS. 34A and 34B causes first master link 405*a*, second master link 405*b*, third master link 405*c*, and guided master link 404 to move inward/outward along longitudinal axis $\theta_1$ of guided master link 404. That motion is transmitted to pulley P1 via the plurality of master links, causing slave unit 501 to replicate the inward/outward movement about longitudinal axis $\theta_4$ via mechanical transmission 300 and the plurality of slave links, joints, and timing belts. Similarly, movement of handle 403 upward/downward causes first master link 405*a*, second master link 405*b*, third master link 405*c*, and guided master link 404 to rotate upward/downward about second axis $\theta_2$. That motion is transmitted to pulley P1 via the plurality of master links, in turn causing slave unit 501 to replicate the upward/downward movement about fifth axis $\theta_5$ via mechanical transmission 300 and the plurality of slave links, joints, and timing belts. Finally, movement of handle 403 left/right causes first master link 405*a*, second master link 405*b*, third master link 405*c*, and guided master link 404 to rotate left/right about third axis $\theta_3$. That motion is transmitted to pulley P1 via the plurality of master links, causing slave unit 501 to replicate the left/right movement about sixth axis $\theta_6$ via mechanical transmission 300 and the plurality of slave links, joints, and timing belts.

Still referring to FIGS. 34A and 34B, movement applied at handle 403 of master unit 401 actuates the articulation degrees-of-freedom, e.g., pitch and yaw, the actuation degree-of-freedom, e.g., open/close, and the rotation degree-of-freedom, e.g., pronosupination, electromechanically via sensors, motors, and a control system. Master unit 401 preferably includes one or more sensors 410 coupled to handle 403 via circuit board 411 for detecting motion of handle 403. As will be understood, sensor 410 may be any sensor designed to detect rotational movement, such as magnetic-based rotational sensors that includes a magnet on one side and a sensor on another side to measure rotation by measuring angle and position. Circuit board 411 is coupled to a control system for generating signals indicative of the rotation measured by sensor 410 and transmitting the signals to one or more motors coupled to slave unit 501, which may reproduce movements applied on handle 403 to the end effector. For example, electrical cables may extend from handle 403 to the control system, e.g., a unit containing control electronics, and additional electrical cables may extend from the control system to the one or more motors coupled to slave unit 501.

Actuation of trigger 412 of handle 403 generates a signal that is transmitted via the control system to the motors coupled to slave unit 501, thereby causing actuation of a translation transmission system of the translational instrument interface coupled to slave unit 501, in turn causing actuation of the end-effector of the translational instrument interface to open/close.

Handle 403 also may include ball 413 designed to be easily gripped by the surgeon and which aligns the surgeon's wrist with master unit 401. Ball 413 may be rotatable about handle axis $\theta_7$, such that the rotation of ball 413 is detected by a sensor that generates and transmits a signal via the control system to a motor coupled to slave unit 501. The signal received from the control system at the slave unit causes rotation of the translational instrument interface coupled to slave unit 501, thus rotating the end-effector of the translational instrument interface in the pronosupination degree-of-freedom.

Handle 403 also is rotatable about handle axis $\theta_8$, such that the rotation about handle axis $\theta_8$ is detected by a sensor, which generates and transmits a signal via the control system to the motors of slave unit 501. That signal causes actuation of the translation transmission system of the translational instrument interface coupled to slave unit 501, which in turn causes movement of the end-effector of the translational instrument interface in the yaw degree-of-freedom. In addition, handle 403 may be rotatable about handle axis $\theta_9$, such that the rotation of handle 403 about handle axis $\theta_9$ is detected by a sensor, which generates and transmits a signal via the control system to the motors of slave unit 501. That signal causes actuation of the translation transmission system of the translational instrument interface coupled to slave unit 501, which causes movement of the end-effector of the translational instrument interface in the pitch degree-of-freedom.

Figure 34C:
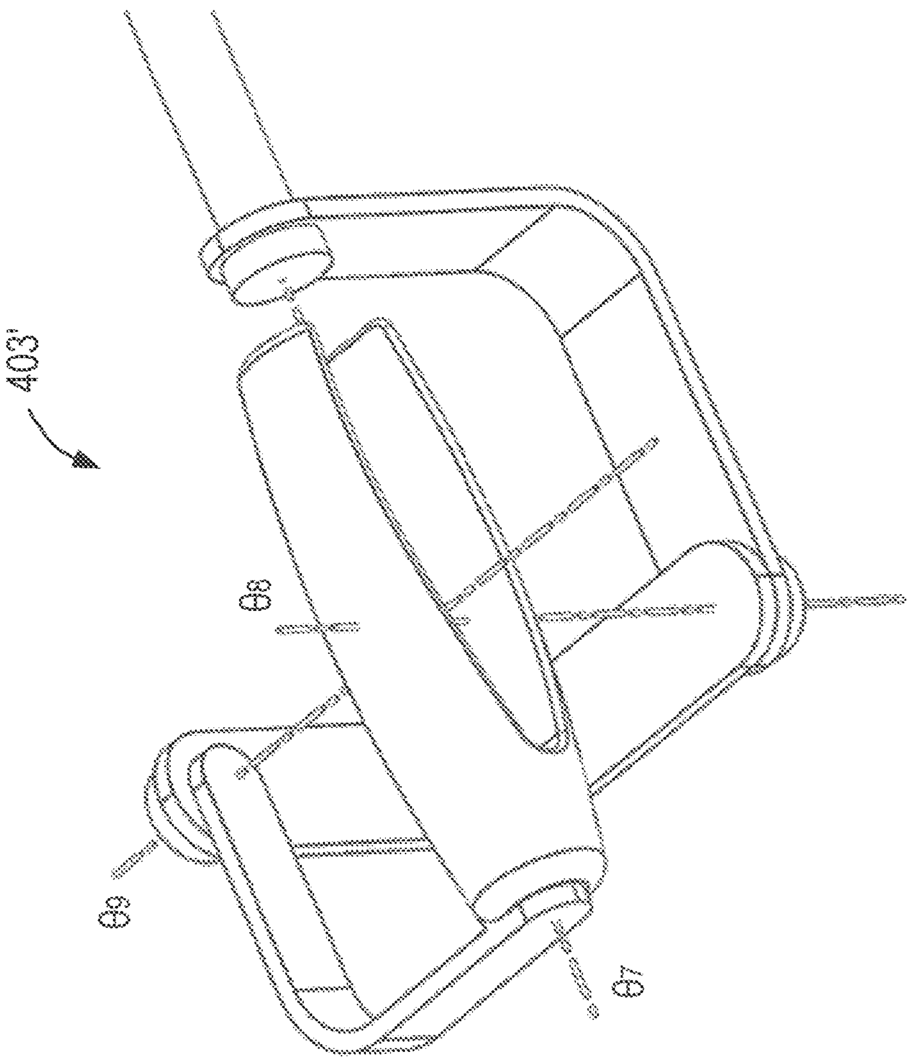
FIGS. 34C and 34D show alternative embodiments of a handle suitable for use with the master unit depicted in FIGS. 34A and 34B.
Figure 34D:
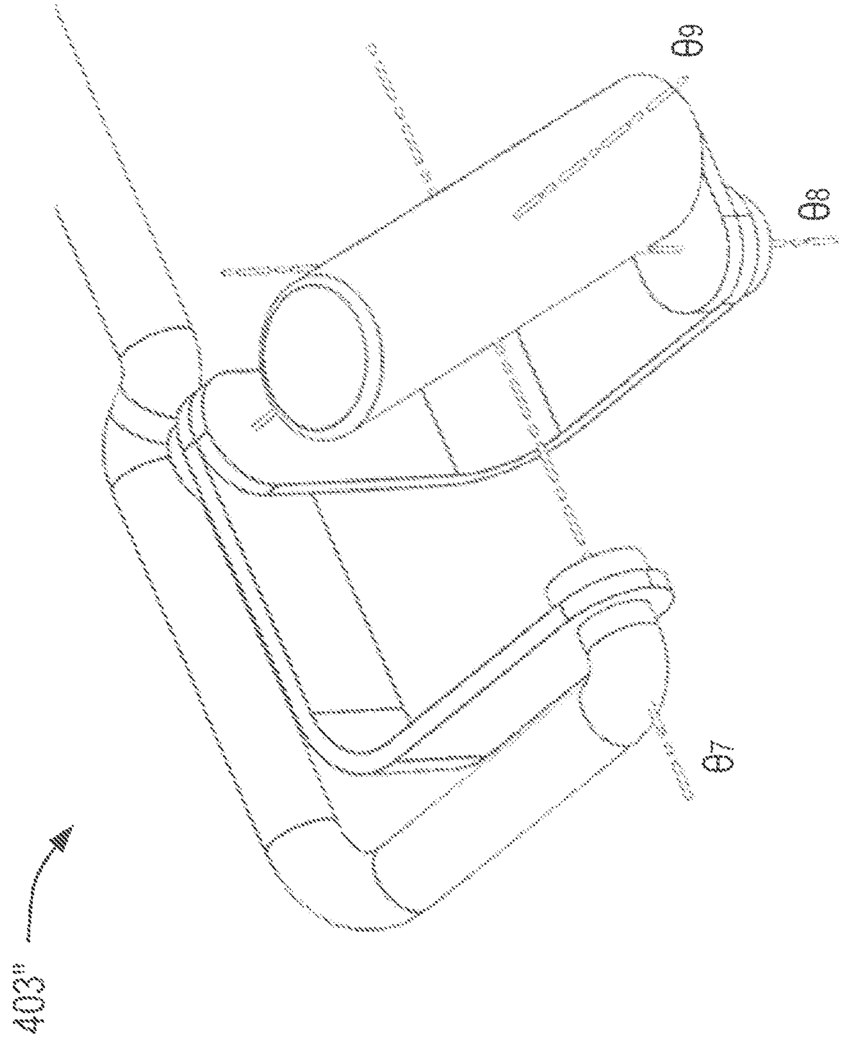

Referring now to FIGS. 34C and 34D, alternative embodiments of the handle of master unit 401 are described. In FIG. 34C, handle 403' is rotatable about handle axis $\theta_7$, handle axis $\theta_8$, and handle axis $\theta_9$, such that rotation of handle 403' about the handle axes is detected by one or more sensors 410, which generate and transmit a signal via the control system to motors of slave unit 501. That signal actuates the translation transmission system of the translational instrument interface coupled to slave unit 501, causing movement of the end-effector of the translational instrument interface in the pronosupination, yaw, and pitch degrees-of-freedom, respectively.

Similarly, handle 403" of FIG. 34D is rotatable about handle axis $\theta_7$, handle axis $\theta_8$, and handle axis $\theta_9$, such that rotation of handle 403" about the handle axes is detected by one or more sensors 410, which generates and transmits a signal via the control system to the one or more motors coupled to slave unit 501. That signal actuates the translation transmission system of the translational instrument interface coupled to slave unit 501, causing movement of the end-effector of the translational instrument interface in the pronosupination, yaw, and pitch degrees-of-freedom, respectively.

Referring now to FIGS. 35A and 35B, an exemplary slave unit of system 100 is described. As slave unit 501 is identical in structure to slave unit 502, respectively, the description below of slave unit 501 applies also to slave unit 502.

As described above, master unit 401 includes a plurality of master links interconnected by a plurality of master joints. Slave unit 501 includes a corresponding plurality of slave links, e.g., first slave link 505*a*, second slave link 505*b*, third slave link 505*c*, and fourth slave link, e.g., translational instrument interface 503, interconnected by a plurality of slave joints, such that a direct mechanical coupling is formed by the plurality of slave links and corresponding plurality of slave joints of slave unit 501, which is identical to the kinematic model formed by the corresponding plurality of master links and corresponding plurality of master joints of master unit 401. For example, first slave link 505*a* always remains parallel to first master link 405*a*, second slave link 505*b* always remains parallel to second master link 405*b*, third slave link 505*c* always remains parallel to third master link 405*c*, and translational instrument interface 503 always remains parallel to guided master link 404 during operation of the hybrid telemanipulator. Thus, each translational macro-movement applied to the plurality of master joints of master unit 401 is replicated by a corresponding respective joint of the plurality of slave joints of slave unit 501 via mechanical transmission 300 and the plurality of slave links.

In FIGS. 35A and 35B, translational instrument interface 503 is coupled to distal end 504 of slave unit 501. Translational movement of handle 403 is transmitted to pulley P9 via mechanical transmission 300. More specifically, translational actuation of handle 403 causes pulley P9 to transmit motion to end-effector 512 via first slave link 505*a*, second slave link 505*b*, third slave link 505*c*, and translational instrument interface 503, thereby causing slave unit 501 to replicate the translational movement. First slave link 505*a*, second slave link 505*b*, third slave link 505*c*, and translational instrument interface 503 are coupled to pulley P9 via a transmission system including, e.g., one or more timing belts 506 routed via one or more pulleys 507. Thus, each of the four pulleys of P9 is operatively coupled to and controls movement of first slave link 505*a*, second slave link 505*b*, third slave link 505*c*, and translational instrument interface 503. Alternatively, the transmission system coupling pulley P9 and the plurality of slave links and joints of slave unit 501 may include a system of cables and pulleys, and/or rigid transmission links.

Mechanical constraint 408 of master unit 401 ensures that, when the hybrid telemanipulator is in operation, first slave link 505*a*, second slave link 505*b*, third slave link 505*c*, and translational instrument interface 503 always rotate about virtual stationary point 509. For example, end-effector 512 of translational instrument interface 503 coupled to slave unit 501 always translates along longitudinal axis $\theta_4$ corresponding to the longitudinal axis $\theta_1$ of master link 404 in the vicinity of the remote manipulation. In addition, mechanical constraint 408 allows end-effector 512 to rotate about fifth and a sixth virtual axis $\theta_5$, $\theta_6$ that are perpendicular to each other. Longitudinal axis $\theta_4$ of translational instrument interface 503 coupled to slave unit 501, and fifth and sixth virtual axes $\theta_5$, $\theta_6$ always intersect each other at virtual stationary single point 509 in the vicinity of the remote manipulation. During a minimally invasive surgical procedure, virtual stationary point 509 is aligned with the surgical incision point, reducing trauma to the patient and improving cosmetic outcomes of the surgery.

Movement of handle 403 in the inward/outward directions causes end effector 512 coupled to slave unit 501 to replicate the inward/outward movement about longitudinal axis $\theta_4$ via mechanical transmission 300 and the transmission system coupling pulley P9 and the plurality of slave links and joints of slave unit 501. Movement of handle 403 upward/downward causes end effector 512 coupled to slave unit 501 to replicate the upward/downward movement about longitudinal axis $\theta_5$ via mechanical transmission 300 and the transmission system coupling pulley P9 and the plurality of slave links and joints of slave unit 501. Movement of handle 403 left/right causes end effector 512 coupled to slave unit 501 to replicate the left/right movement about longitudinal axis $\theta_6$ via mechanical transmission 300 and the transmission system coupling pulley P9 and the plurality of slave links and joints of slave unit 501.

In addition, movement applied at handle 403 of master unit 401 actuates the articulation degrees-of-freedom, e.g., pitch and yaw, the actuation degree-of-freedom, e.g., open/close, and the rotation degree-of-freedom, e.g., pronosupination of the end-effector of translational instrument interface 503, electromechanically via sensors, motors, and a control system. Translational instrument interface 503 may be constructed as described in U.S. Patent Publication No. 2018/0353252 to Chassot, assigned to the assignee of the instant application, the entire contents of which are incorporated by reference herein. For example, translational instrument interface 503 includes slave hub 510 and surgical instrument 511. Slave hub 510 may be affixed to distal end 504 of slave unit 501. Surgical instrument 511 includes end-effector 512 disposed at the distal end of the shaft of surgical instrument 511, and may be removeably coupled to slave hub 510. A sterile interface may be positioned between slave hub 510 and surgical instrument 511. In addition, translational instrument interface 503 includes a translation transmission system that extends from one or more motors positioned within slave hub 510 to the components of end-effector 512. For example, end-effector 512 includes a plurality of end-effector links interconnected by a plurality of end-effector joints coupled to the translation transmission system of translational instrument interface 503, such that actuation of the translation transmission system by the one or more motors causes movement of end-effector 512 via the plurality of end-effector links and joints.

Figure 36A:
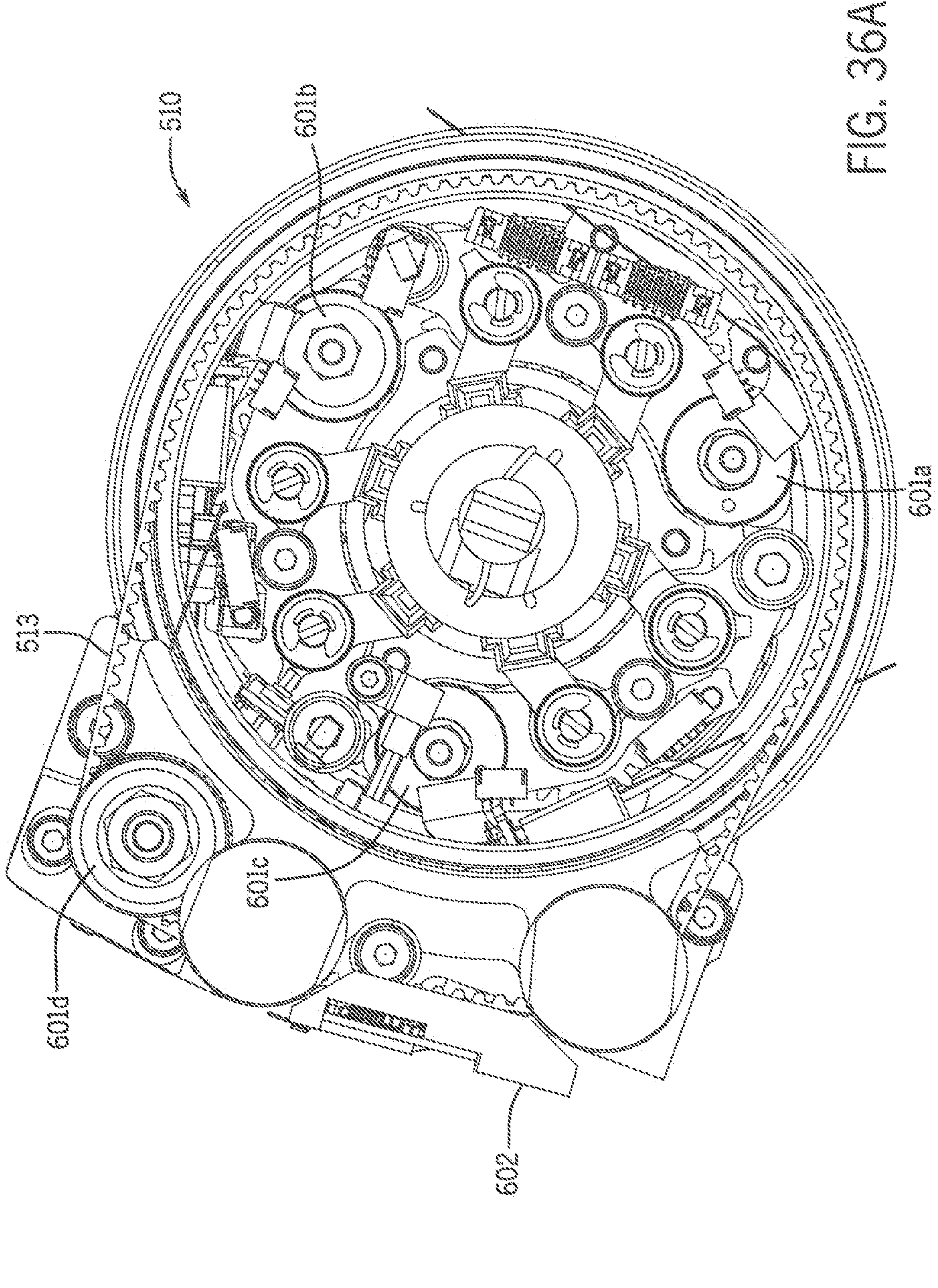
FIGS. 36A and 36B show, respectively, an end sectional and side interior perspective view of an exemplary slave hub.
Figure 36B:
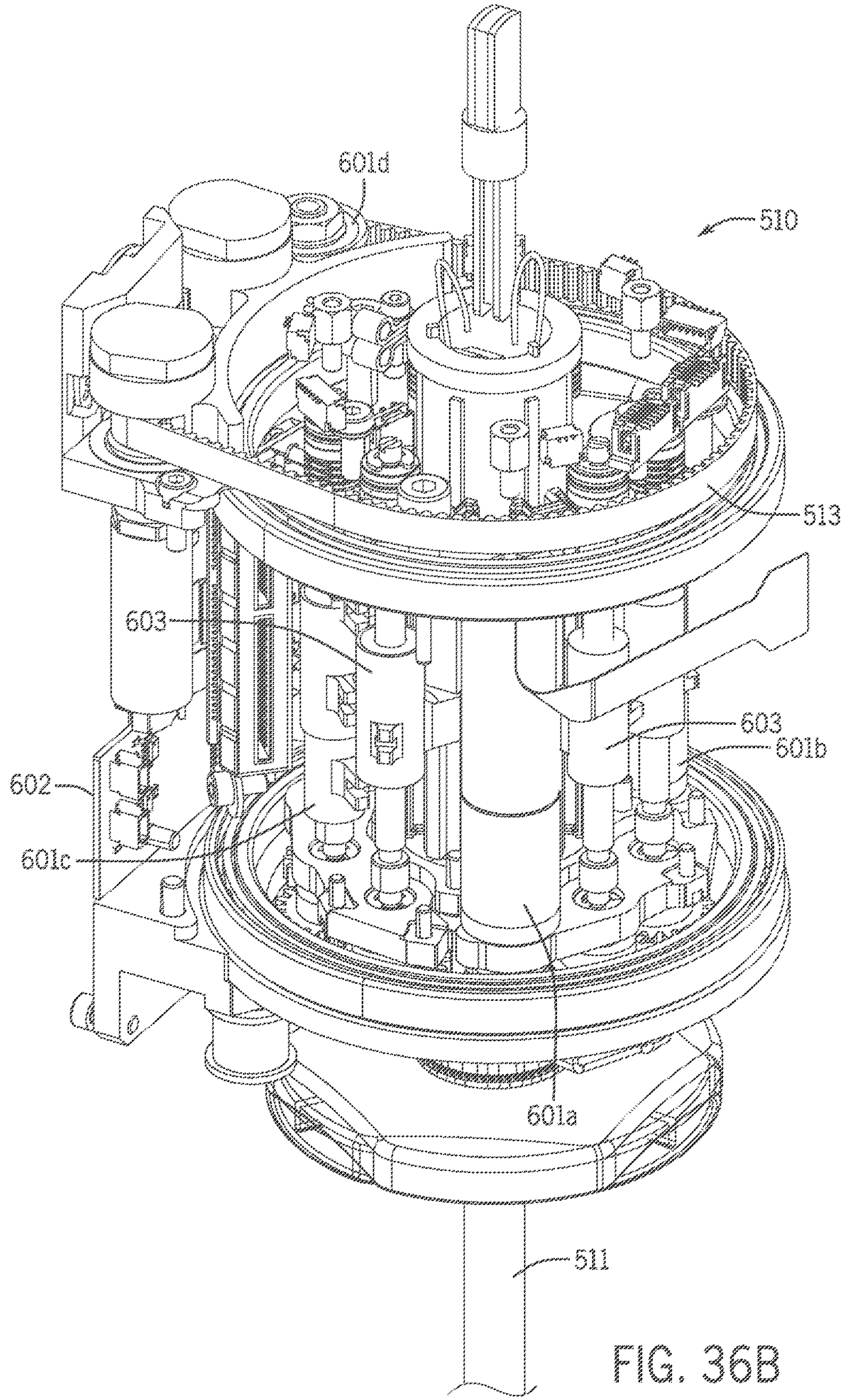

Further details regarding the components and operation of slave hub 510 are described with respect to FIGS. 36A and 36B. Slave hub 510 of translational instrument interface 503 affixed to slave unit 501 includes one or more motors, e.g., first motor 601*a*, second motor 601*b*, third motor 601*c*, and fourth motor 601*d*, operatively coupled, e.g., via electrical wiring, with the control system via circuit board 602. Motors 601*a*-601*d* receive signals indicative of measured movements and trigger actuation of handle 403, as measured by one or more sensors 410 coupled to handle 403. Those signals are processed by the control system, which in turn provides signals to the motors that actuate translational instrument interface 503 to thereby replicate the micro-movements corresponding to those input at handle 403. First motor 601*a*, second motor 601*b*, and third motor 601*c* are coupled directly to translation transmission system 603 of translational instrument interface 503 for actuating end-effector 512 in the open/close, pitch, and yaw degrees-of-freedom. Translation transmission system 603 includes a plurality of transmission elements, e.g., cables and/or lead screws, such that each of the plurality of transmission elements are coupled to first motor 601*a*, second motor 601*b*, and third motor 601*c* at one end, and to the first, second, and third end-effector links at the opposite end, to move the end-effector in the open/close, pitch, and yaw degrees-of-freedom. Translation transmission system 603 may include a plurality of lead screws and/or closed cable loops. Fourth motor 601*d* actuates rotation of slave instrument 503 via pronosupination timing belt 513. As will be understood by a person having ordinary skill in the art, slave hub 510 may include any combination of motors 601*a*-601*d*, e.g., only the one or more motors for actuating end-effector 512 in the open/close degree-of-freedom and the motor for rotating end-effector 512 in the pronosupination degree-of-freedom when a non-articulated instrument is used.

Circuit board 602 also may include one or more sensors designed to detect undesired movement of translational instrument interface 503, and electrically communicate with first motor 601*a*, second motor 601*b*, third motor 601*c*, and fourth motor 601*d* to resist such undesired movement.

Figure 36C:
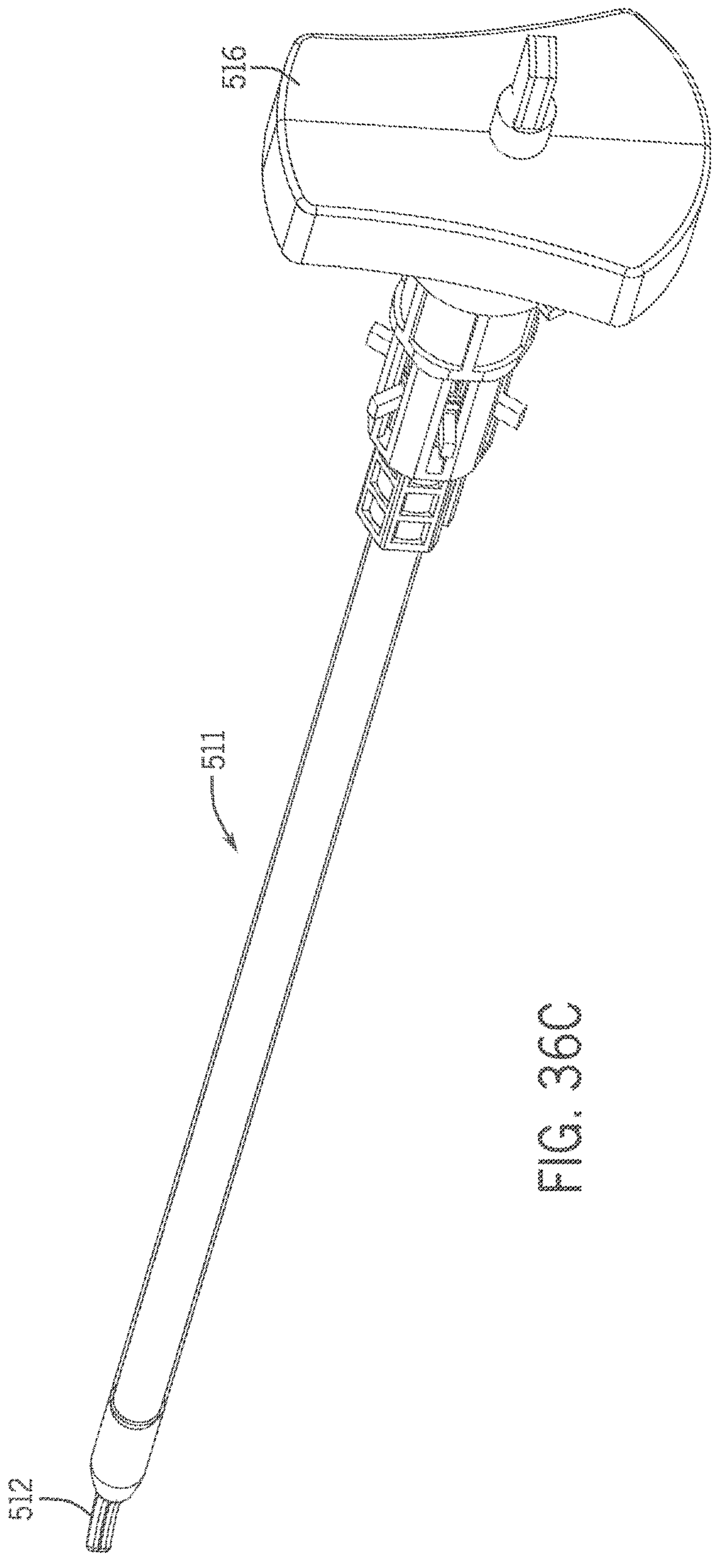
FIGS. 36C and 36D are, respectively, a perspective side view of a slave instrument and a detailed interior view of an end-effector constructed in accordance with the principles of the present invention.

In accordance with one aspect of the present invention, the control system may identify the kinematics of end-effector 512 of translational instrument interface 503 by reading out identifier element 516, e.g., RFID token integrated with the instrument, as shown in FIG. 36C, wherein the RFID token contains information on the kinematic configuration of the instrument. In particular, the control system, based on the information read from identifier element 516, may configure operation of the one or more motors that interface with translational instrument interface 503 to operate differently (e.g. to turn simultaneously clockwise or one clockwise and the other counterclockwise) to cause actuations of the end-effector elements. For example, in FIG. 36D, a forceps-type end-effector having parallel-serial instrument kinematics is described. For this configuration, first motor 601*a* may be operatively coupled to a first link of end-effector 512', e.g., a first blade, via transmission element 514*a* of the translation transmission system, such that first motor 601*a* causes the first link of end-effector 512' to move outward/inward. Second motor 601*b* may be operatively coupled to a second link of end-effector 512', e.g., second blade, via transmission element 514*b* of the translation transmission system, such that second motor 601*b* causes the second link of end-effector 512' to move outward/inward. Thus, the control system may instruct first motor 601*a* to move the first link of end-effector 512' outward via transmission element 514*a*, while simultaneously instructing second motor 601*b* to move the second link of end-effector 512' outward via transmission element 514*b*, thereby causing end-effector 512' to open based on actuation of trigger 412 of handle 403. Conversely, the control system may instruct first motor 601*a* to move the first link of end-effector 512' inward via transmission element 514*a*, while simultaneously instructing second motor 601*b* to move the second link of end-effector 512' inward via transmission element 514*b*, thereby causing end-effector 512' to close based on actuation of trigger 412 of handle 403. Therefore, first motor 601*a* and second motor 601*b* may cause end-effector 512' to move in the open/close degree-of-freedom.

The control system may instruct first motor 601*a* to move the first link of end-effector 512' outward via transmission element 514*a*, while simultaneously instructing second motor 601*b* to move the second link of end-effector 512' inward via transmission element 514*b*, thereby causing end-effector 512' to pitch upward based on rotation of handle 403 about handle axis $\theta_9$. Conversely, the control system may instruct first motor 601*a* to move the first link of end-effector 512' inward via transmission element 514*a*, while simultaneously instructing second motor 601*b* to move the second link of end-effector 512' outward via transmission element 514*b*, thereby causing end-effector 512' to pitch downward based on rotation of handle 403 about handle axis $\theta_9$. Therefore, first motor 601*a* and second motor 601*b* may cause end-effector 512' to move in the pitch degree-of-freedom.

Third motor 601*c* may be operatively coupled to a third link of end-effector 512' via transmission element 514*c* of the translation transmission system such that third motor 601*c* causes end-effector 512' to move in the yaw degree-of-freedom based on rotation of handle 403 about handle axis $\theta_8$. Fourth motor 601*d* may be operatively coupled to first motor 601*a*, second motor 601*b*, third motor 601*c*, and surgical instrument 511 via a rotatable pronosupination timing belt 513 such that fourth motor 601*d* causes first motor 601*a*, second motor 601*b*, third motor 601*c*, and surgical instrument 511, and thereby end-effector 512', to rotate in the pronosupination degree-of-freedom based on rotation of ball 413 of handle 403.

Figure 36D:
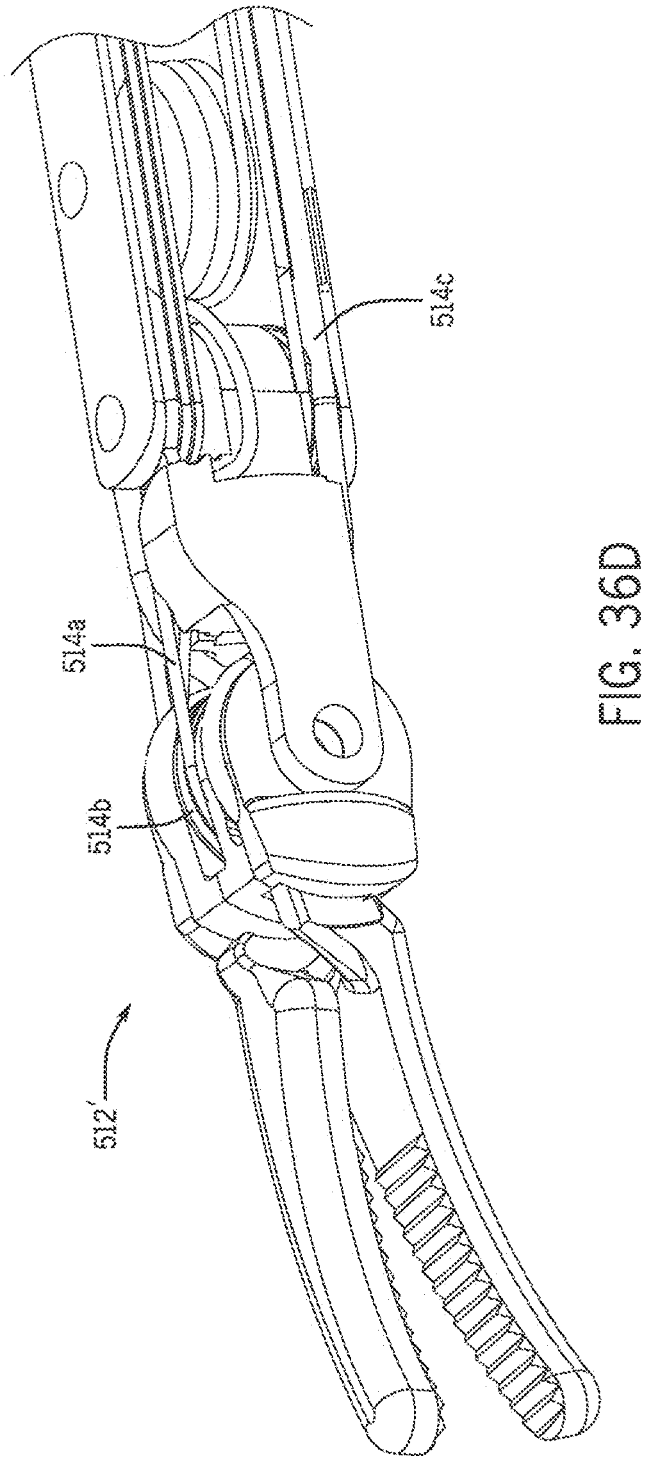
Figure 36E:
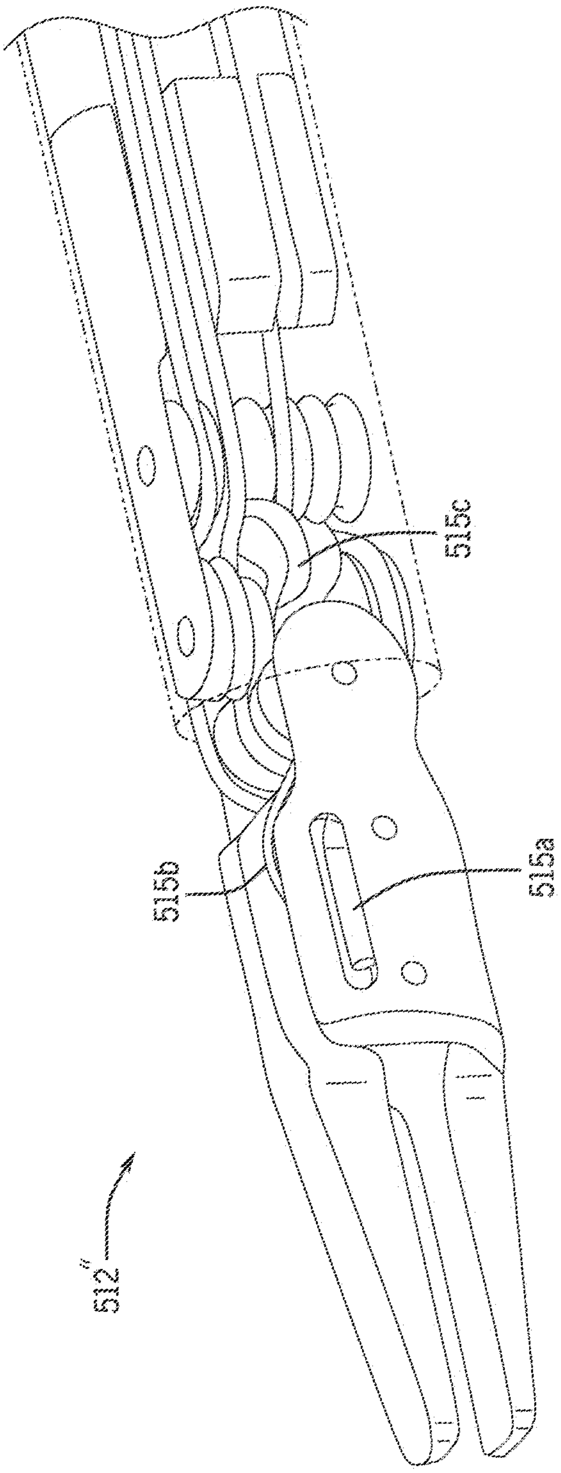
FIG. 36E is a detailed view of an alternative embodiment of an exemplary end-effector.

Referring now to FIG. 36E, an end-effector having serial-serial instrument kinematics is described. For example, first motor 601*a* may be operatively coupled to a first link of end-effector 512" via transmission element 515*a* of the translation transmission system such that first motor 601*a* causes end-effector 512" to move in the open/close degree-of-freedom based on actuation of trigger 412 of handle 403. Second motor 601*b* may be operatively coupled to a second link of end-effector 512" via transmission element 515*b* of the translation transmission system such that second motor 601*b* causes end-effector 512" to move in the pitch degree-of-freedom based on rotation of handle 403 about handle axis $\theta_9$. Third motor 601*c* may be operatively coupled to a third link end-effector 512" via transmission element 515*c* of the translation transmission system such that third motor 601*c* causes end-effector 512" to move in the yaw degree-of-freedom based on rotation of handle 403 about handle axis $\theta_8$. Fourth motor 601*d* may be operatively coupled to first motor 601*a*, second motor 601*b*, third motor 601*c*, and surgical instrument 511 via a rotatable pronosupination timing belt 513 such that fourth motor 601*d* causes first motor 601*a*, second motor 601*b*, third motor 601*c*, and surgical instrument 511, and thereby end-effector 512", to rotate in the pronosupination degree-of-freedom based on rotation of ball 413 of handle 403.

Figure 37:
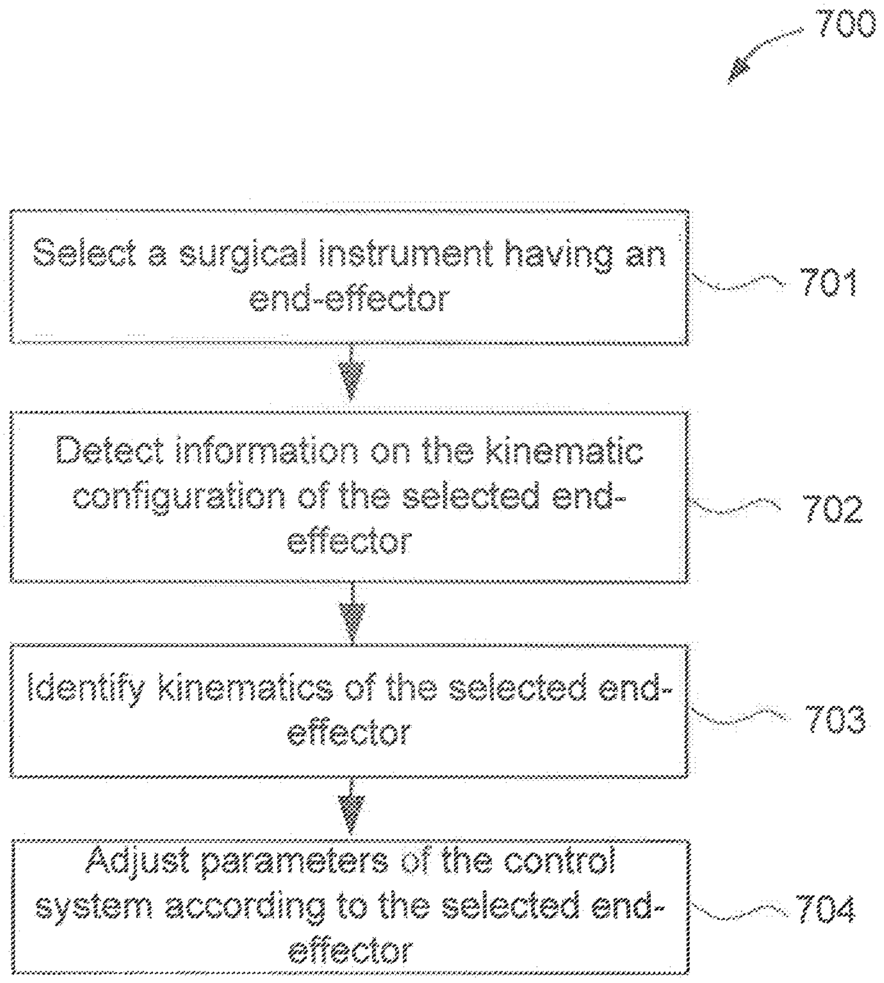
FIG. 37 shows a flow chart illustrating exemplary method steps for identifying the kinematics of a selected end-effector.

In accordance with one aspect of the invention, the control system may read information stored on identifier element 516, e.g., an RFID token, that is integrated with the instrument to identify the kinematics of end-effector 512 of translational instrument interface 503, as outlined in method steps 700 enumerated in FIG. 37. At step 701, the user selects a surgical instrument having an end-effector to be used with the hybrid telemanipulator. For example, the surgical instrument may have an end-effector having parallel-serial instrument kinematics as shown in FIG. 36D or serial-serial instrument kinematics as shown in FIG. 36E. The surgical instrument then may be coupled to the slave unit of the hybrid telemanipulator. At step 702, the control system detects information for the kinematic configuration of the selected end-effector. For example, the control system may read out an RFID token integrated with surgical instrument 511, which contains information on the kinematic configuration of the selected end-effector, e.g., whether the selected end-effector has parallel-serial instrument kinematics or serial-serial instrument kinematics. The RFID token may be, for example, an inductively-read microchip that contains identification information that may be scanned by a reader disposed on the slave hub and operatively coupled to the control system. Alternatively, the function of identifier element 516 may be provided by, e.g., an optical tag such as a bar code, QR code, Datamatrix, Aztec code, or Semacode, disposed on the surgical instrument 511 that is read by the slave hub. If the surgical instrument has not yet been coupled to the slave unit of the hybrid telemanipulator, surgical instrument may be coupled to the slave unit of the hybrid telemanipulator after step 702.

At step 703, the control system identifies the kinematics of the selected end-effector based on the information detected at step 702 to determine which type of end-effector is coupled to the slave unit of the hybrid telemanipulator. At step 704, the control system adjusts its parameters based on the identity of the selected end-effector so that the hybrid telemanipulator may be properly actuated. For example, if the end-effector has parallel-serial instrument kinematics, the control system will include parameters that instruct first motor 601*a* and second motor 601*b* to simultaneously actuate the first and second end-effector links to move the end-effector in the open/close and pitch degrees-of-freedom as described above. If the end-effector has serial-serial instrument kinematics, the control system will include parameters that instruct first motor 601*a* to actuate the end-effector in the open/close degree-of-freedom, and second motor 601*b* to actuate the end-effector in the pitch degree-of-freedom as described above.

Figure 38:
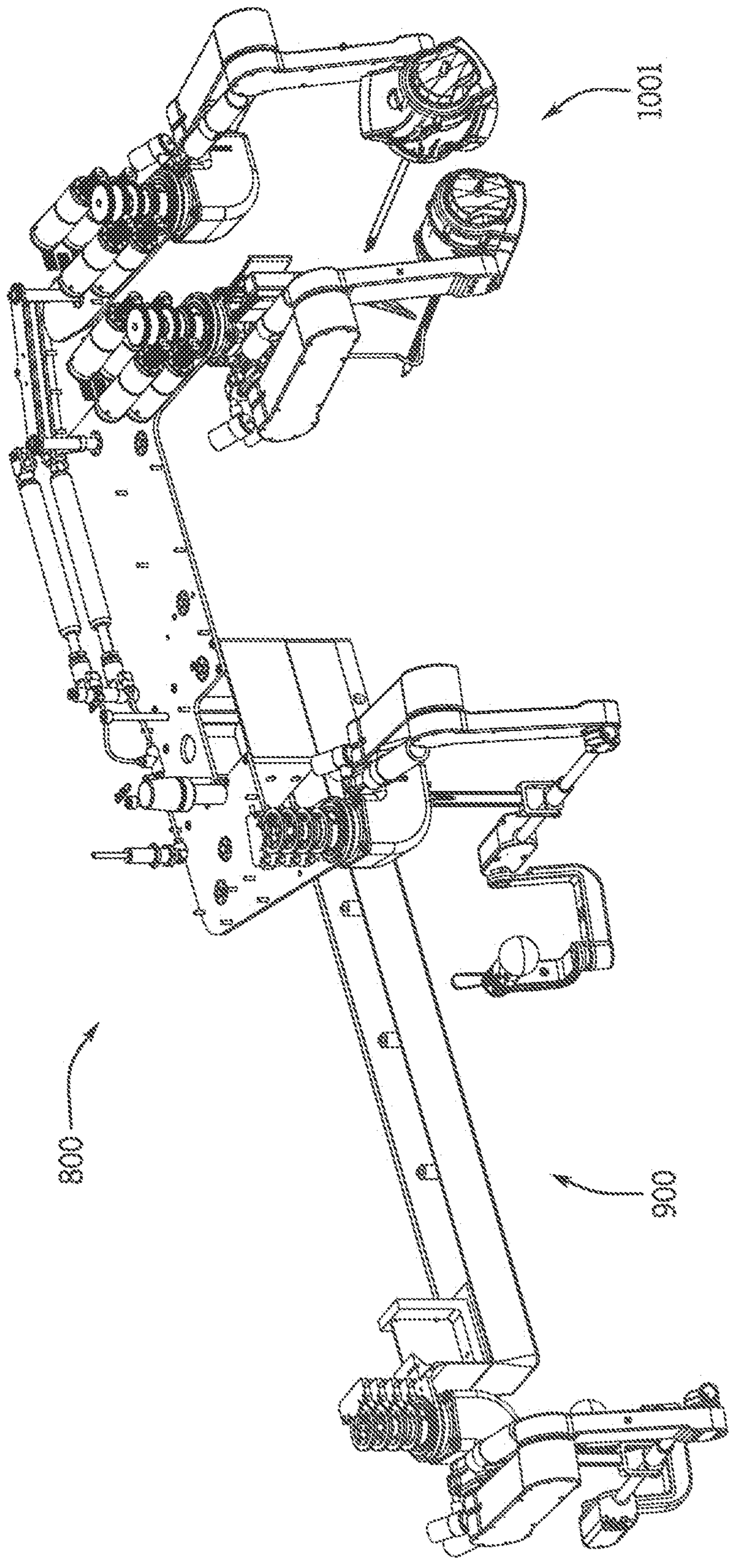
FIG. 38 shows an alternative exemplary embodiment of a remotely actuated surgical robot system of the present invention.

Referring to FIG. 38, an alternative exemplary embodiment of a remotely actuated surgical robot system wherein all degrees-of-freedom are controlled electromechanically is described. Although all seven of the degrees-of-freedom, e.g., inward/outward, upward/downward, left/right, yaw, pitch, open/close, and pronosupination, are controlled electromechanically via a system of sensors, motors, and a control system, system 800 retains a mechanical constraint element as described above at the master unit, thereby creating a single virtual stationary point, e.g., remote center-of-motion, at the slave unit. Therefore, system 800 does not require coordinate transform and complex control system to align slave unit 1001 with an incision. The mechanical constraint and the corresponding remote-center-of-motion ensure that this design, is much simpler and safer than when using generic robotic arms.

Figure 39:
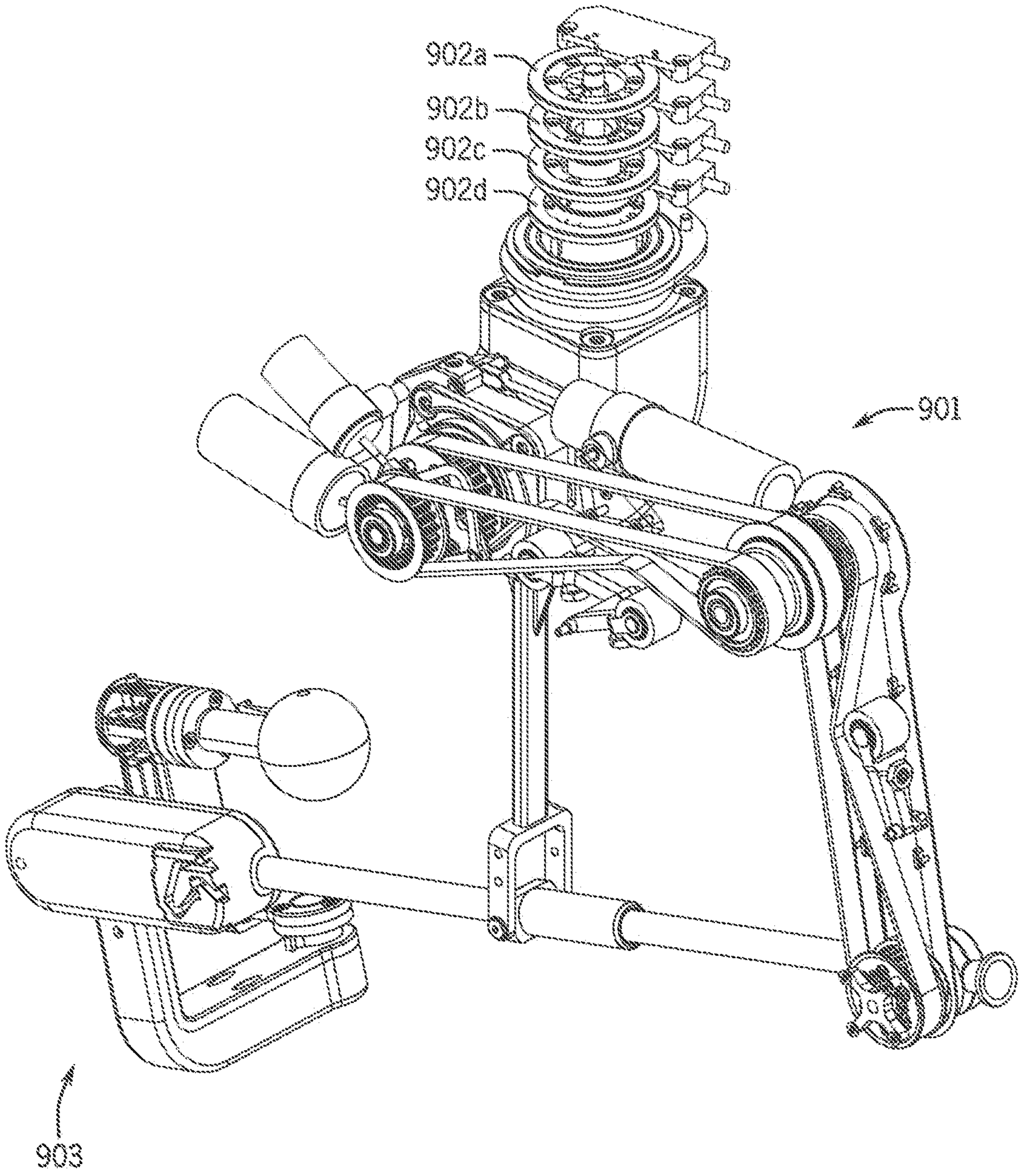
FIG. 39 shows interior side perspective view of the master unit of the remotely actuated surgical robot system of FIG. 38.

Referring now to FIG. 39, master unit 901 is constructed similarly to master unit 401 of FIGS. 34A and 34B, except that instead of a plurality of cables and pulleys of the mechanical transmission coupled to pulley P1, master unit 901 includes one or more sensors, e.g., sensor 902*a*, sensor 902*b*, sensor 902*c*, and sensor 902*d*, operatively coupled to each of the four pulleys of pulley P1. Sensors 902*a*-902*d* measure rotational movement by measuring angle and position of pulley P1 in response to movement applied to handle 903 of master unit 901 via a plurality of master links, joints, and cables. Each of the four sensors measures movement of a joint of master unit 901 via each of the four pulleys of pulley P1, thereby measuring movement of master unit 901 in four degrees-of-motion. However, the mechanical constraint constrains movement of master unit 901 by removing one degree-of-freedom of motion, thereby resulting in movement of slave unit 1001 in three degrees-of-freedom of motion, e.g., inward/outward, upward/downward, and left/right.

Handle 903 is constructed similarly to handle 403 of FIGS. 34A and 34B. For example, handle 903 includes one or more sensors 410 and circuit board 411, such that micro movements applied at handle 903 may be transmitted to the end-effector of slave unit 1001 via one or more sensors 410 and the one or more motors coupled to the end-effector of slave unit 1001 to move the end-effector in the open/close, pitch, yaw, and pronosupination degrees-of-freedom.

Regarding transmission of macro-movements, sensor 902*a*, sensor 902*b*, sensor 902*c*, and sensor 902*d* generate signals indicative of the measured rotation of pulley P1 by the respective sensors, and transmit the signals to one or more motors coupled to slave unit 1001 via a control system, to thereby replicate the translational macro-movements applied at handle 903 coupled to master unit 901. For example, electrical cables may extend from master unit 901 to the control system, e.g., unit containing control electronics, and additional electrical cables may extend from the control system to the one or more motors coupled to slave unit 1001.

Figure 40A:
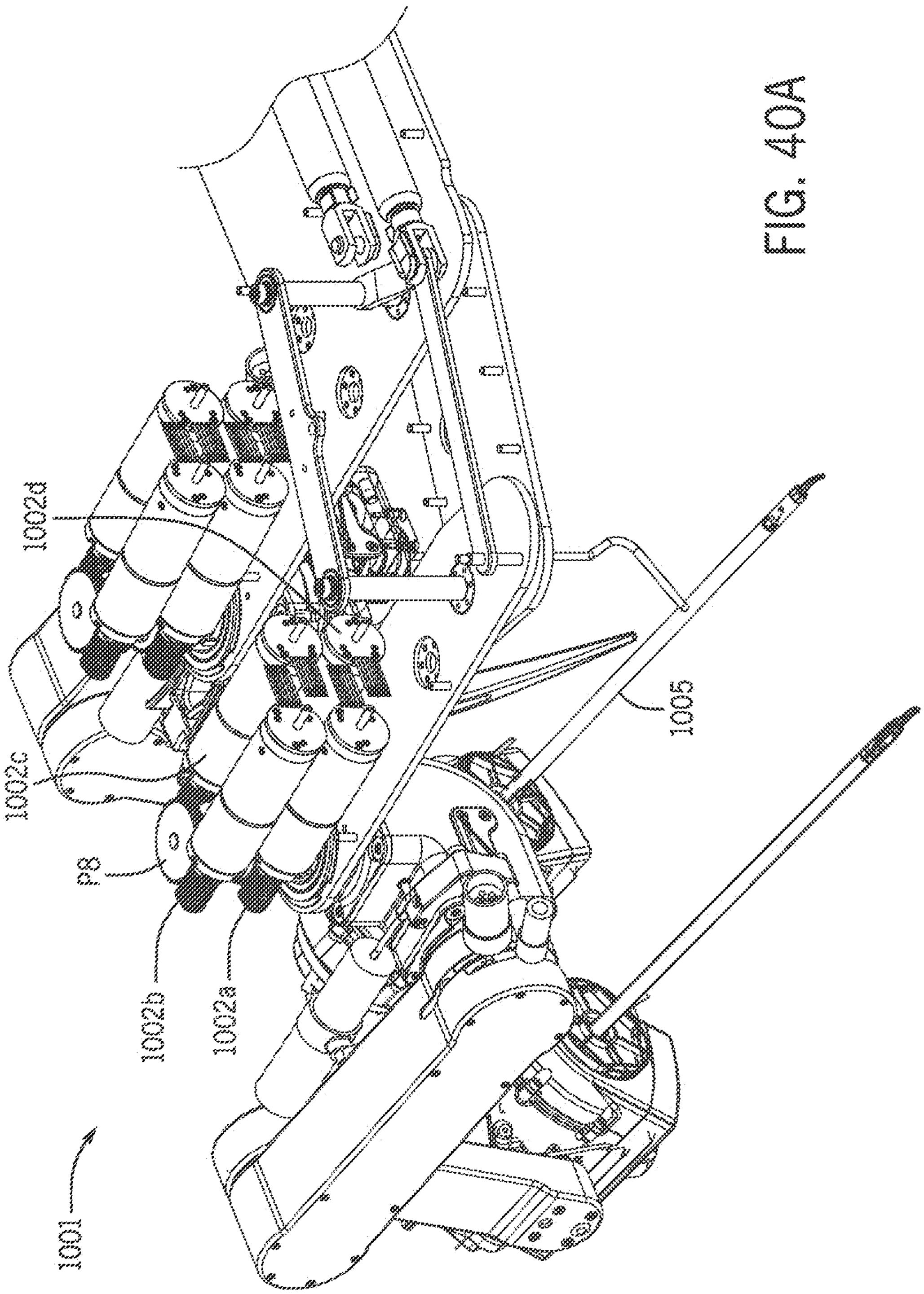
FIGS. 40A and 40B are forward and rearward perspective views of the slave unit of the remotely actuated surgical robot system of FIG. 38.
Figure 40B:
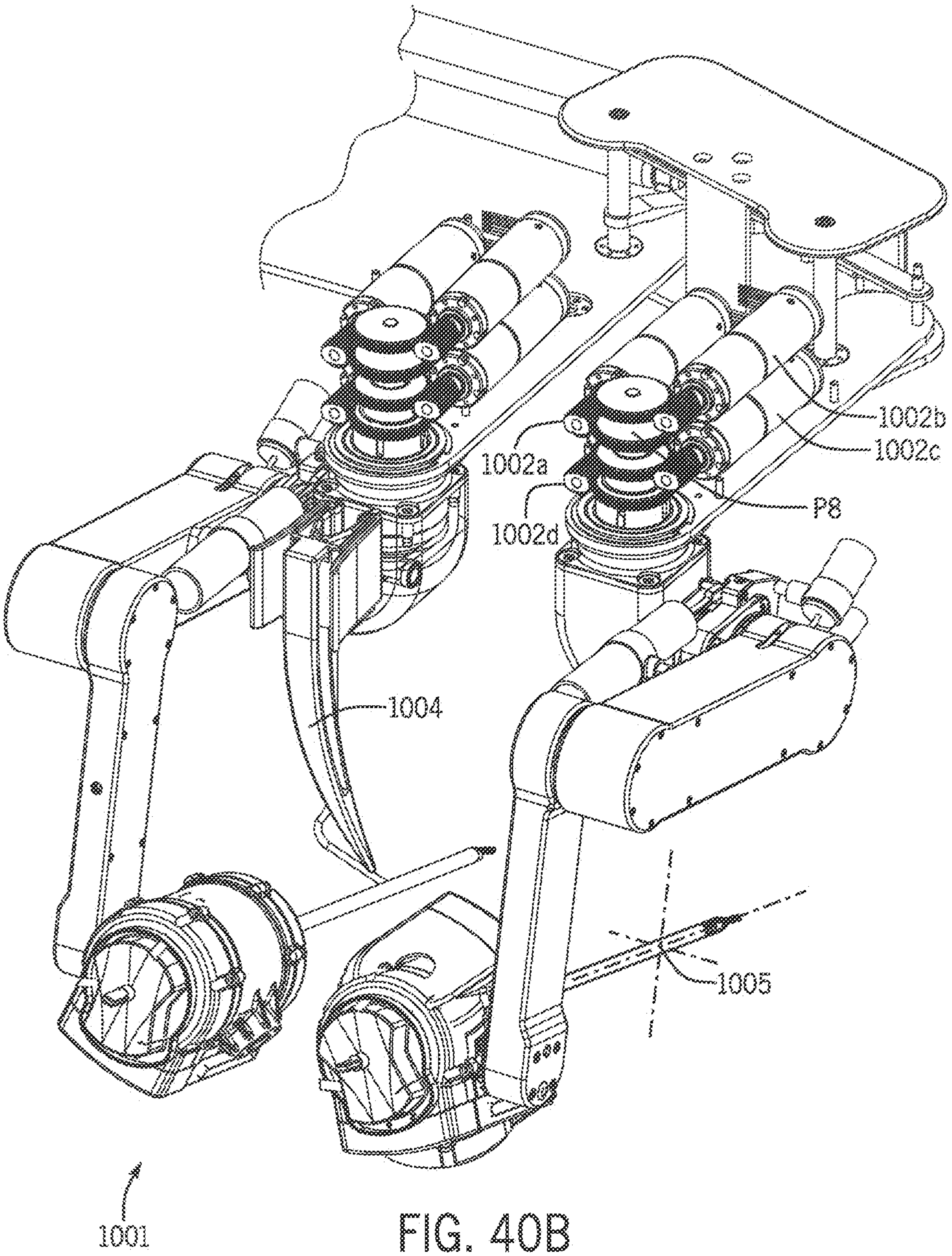

With respect to FIGS. 40A and 40B, slave unit 1001 is constructed similarly to slave unit 501 of FIGS. 35A and 35B. For example, slave unit 1001 includes first motor 601*a*, second motor 601*b*, third motor 601*c*, and fourth motor 601*d* operatively coupled to the end-effector of slave unit 1001, such that micro-movements applied at handle 903 may be transmitted to the end-effector of slave unit 1001 via one or more sensors 410, and first motor 601*a*, second motor 601*b*, third motor 601*c*, and fourth motor 601*d* to move the end-effector in the open/close, pitch, yaw, and pronosupination degrees-of-freedom. Slave unit 1001 differs from slave unit 501 in that instead of a plurality of cables and pulleys of the mechanical transmission coupled to pulley P8, slave unit 1001 includes one or more motors, e.g., first motor 1002*a*, second motor 1002*b*, third motor 1002*c*, and fourth motor 1002*d*, operatively coupled to each of the four pulleys of pulley P8. The one or more motors are coupled to a circuit board for receiving signals indicative of the measured rotation of pulley P1 by sensor 902*a*, sensor 902*b*, sensor 902*c*, and sensor 902*d* in response to movement applied to handle 903 of master unit 901, to thereby actuate pulley P8 to replicate the translational macro-movements applied on handle 903 coupled to master unit 901 at slave unit 1001 via a plurality of slave links, joints, timing belts, and/or a system of cables and pulleys. For example, first motor 1002*a* is operatively coupled to and controls movement of first slave link 505*a*, second motor 1002*b* is operatively coupled and controls movement of to second slave link 505*b*, third motor 1002*c* is operatively coupled to and controls movement of third slave link 505*c*, and fourth motor 1002*d* is operatively coupled to and controls movement of translational instrument interface 503 via pulley P8 and the plurality of slave joints, timing belts, and/or system of cables and pulleys.

As the mechanical constraint of master unit 901 constrains movement of master unit 901 to movement in three degrees-of-freedom, e.g., inward/outward, upward/downward, and left/right, movement of first slave link 505*a*, second slave link 505*b*, third slave link 505*c*, and translational instrument interface 503 of slave unit 1001 by first motor 1002*a*, second motor 1002*b*, third motor 1002*c*, and fourth motor 1002*d*, respectively, is constrained to movement in three degrees-of-freedom, e.g., inward/outward, upward/downward, and left/right, about virtual stationary point 1005, e.g., remote center-of-motion.

Slave unit 1001 may include temporary incision pointer 1004 which points to virtual stationary point 1005, e.g., remote center-of-motion, created by the mechanical restraint at master unit 1001, such that virtual stationary point 1005 may be brought in coincidence with the surgical incision point, reducing trauma to the patient and improving cosmetic outcomes of the surgery. Temporary incision pointer 1004 may be removed prior to operation of surgical robot system 800.

Figure 41A:
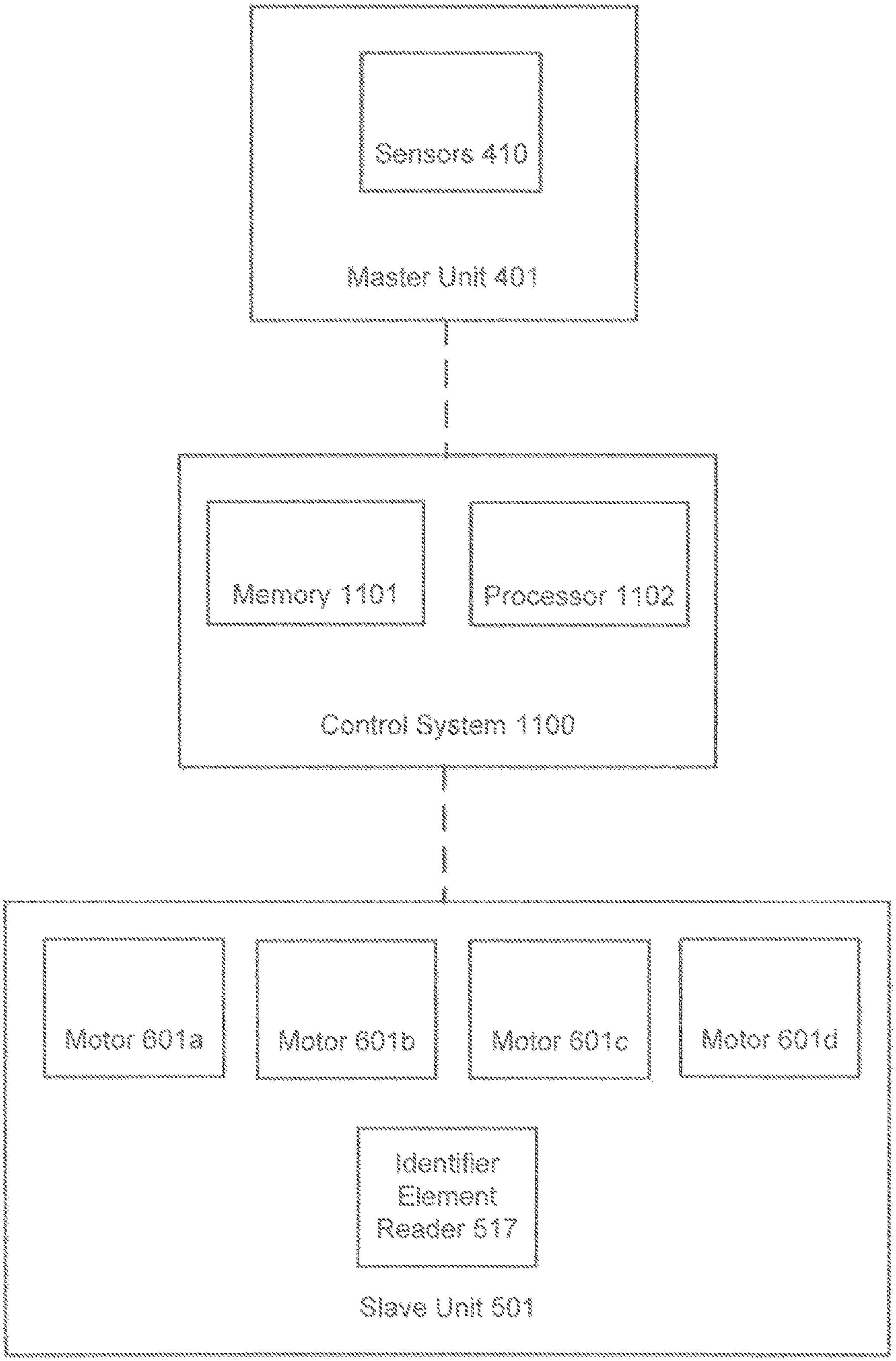
FIGS. 41A and 41B are alternative schematic illustrations of a control system suitable for use in the surgical robot system of the present invention.
Figure 41B:
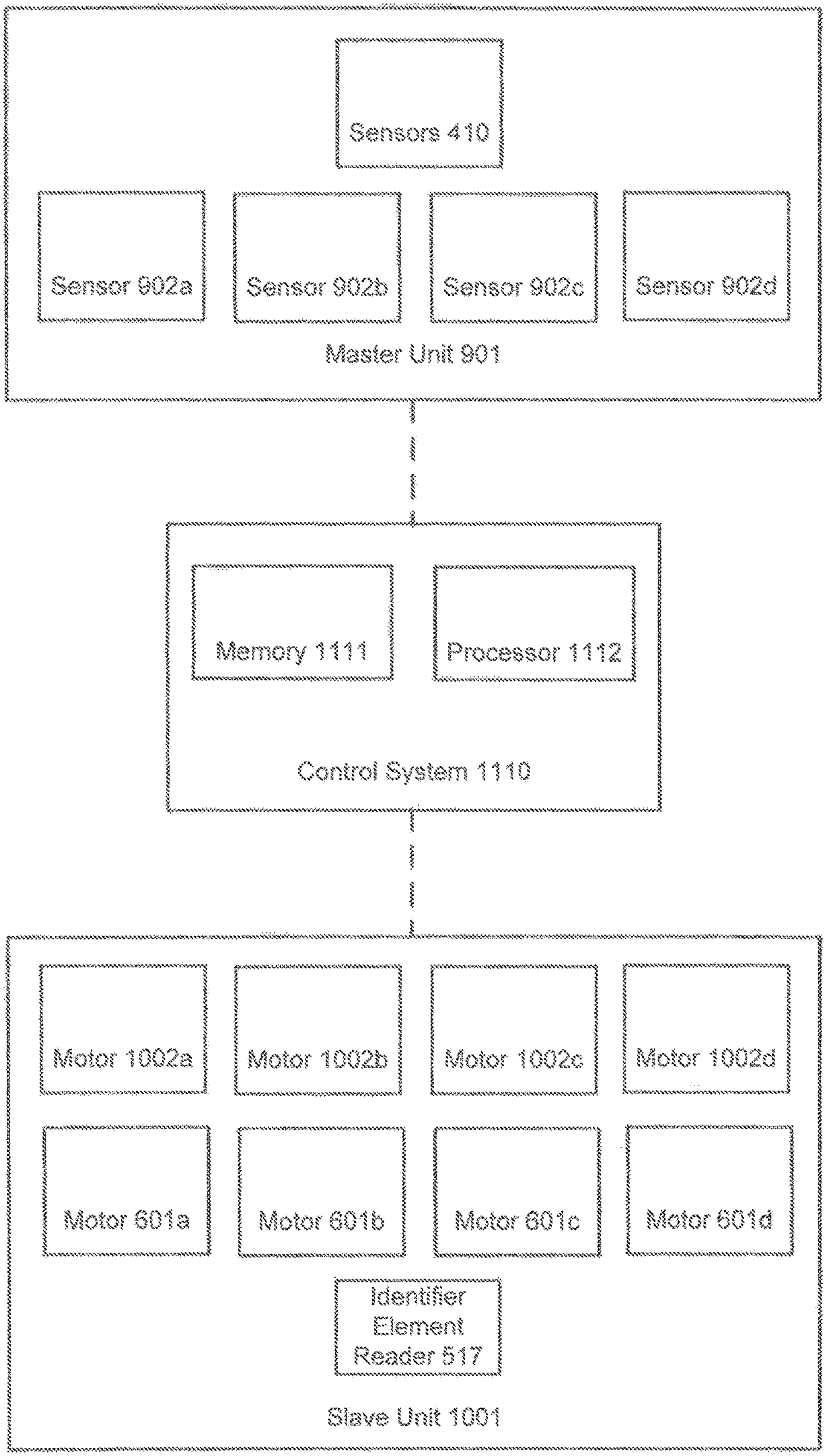

Referring now to FIGS. 41A and 41B, alternative embodiments of the control system of the surgical robot system are described. Control system 1100 of FIG. 41A, which may be integrated with system 100, includes non-transitory computer readable media, e.g., memory 1101, having instructions stored thereon that, when executed by processor 1102 of control system 1100 allow operation of the hybrid telemanipulators. In addition, control system 1100 may communicate with identifier element reader 517 of slave unit 501, either wirelessly or using an electric cable, so that memory 1101 may store the identity of the kinematic configuration of the end-effector read from identifier element 516, such that the instructions, when executed by processor 1102, cause the motors for controlling the end-effector in the open/close and pitch degrees-of-freedom to behave in accordance to the type of end-effector selected. Control system 1100 is electrically coupled, either wirelessly or using an electric cable, to the circuit boards of master unit 401 and, thereby, to one or more sensors 410 for receiving signals indicative of micro movements applied at handle 403. In addition, control system 1100 is electrically coupled, either wirelessly or using an electric cable, to the circuit boards of slave unit 501 and, thereby, to first motor 601*a*, second motor 601*b*, third motor 601*c*, and fourth motor 601*d* for actuating the micro movements of the end-effector, e.g., in the open/close, pitch, yaw, and pronosupination degrees-of-freedom.

Control system 1110 of FIG. 41B, which may be integrated with system 800, includes non-transitory computer readable media, e.g., memory 1111, having instructions stored thereon that, when executed by processor 1112 of control system 1110 allow operation of the hybrid telemanipulators. In addition, control system 1110 may communicate with identifier element reader 517 of slave unit 1001, either wirelessly or using an electric cable, and memory 1111 may store the identity of the kinematic configuration of the end-effector read from identifier element 516, such that the instructions, when executed by processor 1112, cause the motors for controlling the end-effector in the open/close and pitch degrees-of-freedom to behave in accordance to the type of end-effector selected. Control system 1110 is electrically coupled, either wirelessly or using an electric cable, to the circuit boards of master unit 901 and, thereby, to one or more sensors 410 for receiving signals indicative of micro movements applied at handle 903, and to sensor 902*a*, sensor 902*b*, sensor 902*c*, and sensor 902*d* for receiving signals indicative of macro movements applied at handle 903. In addition, control system 1110 is electrically coupled, either wirelessly or using an electric cable, to the circuit boards of slave unit 1001 and, thereby, to first motor 601*a*, second motor 601*b*, third motor 601*c*, and fourth motor 601*d* for actuating the micro movements of the end-effector, e.g., in the open/close, pitch, yaw, and pronosupination degrees-of-freedom, and to first motor 1002*a*, second motor 1002*b*, third motor 1002*c*, and fourth motor 1002*d* for actuating the macro-movements of the end-effector, e.g., in the inward/outward, upward/downward, and left/right degrees-of-freedom.

Figure 42A:
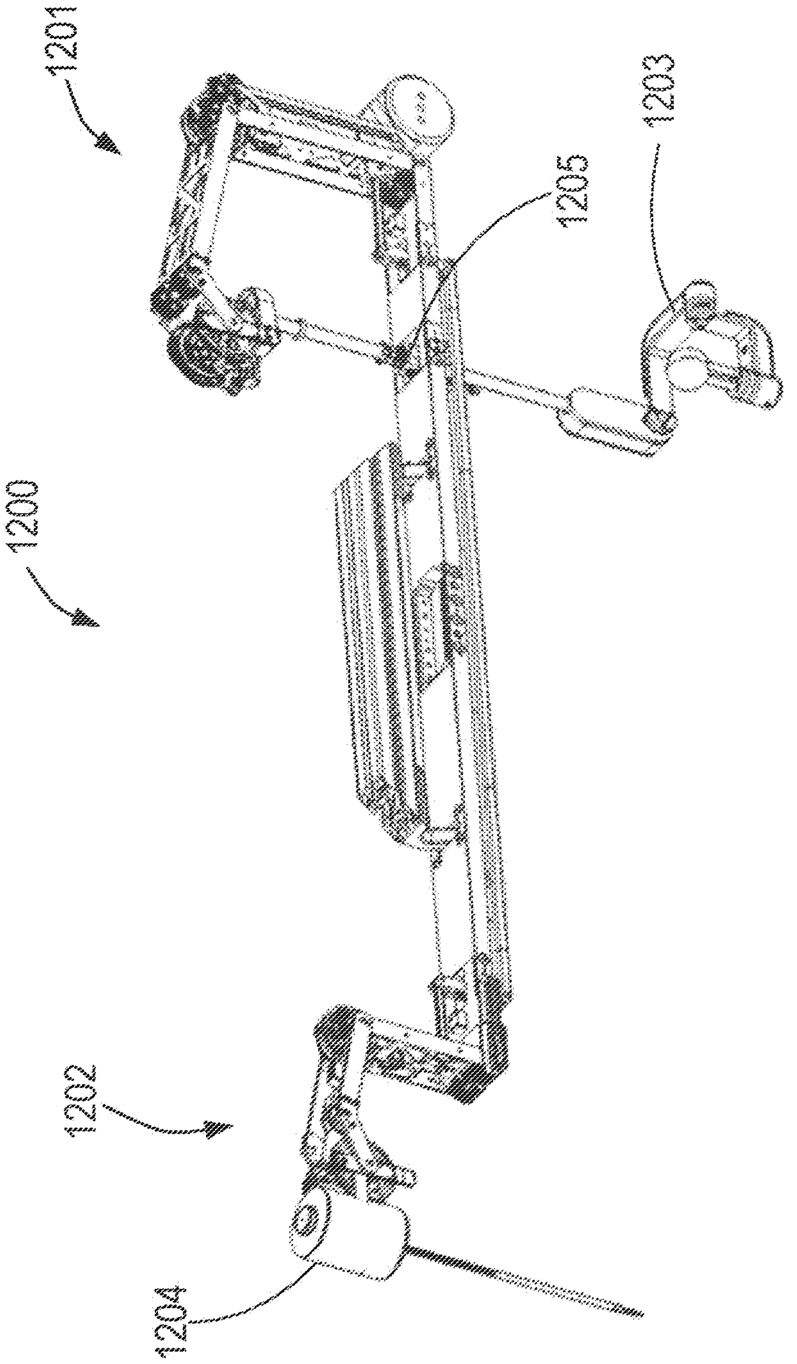
FIGS. 42A and 42B are side perspective views of alternative embodiments of telemanipulators constructed in accordance with the principles of the present invention.
Figure 42B:
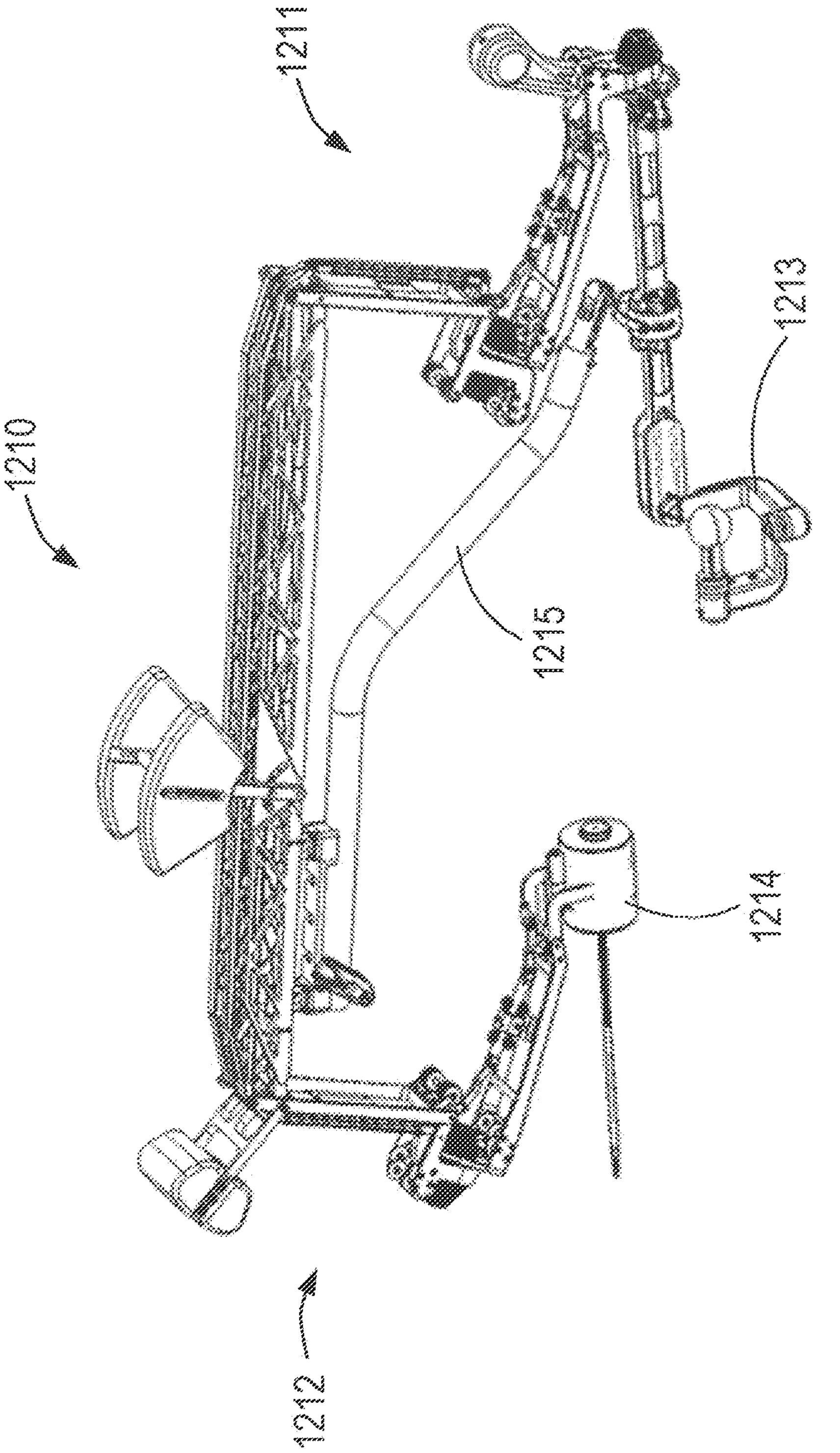

Referring now to FIGS. 42A and 42B, alternative applications of the principles of the present invention may be applied to alternative telemanipulator designs. For example, a telemanipulator constructed as described in U.S. Pat. No. 9,696,700 to Beira, depicted in FIG. 42A, may be modified to include handles and translational instrument interfaces for electromechanically controlling the micro movements of the end-effector, e.g., open/close, pitch, yaw, and pronosupination degrees-of-freedom, while the translational macro movements of the end effector, e.g., upward/downward, inward/outward, and left/right degrees-of-freedom, are controlled mechanically by a mechanical transmission system. Remotely actuated surgical robot system 1200 includes master unit 1201 directly mechanically coupled to slave unit 1202, handle 1203 coupled to master unit 1201, translational instrument interface 1204 coupled to slave unit 1202, and mechanical constraint 1205. Handle 1203 may be constructed similarly to handle 403 of FIGS. 34A and 34B, and translational instrument interface 1204 likewise may be constructed similarly to translational instrument interface 503 of FIGS. 35A and 35B. For example, handle 1203 includes one or more sensors, such that micro-movements applied at handle 1203 may be transmitted to the end-effector of translational instrument interface 1204 via the one or more sensors and one or more motors coupled to the end-effector of slave unit 1202 to move the end-effector in the open/close, pitch, yaw, and pronosupination degrees-of-freedom. Accordingly, the translational macro-movements applied at handle 1201 will be replicated by translational instrument interface 1204 in three degrees-of-freedom, e.g., inward/outward, upward/downward, and left/right, due to mechanical constraint 1203. Alternatively, remotely actuated surgical robot system 1200 may have seven degrees-of-freedom actuated electromechanically.

With respect to FIG. 42B, an alternative telemanipulator is described. For example, a telemanipulator constructed as described in U.S. Patent Pub. No. 2017/0245954 to Beira, may be modified to include handles and translational instrument interfaces for electromechanically controlling the micro-movements of the end-effector, e.g., open/close, pitch, yaw, and pronosupination degrees-of-freedom, while the translational macro-movements of the end effector, e.g., upward/downward, inward/outward, and left/right degrees-of-freedom, are controlled mechanically by a mechanical transmission system. Remotely actuated surgical robot system 1210 includes master unit 1211 mechanically coupled to slave unit 1212, handle 1213 coupled to master unit 1211, translational instrument interface 1214 coupled to slave unit 1212, and mechanical constraint 1215. Handle 1213 is constructed similarly to handle 403 of FIGS. 34A and 34B, and translational instrument interface 1214 is constructed similarly to translational instrument interface 503 of FIGS. 35A and 35B. For example, handle 1213 includes one or more sensors, such that micro-movements applied at handle 1213 may be transmitted to the end-effector of translational instrument interface 1214 via the one or more sensors and one or more motors coupled to the end-effector of slave unit 1212 to move the end-effector in the open/close, pitch, yaw, and pronosupination degrees-of-freedom. Accordingly, the translational macro-movements applied at handle 1213 will be replicated by the end-effector of translational instrument interface 1214 in three degrees-of-freedom, e.g., inward/outward, upward/downward, and left/right, due to mechanical constraint 1213. Alternatively, remotely actuated surgical robot system 1210 may have seven degrees-of-freedom actuated electromechanically.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed:

1. A system, comprising:

a master console including a first plurality of links and a first controller, the first plurality of links configured to move in response to movement applied at a handle coupled to at least one of the first plurality of links; and a slave console disposed separately from the master console, the slave console including a second plurality of links, a second controller, and a plurality of actuators, the plurality of actuators configured to be operatively coupled to the second plurality of links, the slave console being operatively coupled to the master console such that movement of the first plurality of links causes corresponding movement of the second plurality of links, the first controller being configured to detect movements of the first plurality of links and to transmit signals indicative of the movements of the first plurality of links to the second controller, the second controller being configured to, in response to receiving the signals, control the plurality of actuators to move the second plurality of links based on the movements of the first plurality of links, the second controller further being configured to, in response to receiving one or more inputs at the slave console, control the plurality of actuators to move the second plurality of links based on the one or more inputs.

2. The system of claim 1, wherein the second controller is configured to allow a user to select among a plurality of commands, each command from the plurality of commands being associated with a different configuration from a plurality of configurations of the slave console, the second controller further configured to cause, in response to receiving a command selected from the plurality of commands, the slave console to move into the configuration from the plurality of configurations associated with the command.

3. The system of claim 2, wherein the command is a home configuration command, and the configuration associated with the home configuration command is a home configuration, the second controller being configured to cause, in response to receiving the home configuration command, the slave console to move into the home configuration by causing the plurality of actuators to position a distal link of the second plurality of links such that an end effector, when coupled to the plurality of actuators, can be positioned within a trocar inserted in a patient.

4. The system of claim 2, wherein the command is a laparoscopic configuration command, and the configuration associated with the laparoscopic configuration command is a laparoscopic configuration, the second controller being configured to cause, in response to receiving the laparoscopic configuration command, the slave console to move into the laparoscopic configuration by causing the plurality of actuators to rotate a link from the second plurality of links and links distal to the link from the second plurality of links about an axis of a joint to cause a distal end of the slave console to face away from a patient.

5. The system of claim 1, wherein the plurality of actuators are configured to be operatively coupled to an end effector, and the second controller is configured to, in response to receiving the signals, to control the plurality of actuators to:

apply movement to at least one of the second plurality of links when the system is in a first state; and apply movement to the end effector while preventing movement of the second plurality of links when the system is in a second state different from the first state.

6. The system of claim 5, wherein the first state comprises a macro-synchronization state where the plurality of actuators cause macro-movements of at least one of the second plurality of links in response to the movements at the handle, and the second state comprises a micro-synchronization state where the plurality of actuators cause micro-movements of the end effector in response to the movements of the first plurality of links.

7. The system of claim 5, wherein the first controller configured to detect movements includes detecting an actuation pattern at the handle.

8. The system of claim 1, wherein the slave console includes a slave hub further comprising an instrument, the instrument configured to be removably coupled to the slave hub and to be sterilized prior to a surgical procedure.

9. The system of claim 8, further comprising a sterile interface configured to be installed on the slave hub, wherein the instrument is configured to be coupled to the slave hub after the sterile interface has been installed on the slave hub.

10. The system of claim 8, further comprising a control system operatively coupled to the master console and the slave console, the control system configured to:

determine that the instrument and the sterile interface have been properly installed by reading tags that have been integrated into the instrument and the sterile interface; and in response to determining that the instrument and the sterile interface have been properly installed, control the movements of at least one of the second plurality of links or the slave hub in response to the movements of the first plurality of links.

11. The system of claim 8, wherein the instrument is configured to be mechanically locked to the slave hub, the system further comprising:

a sensor configured to detect when the instrument has been mechanically locked to the slave hub.

12. The system of claim 1, wherein the master console is configured to be covered by a sterile drape and the handle is removably coupleable to the master console from outside of the sterile drape.

13. The system of claim 12, wherein the sterile drape is a first sterile drape, and the slave console is configured to be covered by a second sterile drape that is separate from the first sterile drape.

14. The system of claim 13, further comprising an instrument having a proximal end and a distal end, the distal end of the instrument including an end effector, and the proximal end of the instrument configured to couple to a distal link of the second plurality of links from outside of the second sterile drape when the slave console is covered by the second sterile drape.

15. The system of claim 1, wherein the handle is removably coupled to the master console via a screw attachment.

16. The system of claim 1, wherein the handle is configured to be removed and sterilized after a surgical procedure.

17. The system of claim 1, wherein the plurality of actuators are configured to be operatively coupled to an end effector, wherein the end effector is coupled to a distal end of an instrument shaft that is inserted into a patient through an incision point, wherein the master console is configured with a mechanical constraint such that the movements of the first plurality of links are constrained about a pivot point, thereby causing corresponding macro-movements of the second plurality of links to constrain the instrument shaft to pivot about the incision point.

18. The system of claim 1, wherein the plurality of actuators are configured to be operatively coupled to an end effector, the system further comprising a display operatively coupled to the master console, the display configured to permit a user to visualize the end-effector during operation of the system.

19. The system of claim 1, further comprising a removable incision pointer configured to permit alignment of a distal end of the slave console with a trocar positioned within a patient.

20. The system of claim 1, wherein the second plurality of links includes an angulation slave link, and the second controller is configured to:

cause the plurality of actuators to move the angulation slave link to an angle such that the angulation slave link and links of the second plurality of links proximal to the angulation slave link remain stationary during operation of the system; and cause the plurality of actuators to move the second plurality of links away from a patient such that a surgeon may move from the master console to manually perform surgery on the patient.

* * * * *